(12) United States Patent
Rabin et al.

(10) Patent No.: US 11,260,198 B2
(45) Date of Patent: Mar. 1, 2022

(54) SYSTEMS AND METHODS OF WAVE GENERATION FOR TRANSCUTANEOUS VIBRATION

(71) Applicant: Apollo Neuroscience, Inc., Pittsburgh, PA (US)

(72) Inventors: David Mayer Lowell Rabin, Pittsburgh, PA (US); Kathryn Fantauzzi, Pittsburgh, PA (US); Raymond G. Pelletier, Ben Avon, PA (US)

(73) Assignee: Apollo Neuroscience, Inc., Pittsburgh, PA (US)

( * ) Notice: Subject to any disclaimer, the term of this patent is extended or adjusted under 35 U.S.C. 154(b) by 0 days.

(21) Appl. No.: 16/722,299

(22) Filed: Dec. 20, 2019

(65) Prior Publication Data

US 2020/0215296 A1 Jul. 9, 2020

Related U.S. Application Data

(60) Provisional application No. 62/867,591, filed on Jun. 27, 2019, provisional application No. 62/788,564, (Continued)

(51) Int. Cl.
*A61M 21/02* (2006.01)
*A61H 1/00* (2006.01)
(Continued)

(52) U.S. Cl.
CPC ........... *A61M 21/02* (2013.01); *A61B 5/4812* (2013.01); *A61H 1/00* (2013.01); *A61H 23/00* (2013.01);
(Continued)

(58) Field of Classification Search
CPC ........ A61B 5/4812; A61M 2021/0022; A61M 21/02; A61M 2205/05; A61M 2205/3303
See application file for complete search history.

(56) References Cited

U.S. PATENT DOCUMENTS

| 5,267,942 A | 12/1993 | Saperston |
| 9,202,352 B2 | 12/2015 | Levesque |

(Continued)

FOREIGN PATENT DOCUMENTS

| EP | 3436135 A1 | 2/2019 |
| WO | 2017173436 A1 | 10/2017 |
| WO | 2020142259 A1 | 7/2020 |

OTHER PUBLICATIONS

"European Application Serial No. 17776899.1, Extended European Search Report dated Sep. 2, 2019", Apollo Neuroscience, Inc., 7 pages.
(Continued)

*Primary Examiner* — Christine H Matthews
(74) *Attorney, Agent, or Firm* — GTC Law Group PC & Affiliates

(57) ABSTRACT

Systems and methods of assisting a subject to reach a target state include obtaining input of the target state of the subject; and generating a transcutaneous vibratory output to be applied to a portion of a body of the subject to assist the subject in achieving the target state, the transcutaneous vibratory output having variable parameters comprising a perceived pitch, a perceived beat, and a perceived intensity wherein the step of generating the transcutaneous vibratory output further comprises the step of modifying the variable parameters to correspond to the target state.

29 Claims, 16 Drawing Sheets

Related U.S. Application Data filed on Jan. 4, 2019, provisional application No. 62/788,605, filed on Jan. 4, 2019.

(51) Int. Cl.

| | | |
|---|---|---|
| *G16H 20/00* | (2018.01) | |
| *A61H 23/00* | (2006.01) | |
| *G16H 20/30* | (2018.01) | |
| *G16H 40/67* | (2018.01) | |
| *G16H 10/60* | (2018.01) | |
| *G16H 50/30* | (2018.01) | |
| *G16H 20/70* | (2018.01) | |
| *A61B 5/00* | (2006.01) | |
| *G05B 19/416* | (2006.01) | |
| *A61M 21/00* | (2006.01) | |

(52) U.S. Cl.
CPC .......... *G05B 19/416* (2013.01); *G16H 10/60* (2018.01); *G16H 20/00* (2018.01); *G16H 20/30* (2018.01); *G16H 20/70* (2018.01); *G16H 40/67* (2018.01); *G16H 50/30* (2018.01); *A61H 2201/165* (2013.01); *A61H 2201/5005* (2013.01); *A61H 2201/5007* (2013.01); *A61H 2201/5023* (2013.01); *A61H 2230/045* (2013.01); *A61H 2230/085* (2013.01); *A61H 2230/105* (2013.01); *A61H 2230/203* (2013.01); *A61H 2230/305* (2013.01); *A61H 2230/425* (2013.01); *A61M 2021/0016* (2013.01); *A61M 2021/0022* (2013.01); *A61M 2021/0044* (2013.01); *A61M 2205/05* (2013.01); *A61M 2205/3303* (2013.01); *G05B 2219/37032* (2013.01)

(56) References Cited

U.S. PATENT DOCUMENTS

| | | |
|---|---|---|
| 9,656,078 B1 | 5/2017 | Danilov et al. |
| 10,228,764 B2 | 3/2019 | Levesque |
| 10,248,850 B2 | 4/2019 | Rihn et al. |
| 10,289,201 B2 | 5/2019 | Cruz-Hernandez |
| 10,974,020 B2 | 4/2021 | Rabin et al. |
| 2003/0001008 A1 | 1/2003 | Berrube et al. |
| 2003/0083599 A1 | 5/2003 | Kitov |
| 2007/0219470 A1 | 9/2007 | Talish et al. |
| 2009/0131993 A1 | 5/2009 | Harel et al. |
| 2009/0264789 A1 | 10/2009 | Wei et al. |
| 2009/0271217 A1 | 10/2009 | Hyde et al. |
| 2010/0057160 A1 | 3/2010 | De Ridder |
| 2012/0149973 A1 | 6/2012 | Holloway |
| 2013/0304165 A1 | 11/2013 | Rogers |
| 2014/0148872 A1 | 5/2014 | Goldwasser et al. |
| 2014/0163439 A1 | 6/2014 | Uryash et al. |
| 2014/0232534 A1 | 8/2014 | Birnbaum et al. |
| 2015/0335288 A1 | 11/2015 | Toth et al. |
| 2016/0074278 A1 | 3/2016 | Muench et al. |
| 2017/0224990 A1 | 8/2017 | Goldwasser et al. |
| 2017/0296429 A1 | 10/2017 | Mayo et al. |
| 2018/0042809 A1* | 2/2018 | Zipper .............. A61H 23/0263 |
| 2018/0133504 A1 | 5/2018 | Malchano et al. |
| 2018/0233226 A1 | 8/2018 | Ramsay et al. |
| 2019/0076643 A1 | 3/2019 | Siegle et al. |
| 2019/0103182 A1 | 4/2019 | Borshch et al. |
| 2019/0171292 A1 | 6/2019 | Levesque |
| 2020/0061377 A1 | 2/2020 | Siegle et al. |
| 2020/0147339 A1 | 5/2020 | Mayo et al. |
| 2020/0215297 A1 | 7/2020 | Rabin et al. |
| 2020/0215298 A1 | 7/2020 | Rabin et al. |
| 2020/0219615 A1 | 7/2020 | Rabin et al. |

OTHER PUBLICATIONS

"International Application Serial No. PCT/US19/67769, Invitation to Pay Additional Fees and, Where Applicable, Protest Fee dated Feb. 5, 2020", Apollo Neuroscience, Inc., 2 pages.

U.S. Appl. No. 16/722,238, filed Dec. 20, 2019, Pending.

U.S. Appl. No. 16/722,345, filed Dec. 20, 2019, Pending.

U.S. Appl. No. 16/722,350, filed Dec. 20, 2019, Pending.

PCT/US19/67769, Dec. 20, 2019, Pending.

"International Application Serial No. PCT/US19/67769, International Search Report and Written Opinion dated Apr. 22, 2020", Apollo Neuroscience, Inc., 64 pages.

"International Application Serial No. PCT/US19/67769, International Preliminary Report on Patentability dated Jul. 15, 2021", Apollo Neuroscience, Inc., 63 pages.

* cited by examiner

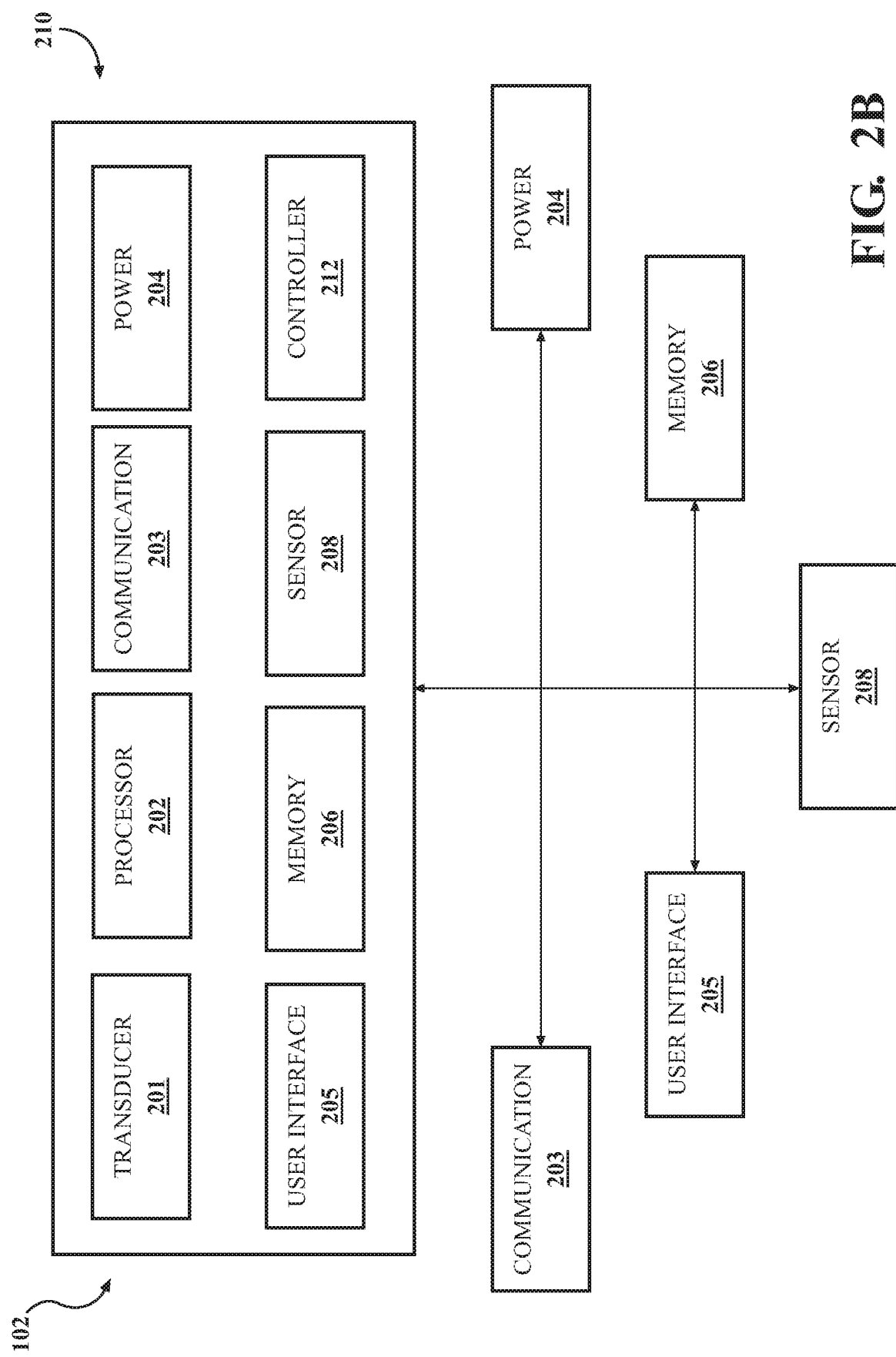

SYSTEMS AND METHODS OF WAVE GENERATION FOR TRANSCUTANEOUS VIBRATION

CLAIM TO PRIORITY

This application claims the benefit of the following provisional applications, which are hereby incorporated by reference in their entirety: U.S. Ser. No. 62/788,564, filed Jan. 4, 2019, U.S. Ser. No. 62/788,605, filed Jan. 4, 2019, and U.S. Ser. No. 62/867,591, filed Jun. 27, 2019.

BACKGROUND

Field

This disclosure provides systems and methods of facilitating neural or emotional state transitions.

Description of the Related Art

The autonomic nervous system (ANS) is a part of the peripheral and central nervous system and comprises the nerves that communicate between the brain stem and the body's internal organs. The ANS comprises the complementary sympathetic and parasympathetic branches or systems. The sympathetic nervous system is often referred to as a body's "fight or flight" system, as it prepares the body for intense physical activity to enhance the likelihood of survival when coping with threatening situations. The parasympathetic nervous system—sometimes called the "rest and digest" system—does the opposite, as it causes the body to relax, and it can reduce or inhibit many of the body's high energy functions that are required for effectively managing survival situations.

The ANS functions below one's level of awareness through complex interactions between its two branches to respond quickly and continuously to perturbations that threaten the stability of the body's internal environment. As such, the sympathetic and parasympathetic systems work together to maintain homeostasis. Activity in the ANS may be modulated intentionally by activities such as meditation and deep breathing that improve parasympathetic activity.

The autonomic nervous system can be manipulated via sensory pathways. For example, in a resonance method periodic sensory stimulation may evoke a physiological response that peaks at certain stimulus frequencies. This includes a resonance mechanism that is characterized by the peaking of the physiological response versus frequency such that the periodic sensory signals evoke an excitation of oscillatory modes in certain neural circuits. The most common example of this phenomenon is music. Music resonates with each person slightly differently, but nonetheless in a highly similar manner, that has the capacity to reliably induce significant shifts in awareness, cognition, mood, and a host of other sensations. Fast loud music typically induces a sympathetic physiological and subjective response, while slow gentle quiet music tends to elicit the opposite parasympathetic response. This general rule with respect to intensity and frequency relationships to physiological and subjective responses are similar for tactile and most other stimuli.

Responses to sympathetic and parasympathetic stimulation are frequently antagonistic. For example, they have opposing or antagonistic effects on heart rate. While stimulation of the sympathetic branch increases heart rate, stimulation of the parasympathetic branch decreases heart rate. In addition, the body's response to activity in one branch depends on the level of activity in the other branch. Sympathetic and parasympathetic activity make up a complex, dynamic system that is continuously adjusting to changing conditions in the body and in the external environment. The ANS strives to optimize activity in each branch and to balance the two branches in real time, depending on both internal and external conditions, thereby maintaining homeostasis.

In certain diseases and conditions, the balance between sympathetic and parasympathetic system activity is implicated either causally or in attempted remediation.

Accordingly, ways for affecting a subject's health or condition by stimulating and refining the function of the sympathetic and/or parasympathetic branches of the ANS, both acutely and progressively over time, are desired. The present disclosure relates generally to a method and apparatus for affecting a subject's health or condition by using information regarding the sympathetic and/or parasympathetic branch of the autonomic nervous system to modulate and/or apply stimuli to the patient (e.g., as a function of the heart rate) that stimulates the sympathetic and/or parasympathetic branch.

SUMMARY

Throughout this disclosure, methods and systems herein are directed at assisting a subject to reach a target state (e.g. calm, focus, flow, presence of being, asleep, wakeful, relaxed, aroused, euphoric, or a performance state), maintain the target state, and/or prime the user to be able to achieve the target state. The subject may provide input about the desired target state to a processor associated with a transducer, and a transcutaneous vibratory output may be generated by the transducer to be applied to a portion of the subject's body. Throughout this disclosure, the transcutaneous vibratory output may be described as having variable parameters comprising a perceived pitch, a perceived beat, and a perceived intensity. Throughout this disclosure, a plurality of perceived pitches and/or a plurality of perceived beats may be used to generate the transcutaneous vibratory output. Throughout this disclosure, the transcutaneous vibratory output may be generated by multiplicatively combining a sine wave-shaped envelope with a wave pattern having a perceived pitch, such as in accordance with the equation: $[\sin(2.0*\pi*freq\_perceived\_pitch*t)]*[\sin(\pi*freq\_perceived\_beat*t)]$. Throughout this disclosure, a user's sensory thresholds, both lower and upper, may be used as bounds for the transcutaneous vibratory output that is generated. The sensory threshold may be determined via a calibration procedure, active data collection via survey questions, or passive data collection via monitoring mobile device and application usage. The variable parameters can be modified based on the target state desired, such as through a user interface of a device or automatically, and further to avoid habituation. The desired target state may be inferred based on the present condition of the subject, either determined manually and actively by user input or passively through users' mobile and environmental data and biometric or physiological sensing. Throughout this disclosure, physiologically sensed data may include any of: heart rate (HR), heart rate variability (HRV), galvanic skin response (GSR), movement, respiration rate, temperature, $SpO_2$, spirometry, EEG, ECG, EMG, $CO_2$, motion, blood pressure, or glucose. Achieving the target state may include generating a second transcutaneous vibratory output, such as if the first is ineffective, or a transcutaneous vibratory output with multiple segments. As with any of the embodiments herein, the processor of the transducer may be in communication with one or more sensors, with other systems, devices, or transducers and any processor thereof, or with a remote server.

Methods and systems disclosed herein are directed at assisting a subject to reach a target state with their feedback as aid. The desired target state of the user is determined and a transcutaneous vibratory output is generated, which is designed or programmed to facilitate achieving the target state, maintaining the target state, or priming the user to be able to achieve the target state. The transcutaneous vibratory output is applied to a portion of the subject's body (such as with a transducer) and user input on state achievement is obtained as feedback to the system. Failure to reach the target state may result in a second transcutaneous vibratory output being generated for application. In any of the embodiments of this disclosure, a user interface of a device comprising a transducer, or a second device in communication with the transducer, or an application executing on a mobile device in communication with the transducer may be used to select the target state and/or provide user feedback. A processor may be in electronic communication with the transducer and a user input device, wherein the processor causes the transducer to generate transcutaneous vibratory outputs when it receives input or instructions from the user input device.

Methods and systems disclosed herein are directed at assisting a subject to reach a target state with sensor-based measurements or third party data sources as feedback. Sensor-based measurements may include, but are not limited to, heart rate, heart rate variability, respiration rate, and galvanic skin response. Third party data sources may include, but are not limited to, a health informatics application, an electronic health record, a hospital data system, content of social media posts, metadata from use of a mobile device (smartphone), or content of communications. The desired target state of the user is determined and a transcutaneous vibratory output is generated which is designed or programmed to facilitate achieving the target state, maintaining the target state, or priming the user to be able to achieve the target state. The transcutaneous vibratory output is applied to a portion of the subject's body (such as with a transducer) and sensor-based measurements or third party data on state achievement is obtained as feedback to the system. Failure to reach the target state may result in a second transcutaneous vibratory output being generated for application. Reaching the target state may cause discontinuation of the stimulation, or generation of a maintenance stimulation protocol. A user interface of a device comprising a transducer, or a second device in communication with the transducer, or an application executing on a mobile device in communication with the transducer may be used to select the target state and provide user feedback. A processor may be in electronic communication with the transducer, a physiological sensor, and, optionally, a user input device, wherein the processor causes the transducer to generate transcutaneous vibratory outputs when it receives input or instructions from the user input device, sensor, or third party data source, and generate further transcutaneous vibratory outputs in response to a determination of goal achievement based on the sensor or third party data source.

Methods and systems disclosed herein are directed at calibrating a method and/or system of assisting a subject to reach a target state. A method of calibration may involve selecting a first transcutaneous vibratory output based on the determined target state of the user, applying the vibratory output and measuring its effectiveness, such as with sensors or user feedback. A second transcutaneous vibratory output is then used to reach the same target state and its effectiveness is similarly measured. A processor calibrates the method for achieving the target state based on the effectiveness determinations, choosing one of the vibratory outputs for subsequent attempts at achieving the target state, or generating a third transcutaneous vibratory output. The calibration method may alternatively utilize a plurality of transcutaneous vibratory outputs in a corresponding session whose effectiveness is determined. Once an effective transcutaneous vibratory output is identified, it is stored in a database. The database for other effective transcutaneous vibratory outputs and selecting one of said other effective transcutaneous vibratory outputs to be emitted with the electronic transducer.

Another method of calibration commences as soon as the user begins use of the stimulation device. For a period of time, this calibration involves determining a baseline, non-stressed state of a user by periodically measuring a physiological parameter (e.g. heart rate (HR), heart rate variability (HRV), galvanic skin response (GSR), movement, respiration rate, temperature, $SpO_2$, spirometry, EEG, ECG, EMG, heart rate, $CO_2$, motion, blood pressure, or glucose) using a sensor combined with routine assessments of mobile device user and metadata. Then, when there is a deviation from baseline identified by a processor of a device in communication with the sensor, a transcutaneous vibratory output is identified in response and communicated to the processor for generation and application by the transducer. The user may assist in identifying the baseline state during the calibration period by inputting information regarding their mood. The processor may also use contextual data periodically received from a mobile device to determine the baseline state, deviations therefrom, or mood. The contextual data, which may be used in any of the disclosed embodiments, may derive from content of social media, a navigation application, a calendar application, a movement tracker, an amount of usage of the mobile device, keystrokes input into the mobile device, or a project management application. As with all embodiments herein, if the transcutaneous vibratory output is not effective to assist the user to enter a target state, it may be modified (e.g. such as by varying one or more of the variable parameters), discontinued, or a second transcutaneous vibratory output may be generated and commenced.

Methods and systems disclosed herein are directed at predicting a user is leaving a target state or is not at or going to achieve a target state and then assisting the user to reach the target state. Prediction is done using electronic sensing of at least one of a physiological state with a wearable sensor/device or collected from a separate device/database (e.g. a smartphone, a fitness monitor, a smart watch, a smart speaker, a smart eyewear, a connected vehicle, or a smart headphones); or a contextual data of the user, to determine an emotional and/or physiological state, and then generating a transcutaneous vibratory output directed at addressing or avoiding the predicted state(s), and delivering it as needed. The transcutaneous vibratory output may have multiple segments, each having variable parameters. As with all embodiments herein, if the transcutaneous vibratory output is not effective to assist the user to avoid the predicted state or enter a target state, it may be modified (e.g. such as by varying one or more of the variable parameters), discontinued, or a second transcutaneous vibratory output may be generated and commenced.

Methods and systems disclosed herein are directed at assisting a subject to reach a target state using their sensory thresholds, both lower and upper, as bounds for the transcutaneous vibratory output that is generated. When an input a state is made to a processor in communication with a transducer, such as the user has a particular disorder, the transducer is caused to generate transcutaneous vibratory output in a selected pattern, based on the identified disorder, at a sensory threshold value at or above the subject's sensory threshold for transcutaneous vibratory output. Various values and ranges for perceived beat, perceived pitch and sensory threshold limitations are disclosed in the treatment of various hypoarousal and hyperarousal symptoms associated with imbalances in autonomic nervous system (ANS).

Methods and systems disclosed herein are directed at assisting a subject to reach a target state and storing at least one of contextual or biometric data of the user while the user is in the target state as a baseline state. For example, the user may desire stimulation to achieve a "pumped state" (optimal performance state), and may indicate so in a user interface, and a transcutaneous vibratory output may be generated to achieve the state. When the user achieves the state, such as by their indication of so achieving in a user interface or by their turning it off, biometric and contextual data are stored for the future. Perhaps the contextual data includes the user's location at a gym. If this location is sensed again by a processor in communication with the transducer, the transcutaneous vibratory output that was generated to achieve the "pumped state" may be automatically commenced.

Systems disclosed herein are configured to assist a subject to reach a target state using a coordinated system of transducers. Each transducer in the system emits a transcutaneous vibratory output in accordance with a desired target state of the user, where each transducer emits one of the wave pattern for perceived pitch or the wave pattern for perceived beat, or each transducer in the system emits a different transcutaneous vibratory output in a pattern (e.g simultaneously, sequentially, alternating, coordinated). Each transducer in the system may be worn on a different body part. As with all embodiments herein, if the transcutaneous vibratory output emitted by any of the transducers is not effective to assist the user to enter a target state, it may be modified (e.g. such as by varying one or more of the variable parameters), discontinued, or a new transcutaneous vibratory output for one or more of the transducers may be generated and commenced. In some embodiments, the processor of a first transducer is programmed to modify the transcutaneous vibratory output pattern based on data received from a second transducer. As with any of the embodiments herein, the processor of the transducer may be in communication with one or more sensors, with other systems, devices, or transducers and any processor thereof, or with a remote server.

Methods and systems disclosed herein are directed at assisting a subject to reach a target state using transcutaneous vibratory output and another modality (e.g. a sensory stimulation (e.g. visual, olfactory, tactile, etc.), a therapy (e.g. psychotherapy, physical therapy, massage)). Based on a condition of the user, determined automatically via sensing (e.g. physiological, biometric) or input by a user, a transcutaneous vibratory output is generated to assist in resolving the condition. Further, a sensory stimulation may be selected based on the assessed condition of the user or the vibratory output selected. The sensory stimulation may further be commenced by a processor in communication with a controller of a system or sensory output device delivering the sensory stimulation. In some embodiments, the sensory stimulation is applied with the stimulation device.

Methods and systems disclosed herein are directed at assisting a subject using transcutaneous vibratory output to mitigate the negative effects of a drug (e.g. MDMA, psilocybin, *cannabis*, an anti-depressant, an anti-anxiety drug, an anti-psychotic, and a psychoactive drug) in the treatment of a mental health condition. Methods may include administering a drug to the subject in a therapy session and identifying any effects that are counterproductive to the therapy session (e.g. anxiety, restlessness). If any are identified, such as by a therapist input, a sensor (e.g. physiological or biometric), or by user input, a transcutaneous vibratory output and/or variable parameters used to generate the vibratory output may be selected that mitigates or reduces the negative effects. The vibratory output may be generated and applied. A sensory stimulation may also be applied to the subject, by the subject, in response to identification of any negative effects.

Methods and systems disclosed herein are directed at providing transcutaneous vibratory output for a therapeutic session based on an event to be experienced by a user. Data regarding the event may be obtained through input on a user interface or through communication of the event to a processor that creates therapeutic session parameters. Based on the event, the processor may assign a set of contiguous output segments to the event and instruct a transducer, or send a processor in associate with the transducer instructions, to generate the segments, whereupon the transducer generates the segments. The therapeutic session may be further modified in accordance with the event. The event may be at least one of an athletic event, an entertainment event, a psychotherapy session, or a stress inducing event, and the data regarding the event may be based on location, received from a traffic application, collected by a physiological sensor, is a change in the event, a change in a traffic pattern. Methods may further include administering a drug during the psychotherapy session.

Methods and systems disclosed herein are directed at assisting a subject to sleep using transcutaneous vibratory output. During transcutaneous vibratory stimulation intended to prime the user to enter a sleep state, a physiological sensor worn by or near the user provides data to a processor in communication with a transducer regarding if the subject is in a pre-sleep state or a sleep state, and based on the data, the processor may alter one or more variable parameters of the stimulation pattern emitted by the transducer or power off the transducer. In embodiments, certain variable parameters may be tapered down if the data indicate the user is close to sleep or already sleep. Tapering down may include reducing the frequency of the perceived pitch and/or increasing the interval of the perceived beat and/or reducing the intensity and, optionally, maintaining the reduced frequency and/or increased interval and/or reduced intensity for a period of time. In some embodiments, the therapeutic stimulation pattern includes two or more oscillations, one in a range of approximately 1 to approximately 100 Hz, and the other initially differs from the first frequency by approximately 0.0001 to approximately 1 Hz, that collectively form a beat output.

Methods and systems disclosed herein are directed at assisting a subject to reach a target state using transcutaneous vibratory output. A processor at least one of within or in electronic communication with a mobile device is in electronic communication with a transducer and a sensor sensing biometric data of the user. The transducer receives a target state for a user and generates a first transcutaneous vibratory output. Biometric data are received from the sensor and a determination is made by the processor if the user has at least one of achieved or not achieved the target state, and if the user has not achieved the target state, the processor is further programmed to determine the user's current state. The mobile device is caused to (i) generate output indicating whether the user has achieved the target state, and (ii) if the user has not achieved the target state, generate output (e.g. visual, audible, or tactile) to guide (e.g. pulsing heart, a depicted breathing rhythm) the user to achieve the target state.

Methods and systems disclosed herein are directed at assisting a subject to reach a target state using transcutaneous vibratory output delivered through or by furniture. A system may include a housing comprising a seat/seat back that includes a transducer. A physiological sensor may determine a state of alertness of the occupant of the seat and the processor may control the transducer in response, such as to cause a stimulation that is directed at causing wakefulness in a user. A vehicular sensor may sense a vehicle operation parameter (e.g. vehicle motion, windshield wipers activated) wherein the processor may use the vehicle operation parameter to control the transducer.

Methods and systems disclosed herein are directed at assisting a subject to reach a target state using transcutaneous vibratory output delivered through or by an infant seat. The infant seat comprises a transducer located at least partially within the housing and adapted to deliver a vibratory stimulation to an occupant (e.g. an infant) of the seat. A microphone may sense an utterance from the infant and transmit it to a processor using a data transmitter. The processor may be located remotely from the housing or in the housing itself. An indicator may be adapted to respond to a signal from the processor to provide an output, such as through a mobile device display or a display on the infant seat. The processor may determine a beginning utterance volume and duration and a current volume and duration and determine a magnitude of difference between the values and generate a signal indicative of whether additional vibratory stimulation is needed, and optionally, a duration or intensity of the vibratory stimulation. The signal may be transmitted to one or more processors associated with the system. The processor may further cause the transducer to generate a transcutaneous vibratory output.

Methods, systems, and kits disclosed herein are directed at causing an epigenetic change using transcutaneous vibratory output. An epigenetic marker is measured in the user, wherein the epigenetic marker is at least one of a regulation of a protein or a gene or a methylation, acetylation, or phosphorylation status of a gene or a histone. A transcutaneous vibratory output is provided to a user, optionally repeatedly, which is directed at causing a user to achieve a target state, then the measurement of the epigenetic marker is repeated to identify a change in an aspect of the epigenetic marker as a result of subjecting the user to the first transcutaneous vibratory output or a series of vibratory outputs over time. Target state achievement may be verified by a physiological sensor and/or user input. The transcutaneous vibratory output may be continued, altered, or terminated in response to data regarding the epigenetic marker. In place of measuring the epigenetic marker, a proxy for an epigenetic change may be measured, such as a stress indicator. The stress indicator may be a presence, an absence, or a frequency of one or more positive or negative words in communications or social media postings. The stress indicator may be a vocal tone, a pitch, and a vocal rate, a time to reach the target state after continued use, or a dwell time in the target state after continued use. A kit may comprise the stimulation device, a physiological sensor and a user interface, and may further comprise a biological sample collection device, wherein the user is prompted, through the user interface, to provide a biological sample for epigenetic change testing if the indication is that the user has achieved the target state.

Methods and systems disclosed herein are directed at assisting a subject to reach a target state using dynamic transcutaneous vibratory output to prevent habituation. Preventing habituation may include tapering or ramping a transcutaneous vibratory output that is generated and applied to a user to assist them in reaching a target state. With each subsequent execution of a session, any of the tapering rate, ramp rate, highest value or lowest value may be modified in order to prevent habituation. Further, the tapering or ramping may involve tapering or ramping one or more different variable parameters during subsequent executions of the session. In other embodiments, the initial transcutaneous vibratory output used for subsequent executions of the session may comprise at least one variable parameter that is different from those used in the previous session.

Methods and systems disclosed herein are directed at determining a user's sensory threshold for transcutaneous vibratory output. A lower sensory threshold is established by delivering a transcutaneous vibratory output to a portion of a user's body and gradually reducing an intensity of the transcutaneous vibratory output until the user indicates, such as on a user interface, that it is barely noticeable, and then delivering subsequent transcutaneous vibratory output, such as to assist a user in reaching a target state, at or within a desired standard deviation of the lower sensory threshold. An upper sensory threshold is established by delivering a transcutaneous vibratory output to a portion of a user's body and gradually increasing an intensity of the transcutaneous vibratory output until the user indicates that it is distracting, and then delivering subsequent transcutaneous vibratory output, such as to assist a user in reaching a target state, at or within a desired standard deviation of the upper sensory threshold. In some embodiments, establishing a sensory threshold is done by delivering a transcutaneous vibratory output to a user and providing a user interface for a user to adjust the perceived intensity, such as to a point where it is barely noticeable or distracting. The user interface may provide prompts to guide the user through the adjustments in establishing the sensory threshold. A final value of the perceived intensity is stored after the user completes adjustment, wherein the final value is the sensory threshold.

Methods and systems disclosed herein are directed at assisting a subject to reach a target state using transcutaneous vibratory output that tapers down or ramps up. A value of one or more of the first perceived pitch, the first perceived beat, and the first perceived intensity of the transcutaneous vibratory output is at an upper value. One or more of the first perceived pitch, the first perceived beat, and the first perceived intensity are tapered down to a lower value over a first period of time and, optionally maintained or discontinued when reaching the lower value. Tapering may be done using a first tapering rate to reach one or more intermediate values between the highest and lowest values, wherein multiple rounds of tapering and maintaining may be done between the highest and lowest value. Other tapering rates may be used between intermediate values and between intermediate values and the lowest value. In ramping up, a value of one or more of the first perceived pitch, the first perceived beat, and the first perceived intensity of the transcutaneous vibratory output is at a lower value. One or more of the first perceived pitch, the first perceived beat, and the first perceived intensity are ramped up to a higher value over a first period of time and, optionally maintained or discontinued when reaching the higher value. Ramping up may be done using a first ramping rate to reach one or more intermediate values between the lowest and highest values, wherein multiple rounds of ramping and maintaining may be done between the lowest and highest value. Other ramping rates may be used between intermediate values and between intermediate values and the highest value.

Methods and systems disclosed herein are directed at assisting a subject to reach a target state using transcutaneous vibratory output include controlling external devices based on state achievement, such as determined by a sensor, user input, or third party data, or in order to achieve a state. A target state of the user is determined and transcutaneous vibratory output is generated and applied to a user. An action related to control of an external device is caused to at least one of facilitate entry into the desired target state or in response to reaching the desired target state. The action may be adjusting a parameter of an environment or a device, such as turning off/on lights, changing room temperature, lowering/raising window shades, turning on/off music, triggering a secondary stimulating device in a mattress/pillow/seat, triggering an aromatherapy, or triggering a particular color. The action may be adjusting at least one of a content delivery setting or a content filter for applications and communications, wherein the content filter determines the types of content delivered to the user. The action may be adjusting a social media setting, such as a do not disturb setting. The action may be prompting the user to perform a certain a task.

Methods and systems disclosed herein are directed at assisting a subject to reach a target state using audible vibratory output. Upon obtaining input of a target state or determining the need to achieve a target state based on sensors or third party data, an audible output is generated and delivered to the subject to assist the subject in achieving the target state, the audible output having variable parameters comprising variable parameters including a perceived pitch, a perceived beat, and a perceived intensity. As with the transcutaneous vibratory output, a user or a processor may be able to adjust any one of the variable parameters, cause the output to be dynamic, taper, ramp, discontinue or maintain the output, calibrate the output, establish sensory thresholds for audible output, and other methods and systems described herein. In embodiments, the audible output may comprise multiple segments, each optionally having different values for perceived pitch, perceived beat, and intensity. In some embodiments, the audible output may be accompanied by transcutaneous vibratory output.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIGS. 2A and 2B depict block diagrams of a stimulation device.

DETAILED DESCRIPTION

Figure 1:
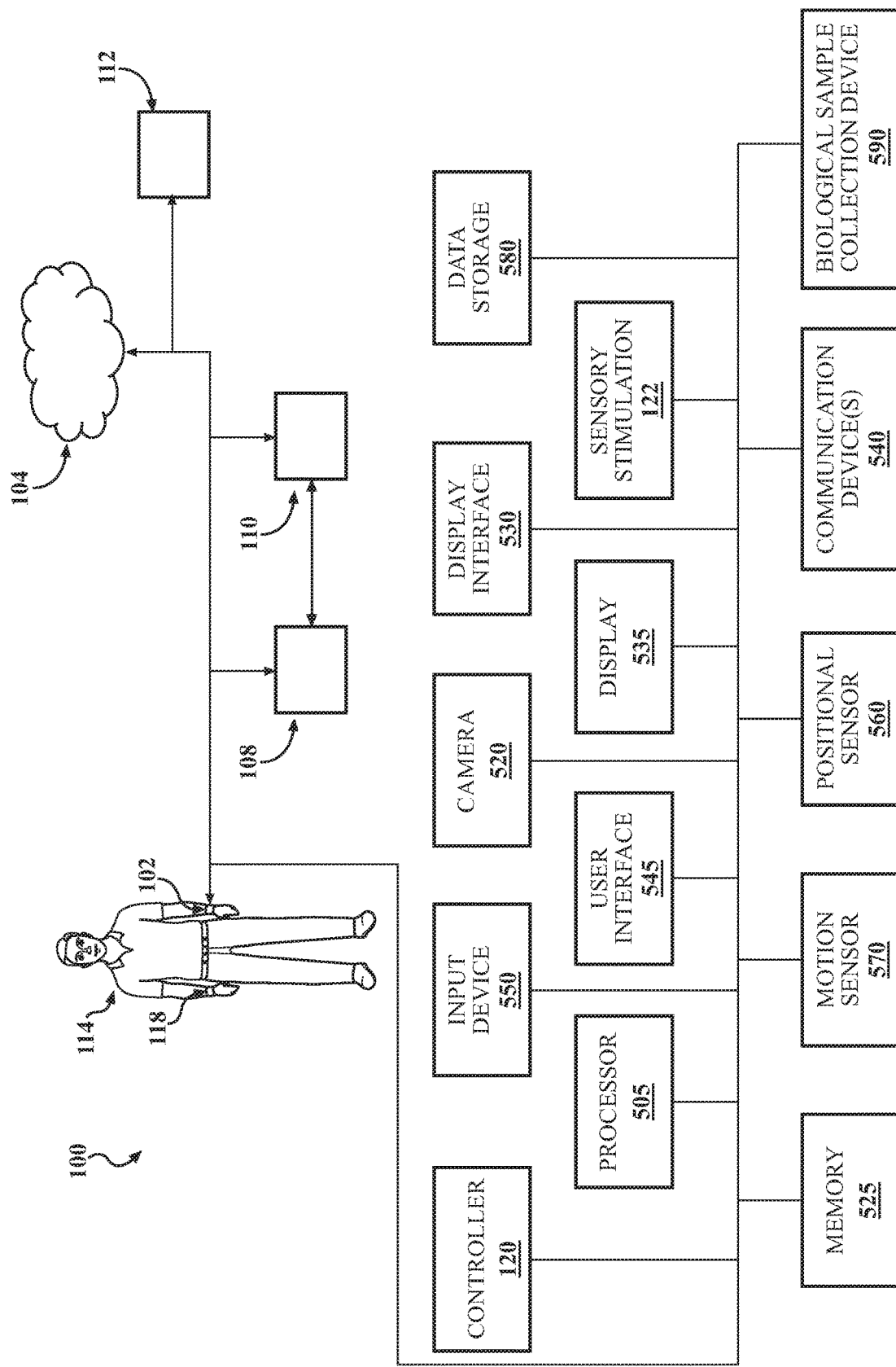
FIG. 1 depicts a system for facilitating neural state transitions.

An apparatus with transducers may deliver stimulation and/or treatment to a portion of a subject, such as in response to an input, that is intended to allow the subject to achieve a target state, such as a neural state. Such "stimulation" will be described herein more fully. However, the stimulation shall be briefly referred to here as transcutaneous vibratory stimulation. However, individuals reside in ecosystems with many inputs, devices, and sources of stress such that achieving and maintaining any one state, recovering from states, or being resilient to certain states, such as stress, may be difficult. This apparatuses, methods and systems described herein provide solutions to certain problems, such as how to: mitigate the negative effects of co-treatment with a stimulation protocol, predict a particular neural state onset and treat proactively with particular waveforms, utilize data external to the apparatus to determine a subject's state and/or achievement of a target state post-stimulation/treatment, learn a user's stimulatory preferences and needs to generate a stimulation/therapy plan, determine a user's sensory threshold, develop protocols to avoid habituation to stimulation or stimulation patterns, taper or ramp up a stimulation protocol, fine tune the stimulation necessary to achieve a target state based on real-time or longitudinal data, program the device to deliver patterns/sessions of stimulation, facilitate entry into a sleep state, provide visual feedback to a user of a state and/or a treatment protocol to facilitate entry into a state, coordinate stimulation from a plurality of transducers, control external devices based on aspects of the stimulation therapy, provide a meditation/mindfulness application, provide stimulation therapy to a user via any connected hardware, provide stimulation therapy in various products (e.g. seat/furniture, mobile seat, gaming seat, infant seat or other furniture, cradle/bassinet/ crib, bedding, wearable/garment, eyewear, augmented reality eyewear, wearable pet product, gaming/entertainment devices), provide haptic protocols of multiple frequencies, provide treatment using audible frequencies, provide the transducers as a component of another device (e.g. in a clasp/portion of a smartwatch band that is communicatively coupled to a smartwatch or other device), measure and track epigenetic changes as a result of treatment, or the like. Certain solutions described herein are directed to solving the aforementioned problems.

Terminology that is relevant to this document includes the following:

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

In this document, when terms such as "first" and "second" are used to modify a noun, such use is simply intended to distinguish one item from another, and is not intended to require a sequential order unless specifically stated. The term "approximately," when used in connection with a numeric value, is intended to include values that are close to, but not exactly, the number. For example, in some embodiments, the term "approximately" may include values that are within +/−10 percent of the value.

When used in this document, terms such as "top" and "bottom," "upper" and "lower", or "front" and "rear," are not intended to have absolute orientations but are instead intended to describe relative positions of various components with respect to each other. For example, a first component may be an "upper" component and a second component may be a "lower" component when a device of which the components are a part is oriented in a first direction. The relative orientations of the components may be reversed, or the components may be on the same plane, if the orientation of the structure that contains the components is changed. The claims are intended to include all orientations of a device containing such components.

An "electronic device" or a "computing device" refers to a device or system that includes a processor and memory. Each device may have its own processor and/or memory, or the processor and/or memory may be shared with other devices as in a virtual machine or container arrangement. The memory will contain or receive programming instructions that, when executed by the processor, cause the electronic device to perform one or more operations according to the programming instructions. Examples of electronic devices include personal computers, servers, mainframes, virtual machines, containers, gaming systems, televisions, digital home assistants and mobile electronic devices such as smartphones, fitness tracking devices, and wearable virtual reality devices. Electronic devices also may include Internet-connected wearables such as smart watches, smart clothing and smart eyewear. Electronic devices also may be embedded in products that are designed to be used by a human while sleeping, such as a pillow, mattress, mattress topper or bedding (sheets, pillowcase, blanket, etc.). In a client-server arrangement, the client device and the server are electronic devices, in which the server contains instructions and/or data that the client device accesses via one or more communications links in one or more communications networks. In a virtual machine arrangement, a server may be an electronic device, and each virtual machine or container also may be considered an electronic device. In the discussion below, a client device, server device, virtual machine or container may be referred to simply as a "device" for brevity. Additional elements that may be included in electronic devices will be discussed below in the context of FIGS. 1 and 2.

The terms "processor" and "processing device" refer to a hardware component of an electronic device that is configured to execute programming instructions. Except where specifically stated otherwise, the singular terms "processor" and "processing device" are intended to include both single-processing device embodiments and embodiments in which multiple processing devices together or collectively perform a process.

The terms "memory," "memory device," "data store," "data storage facility" and the like each refer to a non-transitory device on which computer-readable data, programming instructions or both are stored. Except where specifically stated otherwise, the terms "memory," "memory device," "data store," "data storage facility" and the like are intended to include single device embodiments, embodiments in which multiple memory devices together or collectively store a set of data or instructions, as well as individual sectors within such devices.

As used herein, the term "treat", "treating" or "stimulating" refers to improving the mood and/or physiology and/or symptoms of a subject, including enhancing a person's positive outlook or suppressing a person's negative outlook. Such may refer to a person's psychological well-being, including but not limited to their emotional, cognitive, and motivational states.

The term "depression" refers to a morbid sadness, dejection, or melancholy, and includes general physical conditions in which a person exhibits symptoms such as sleep problems, appetite problems, anhedonia or lack of energy, feelings of worthlessness or hopelessness, difficulty concentrating, and suicidal thoughts.

As used herein, the term "side effect" refers to undesirable physiological and/or psychological effects of a medical treatment on a subject. Side effects may be reduced by decreasing their severity, by decreasing their frequency, or by decreasing both their severity and frequency. The stimulation of the autonomic nervous system by application of vibrational stimulus (as discussed herein) may reduce side effects from various medical treatments, including, without limitation pharmaceutical agents, drugs, *cannabis*, psychotherapy, surgical procedures, or the like.

Throughout this specification, the stimulation described is referred to as transcutaneous vibratory stimulation or transcutaneous vibratory output. One form of such transcutaneous vibratory stimulation or transcutaneous vibratory output may be haptic or tactile stimulation, wherein "haptic" and "tactile" may be used in the alternative. While in other embodiments, the stimulation (transcutaneous or not) may be audible (and thus experienced audibly by the subject). Such audible embodiments are designed to achieve a target state through the subject's hearing or audiation. All such stimulation may be referred to as "therapy" or "therapeutic output".

A "subject" may be referred to as a "user" or a "wearer" of the device. In some instances, there is a "subject", i.e., the person or organism to whom the vibratory stimulation is applied, and a "user" who may be separate from the subject.

Therefore, the user may be the subject or not depending on the context of the description or the accompanying claims.

In embodiments throughout this disclosure, and as will be further described herein, a system for treating a subject may include a stimulation device that includes a tactile transducer configured to emit transcutaneous vibratory output to a portion of the subject's body in communication with a processor. The system may optionally include a sensory output device, also in communication with a processor. The processor may be in communication with a memory that has instructions stored thereon that when executed cause the processor to determine a transcutaneous vibratory output and, optionally, a sensory output, wherein the processor causes the tactile transducer to emit a transcutaneous vibratory output determined by the processor, the transcutaneous vibratory output comprising a perceived pitch and a perceived beat. An application in communication with the processor may receive data from the stimulation device and embedded or associated sensors and devices, and may further control the stimulation device and embedded or associated sensors and devices. In embodiments, the processor may optionally cause the sensory output device to output at least one of a visual, an olfactory, or an audible output. The system may also include one or more sensors, such as a physiological sensor or a biometric sensor generating data indicative of a condition of the user, wherein the processor is further configured to determine a transcutaneous vibratory output or a sensory output based on the data indicative of a condition of the user.

The system may include controllers, processors, network infrastructure, cloud-based storage, input/output devices, servers, client devices (e.g., laptops, desktops, terminals, mobile devices, and/or dedicated devices), sensors, actuators, data storage or subscriptions, and/or components configured as computer-readable instructions that, when performed by a processor, cause the processor to perform one or more functions. The system may be distributed across a number of devices, including wearable devices, and/or the functions of the system may be performed by one or more devices in cooperation.

The system may include application programming interfaces that facilitate connection among the components of the system and between the system to entities that are external to the system and facilitate operation, programming, and use of the system by a user. Any component or interface to the system may be controlled by or have control over a controller. In some embodiments, a mobile device being operated by a user may form a portion of the system as described herein.

Certain considerations for the person of skill in the art, in determining the configuration of components, circuits, controllers, and/or devices to implement the system as described herein include, without limitation: the availability of sensed or collected data; a communication status with one or more sensors; the knowledge of one or more sensory thresholds; the proximity of a suitable transducer to a portion of a user's body; the availability of a suitable transducer; if instructions are to be provided directly by a user or if the system is to be triggered; if another treatment modality is being used concomitantly (e.g. pharmacological, sensory, or therapeutic), or the like.

While specific examples of the system and considerations are described herein for purposes of illustration, any system benefiting from the disclosures herein, and any considerations understood to one of skill in the art having the benefit of the disclosures herein, are specifically contemplated within the scope of the present disclosure.

Referring now to FIG. 1, an embodiment of a system for facilitating neural state transitions is depicted. In the system, a stimulation device 102 may be programmed to provide acoustic and/or vibrational energy, such as tactile, haptic, or transcutaneous vibratory energy, that may be transmitted to a subject 114 wearing the therapeutic device. The stimulation device 102 may be an apparatus with a transducer adapted to deliver a stimulation to a portion of a subject intended to allow the subject to achieve a state. In certain embodiments, the stimulus may comprise oscillations of different frequencies, such as sine wave oscillations, that results in a beat frequency that is output to the subject. In an embodiment, the stimulation device may be configured, via a processor, to generate a transcutaneous vibratory output to assist a user in achieving a target state, the transcutaneous vibratory output comprising a first perceived pitch, a first perceived beat, and a perceived intensity. The stimulation device 102 may be controlled directly through a user interface of the stimulation device 102, such as through a controller 212, or may be controlled through an application executing on a mobile device or computing device. In embodiments, remote servers or applications running in the cloud 104 may be used to control, configure or otherwise communicate with a processor of the stimulation device 102. I/O devices 110 (e.g. third-party devices or software) may be used to provide data for processing by the stimulation device 102 and/or associated applications or systems. Likewise, the stimulation device 102 may provide and/or transmit data to I/O devices 110. Mathematical analysis of the collected data from all available sources may be performed by a processor of the stimulation device 102 or application/remote server in communication with the stimulation device to, among other things, generate predictions of a state transition. External devices/systems 108, such as a mobile phone or application (e.g. care provider application) may be used to control the stimulation device 102 or may in turn be controlled by the stimulation device 102 or its output. Any of the system components may be in communication with each other via the cloud, directly or by some other relay. The system may include a remote server 112, wherein the stimulation device 102 may communicate with the remote server 112 to receive data, instructions, programming or firmware updates, and the like.

Sensors 118 may be external to or integrated with the stimulation device 102 and may be used to obtain feedback from the user before, during, or after the stimulation device's 102 operation, may be configured to collect biometric, physiological, movement, and/or contextual data from the subject 114 or the subject's environment to be used to determine the state of the subject, provide data useful for altering a vibratory output, establish a baseline state of the subject, predict a user's future state, establish a sensory threshold, and in any of the other embodiments described herein. Sensor 118 readings may be used by the device and/or associated applications as feedback with which to potentially alter the pattern, frequency, intensity and/or duration of transcutaneous vibratory output (or audible output, as the case may be), as will be further described herein. Physiological sensors may measure ECG, temperature, heart rate, heart rate variability (e.g. which is a proxy for autonomic nervous system tone and emotion regulation capability), respiration rate, blood volume pulse, blood pressure, transcutaneous cortisol, blood glucose, vocal tone/pitch/vocal rate (e.g. such as with a microphone), galvanic skin response, gamma band EEG, pupil size/reactivity, brain activity (whole brain EEG), muscle activity, facial expressions, temperature, sweat amount, sweat components, cerumen components, or the like. Environmental sensors used to further assess user's state may include calendar activity, social media postings, screen time/phone usage, texting frequency, screen tap pressure, or game play frequency. Digital image frames may be received from an imaging sensor (e.g. camera) that can capture video and/or still images, wherein the camera may be associated with the stimulation device or a separate device. The system also may include a positional sensor 560 and/or motion sensor 570 to detect position, movement, activity or location of the user or stimulation device. The positional sensor 560 and/or motion sensor 570 may be worn by the user or in a device carried by the user. In embodiments, motion sensors 570 may include gyroscopes or accelerometers. In embodiments, positional sensors 560 may include a global positioning system (GPS) sensor device that receives positional data from an external GPS network. Contextual data, which may be used in any of the disclosed embodiments, may derive from content of social media, a navigation application, a calendar application, a movement tracker, location tracker, direction of travel, an amount of usage of the mobile device, keystrokes input into the mobile device, or a project management application. Data collected by any of the sensor devices described herein that may be used to modify an aspect of the stimulation, discontinue the stimulation, or otherwise be used in a feedback loop. The sensor device may be embedded in a sensing wearable device such as a watch, wristband, bracelet, shirt, medical device (e.g. blood pressure cuff, pulse ox, thermometer, light stimulation, sound stimulation), exercise/activity monitor, or other wearable item. Alternatively, or in addition, a sensor device may be embedded in a separate device that is touching or proximate to the user, such as a pillow, mattress, blanket or other bedding.

The stimulation device 102 may be configured to provide acoustic and/or transcutaneous vibratory stimulation to the subject 114 and may be configured to modulate the autonomic nervous system. In various embodiments, the stimulation device 102 may be configured to apply the stimulation to one or more body parts of the subject 114 by being worn or placed in proximity to, without limitation, the human's wrist, ears, neck, ankles, hips, knees, feet, sternum, chest, back, whole body, or the like. In certain embodiments, the stimulation device 102 is adapted to be disposed in a portion of a subject, such as by implantation, to deliver a stimulation, such as through implantation of the device 102 or when the device 102 is integrated with another implantable, such as an insulin pump, pacemaker, or the like. Thus, the parts of the stimulation device 102 that emit vibrations may be included in the form of a wearable device such as a band that wraps around the appropriate body part (wrist, ankle, head, feet, etc.), a set of headphones or earbuds, a hat or cap, a wristwatch, a shirt, or other wearable devices, or an implantable device. In some embodiments, the stimulation device 102 must be touching the body to be effective, while in other embodiments, the stimulation device 102 is effective without having to actually contact the body.

Figure 3:
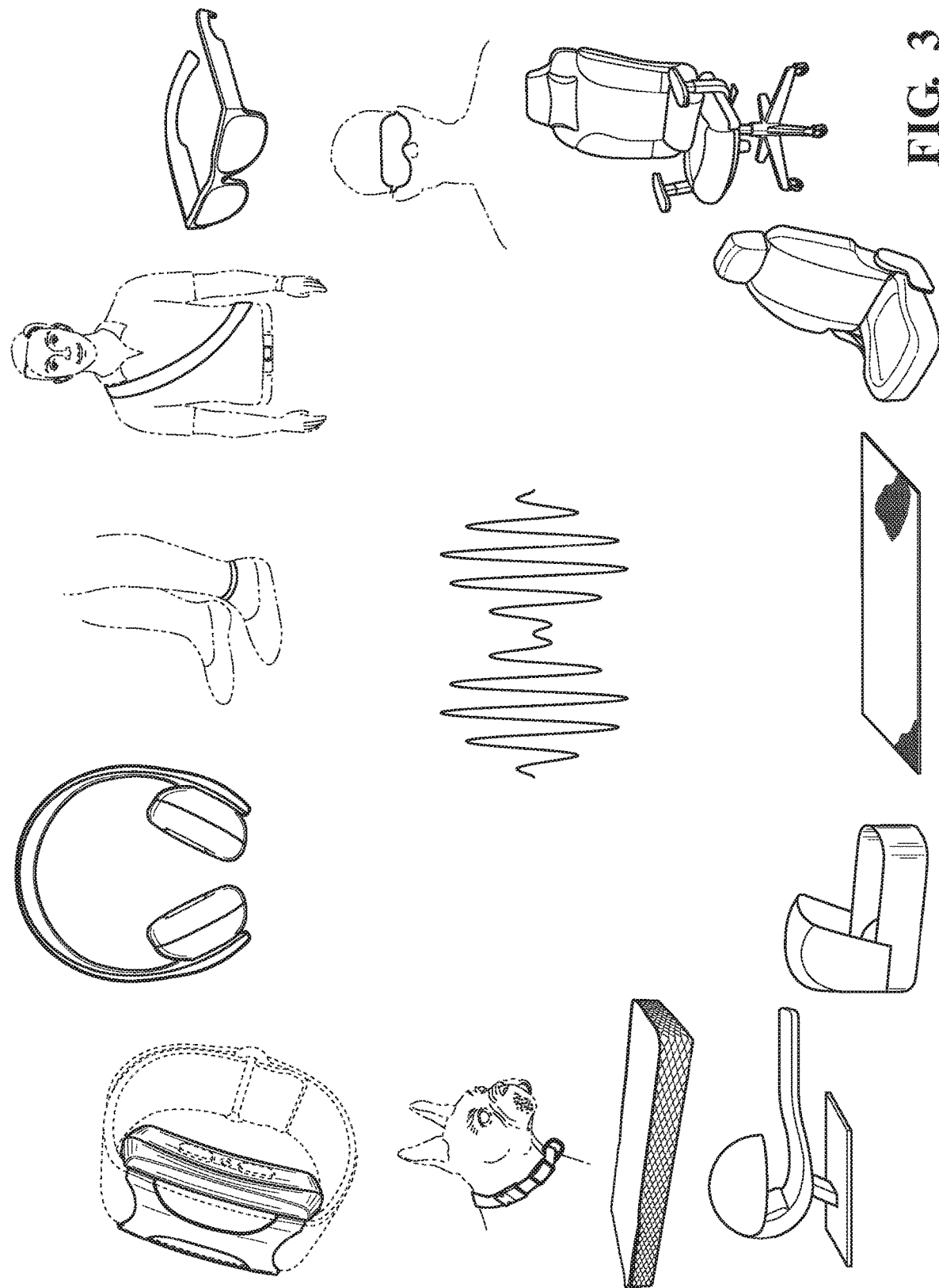
FIG. 3 depicts various embodiments of devices that provide stimulation.

In an embodiment, and referring now to FIG. 3, the stimulation device 102 may be embodied in a wearable (which may be Internet-connected), a watch, a smart watch, a smart phone, a computing device, an anklet, a chest strap, a smart clothing/garment (hat/shirt, scarf, earmuffs, hair band), a shoe/shoe sole/shoe insert, headphones/earbuds/earpiece (e.g. audio stimulation through earpiece), a smart eyewear, an eye mask, a seat, an infant seat/cradle/furniture, a vehicle seat with sensors in dashboard/seat/wheel, a pillow, a bed, a mattress, a mattress topper or bedding (e.g. sheets, pillowcase, blanket, weighted blanket, animal blanket etc.), a yoga mat, a pet product, a dog bed, a pet collar, a ready-made pod, or other clothing or furniture where the sensors and transducers/stimulators can be disposed or embedded. For example, a system to soothe an infant may include a seat with at least one strategically-placed transducer (e.g. cushion, mattress, mattress topper, bedding, pillow, stuffed animal) adapted to emit vibration comprising a perceived pitch, perceived beat, and a perceived intensity selected to induce a soothed state. For example, the system may be embodied in bedding, such as a mattress topper or pillow, wherein the system may deliver therapeutic stimulation to facilitate sleep, including taper functionality and/or sleep detection-turn-off functionality. Sensors may also be embedded in the bedding to track entry and/or exit from sleep, provide feedback on the effectiveness of the stimulation (e.g. respiration changing, cries diminishing), or to provide a signal to commence stimulation (e.g. microphones detecting a cry). A speaker may be included to play lullabies, heartbeat sounds, white noise, or other soothing output. In another example, a system may include a transducer located in a seat or seat back, such as an immobile seat or one in a transportation setting, wherein the transducer is configured to deliver a transcutaneous vibratory stimulation to an occupant of the seat. A physiological sensor may be used determine a state of alertness of the occupant of the seat and a processor may control the transducer in response. Where the seat is in an automobile, a vehicular sensor may sense a vehicle operation parameter, wherein the processor further utilizes the vehicle operation parameter to control the transducer. For example, if the vehicular sensor indicates that the user is closing their eyes while the car is still in motion, a processor in communication with a transducer in the seat may cause it to turn on and deliver stimulation directed at wakefulness. In yet another example, a pet or animal collar may have an embedded transducer and processor, wherein the processor can be remotely controlled by a separate device or an application executing on a smartphone, mobile device, computer, or the like to deliver stimulation through the transducer, as described herein, to an animal wearing the collar. Sensors, such as physiological sensors, microphones, cameras, or the like, may be integrated with the collar or associated with it to provide feedback, as described herein, to the processor. In any of the embodiments, control of generating and delivering the stimulation may be through the embodiment itself using firmware embedded in an integrated or associated processor, or may be through software or an API executing on a computing facility.

In an example, when the stimulation device 102 is embodied in a smart phone, an application on a smart phone computing device may be used to control it to emit stimulation, either as transcutaneous vibratory output, audible output, or both. The stimulation may be generated by one or more of a vibratory motor or speaker of the smartphone. In embodiments, other content may be delivered by the smart phone or other apps may be used to cause other actions or control other devices during the therapeutic output. In another example, the stimulation device 102 embodied in a ready-made pod may include modular parts or kits or parts sold to manufacturers of other products such as seats, sleeping PODS, baby seats, pet collars, and the like to be incorporated into designs/products. API's and wireless connectivity could be a component of the ready-made pod sold to manufacturers to provide control options. In an embodiment, the stimulation device 102 may be embodied in augmented reality or virtual reality eyewear or other equipment associated with these embodiments. For example, a transducer may be incorporated to the arms of the eyewear so as to deliver tactile stimulation, and optionally, audible stimulation to the user. Stimulation that is both tactile and audible may be synergistic or complementary. In embodiments, the augmented reality eyewear may be programmed to deliver content in conjunction with the stimulation.

Figure 2A:
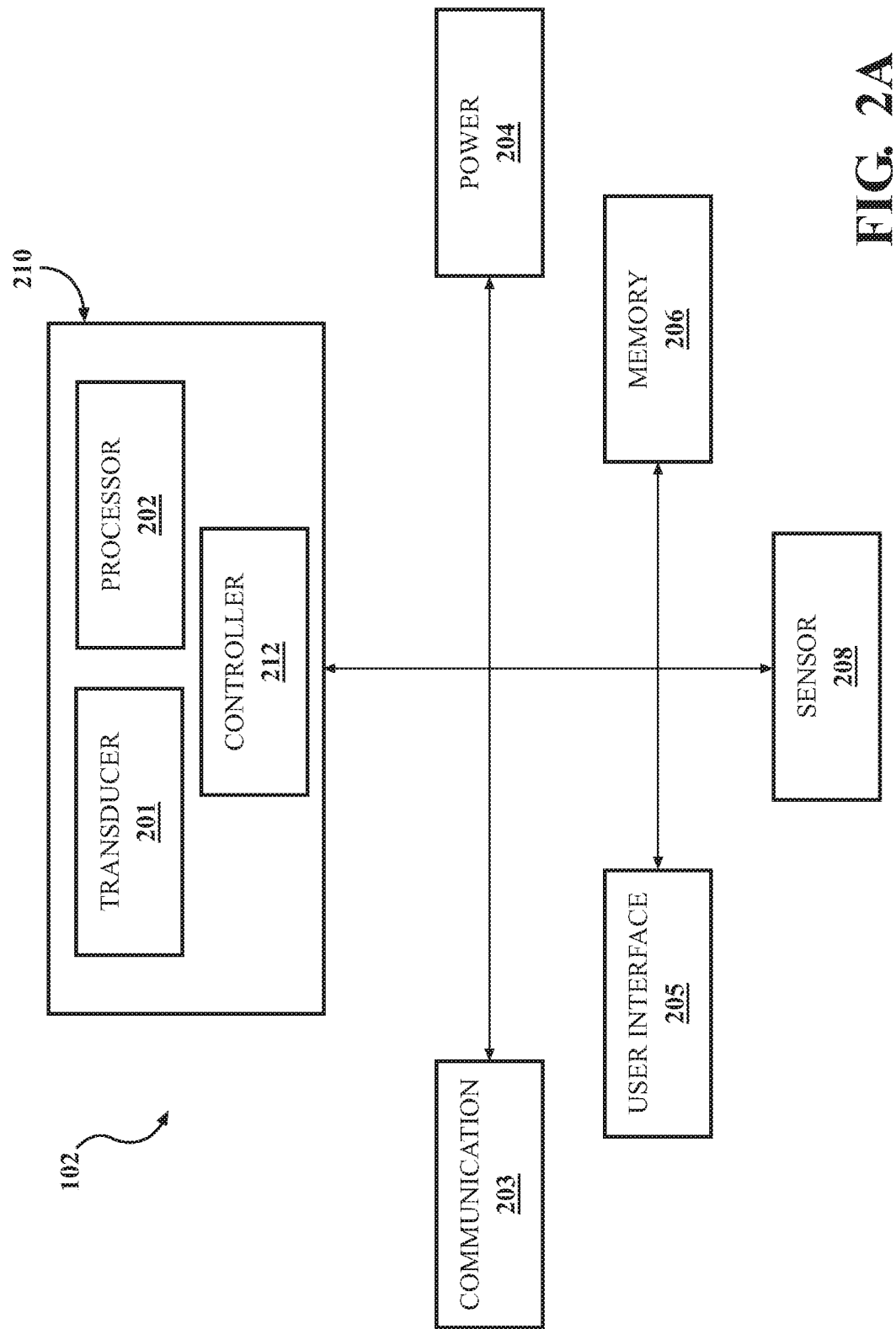

FIG. 2A and FIG. 2B illustrates a block diagram of an example stimulation device 102. As shown in FIG. 2A, the stimulation device 102 may include one or more transducers 201, a controller 212, and a processor 202 in a housing 210. The stimulation device 210 may be in communication with (as shown in FIG. 2A), or optionally include (as in FIG. 2B), a communications interface 203, a power source 204, an optional user interface 205, and a memory 206.

The one or more transducers 201 may be any device that may transmit vibrational and/or acoustic energy from an energy source to a subject in the form of stimulus. Examples of transducers may include, without limitation, bone conductors (e.g. such as a bone conductor in smart or augmented reality eyewear), tactile transducers, transcutaneous vibratory transducers, linear resonant actuators, rotational motors, bass shakers, or audio transducers (e.g., speakers). While not shown here, the transducer 201 may receive the desired stimulation signal from a driver that amplifies and filters it so that an appropriate voltage and current signal is applied to the transducer 201.

The processor 202 may be configured to control one or more functions of the stimulation device 102 such as, without limitation, application of a suitable stimulation to a subject, frequency control of the applied stimulation, processing of feedback received from the sensor device, communication with a user or an external system, or the like. In some embodiments, the processor 202 may be configured to control the stimulation applied (e.g., frequency, time duration, intensity, etc.) based on, without limitation, readings from the stimulation device 102, sensors 118, 208, 570, 560, user input, or any other information, or combinations thereof. The processor 202 may communicate with each of the other components of the stimulation device 102, via for example, a communication bus or any other suitable mechanism. The processor 202 may be controlled by an application executing on a mobile device, computing device or remote server 112.

In certain embodiments, the stimulation device 102 may be configured to apply the desired stimulation to a subject as transcutaneous vibration over a discrete period of time. In some embodiments, it may be a continuous application of frequency sound. The length of time during which the stimulation is applied may vary from situation to situation, depending on factors such as the nature and severity of the condition being treated: the size, age, gender, and overall condition (physical and psychological) of the subject, etc. Alternatively, and/or additionally, the duration may be defined based on input received from a sensor, the user, or third party data. In general, the duration of application may be in the range of 1 minute to two hours, and optionally in the range of 5-15 minutes or 1-5 minutes. Alternatively, a duty cycle by which the stimulation may be delivered may be an oscillating or pulsed manner e.g. by employing repeated sequences of seconds or minutes on and off, resulting in intermittent (for example, sporadic:30 seconds on-30 seconds off) or (for example non-sporadic: 30 seconds on-10 seconds off), alternating delivery and cessation of delivery of the therapeutic stimulation. In embodiments, the signal may be a series of discrete pulses with additional vibrations between pulses. The duty cycle may be programmed to result in staccato vibrations.

In one or more embodiments, a communications interface 203 may be configured to facilitate communication of data into and out of the stimulation device 102. In some embodiments, the communications interface 203 may include, without limitation, a WiFi transceiver, a Bluetooth transceiver, an RFID transceiver, an Ethernet port, a USB port, and/or or any other type of wired and/or wireless communication interfaces. The communications interface 203 may be configured to transmit data to and receive data from computing devices, mobile devices, and/or networks that are not included in the stimulation device 102. For example, communications interface may couple the stimulation device 102 to an application running on a user device such as a mobile device.

In certain embodiments, the user interface 205 may include any type of input and/or output devices that permit a user to input commands into or receive information from the stimulation device 102. The optional user interface 205 may include elements configured to receive commands or input parameters, or to be used to check or change settings. Examples include a tactile input such as a keypad or touch screen, a microphone, dedicated buttons, dials or switches, or other devise. In embodiments, the user interface 205 may be adapted to receive gestural input or verbal input.

The user interface 205 also may include elements configured to output data such as a display, light emitting diodes (LEDs), transcutaneous vibratory/haptic facilities, or an audio speaker. Output from the stimulation device 102 may be on a display of the device 102 itself, on a mobile device, on a third-party device, to an application such as a care provider application, or the like. In embodiments, the output may be visual feedback provided to the user in conjunction with delivered therapy. The processor may be in communication with a mobile device and a sensor sensing biometric data of the user, as well. During delivery of transcutaneous vibratory output to the user, the sensor may collect biometric data of the user. The processor may use the biometric data to determine whether the user has at least one of achieved or not achieved the target state, and if the user has not achieved the target state, the processor is further programmed to determine the user's current state relative to the target state. Based on these determinations, the processor then causes the mobile device to (i) generate output indicating whether the user has achieved the target state, and (ii) if the user has not achieved the target state, generate output to guide the user to achieve the target state.

In another embodiments, the visual feedback of the user's state may be provided on a display of the stimulation device itself. For example, a processor, either in the stimulation device or separate from it, may be in communication with the transducer and the display of the stimulation device and a sensor. The processor causes the transducer to generate a first transcutaneous vibratory output and then determines based on biometric data from the sensor whether the user has at least one of achieved or not achieved a target state, and if the user has not achieved the target state, the processor is further programmed to determine the user's current state relative to the target state. The processor may cause the display to display an indication of whether the user has achieved the target state, and if the user has not achieved the target state, display information to guide the user to achieve the target state. In other embodiments, the visual feedback of the user's state may be provided in an application executing on a smartphone, mobile device, computer, or the like.

In any of the embodiments, the output may be at least one of visual, audible, or tactile. For example, the visual output may be an image of a pulsing heart roughly mirroring the actual heartbeat of the individual. In embodiments, the pulsing heart may be configured to slow down or speed up in accordance with a sensed heart rate. The output to guide the user may be generated based on the user's current state relative to the target state. The output to guide the user may communicate a recommended breathing rhythm. If the processor determines that the user has not yet achieved the desired target state, the processor makes a determination that the output needs to be modified and causes the transducer to generate another transcutaneous vibratory output that may vary in one or more variable parameters relative to the first vibratory output.

The user interface 205 may permit a user to control the operation of the stimulation device 102, define settings (e.g., frequencies, intensity, time duration, etc.) of the stimulation device, receive information about operations of the stimulation device, troubleshoot problems with the stimulation device, or the like.

The system's user interface may include inputs that enable a user to activate and/or turn off the transducers, to modify stimulation patterns including modifying the herein described parameters of the output, and/or to indicate that a particular pattern is agreeable or not agreeable. The system may determine a user's usage pattern, such as patterns most frequently used and typical durations of usage, and save this data to a user profile so that the system can automatically adjust to the user's preferences. For example, if a particular therapy has a default duration and the user does not typically turn the therapy off before the end of that duration, the system may retain that duration when applying the therapy again. However, if the user typically turns the stimulation off before the default duration ends, the system may adjust the default duration for that user to match the average or mean duration that the user actually applies the therapy, optionally only considering a threshold previous number or times of application when calculating the mean or average. The system may also use other functions that are based on actual usage data to determine the duration. Similarly, a particular therapy may have a default intensity level, the user interface may permit the user to vary the intensity level, and the system may automatically adjust the default to match the user's mean or average selected intensity level.

In some embodiments, the power source 204 may be configured to provide power to the stimulation device 102. The power source 204 may include one or more of a rechargeable battery, a non-rechargeable battery, a solar cell, a chemical reaction power generator, a power input port that connects to an external power line, or any other device configured to provide power to the stimulation device 102 and its components.

The housing 210 may be configured to secure the transducer 201 at the site of application of the stimulation on a subject. For example, if the stimulation will be applied to the wrist of a subject, the housing may be in the form of a wristband. Similarly, if the stimulus will be applied to various points on the back of a subject, the housing may be a mattress, a mattress topper, a sheet or blanket, a wearable shirt, a seat or seat cushion, a body wrap, or other item that contacts the subject's back. Some components of the device such as the transducer 201 may be on or outside of the housing, or sonically conductive leads may extend from the housing from the transducer 201.

In some embodiments, audible frequencies may be delivered by the stimulation device itself, by a connected audio device, or in combination with tactile vibration. An application or other software may be used to control and/or cause to emit the audible frequency and/or vibration frequencies over the stimulation device or a peripheral device.

FIG. 1 also depicts various components that may be included in the system, either in the stimulation device or in a mobile device or computing device that is in communication with the stimulation device. In some embodiments, an electrical bus may provide for electronic communication among various components and a controller 120 may control such communications. Processor 505 may be configured to perform calculations and logic operations required to execute programming instructions. As used in this document and in the claims, the terms "processor" and "processing device" may refer to a single processor or any number of processors in a set of processors that collectively perform a set of operations, such as a central processing unit (CPU), a graphics processing unit (GPU), a remote server, or a combination of these. Read only memory (ROM), random access memory (RAM), flash memory, hard drives and other devices capable of storing electronic data constitute examples of memory devices 525. A memory device may include a single device or a collection of devices across which data and/or instructions are stored. The processor may be embedded in the stimulation device or may be in a separate device.

An optional display interface 530 may permit information to be displayed on a display device 535 in visual, graphic or alphanumeric format. An audio interface and audio output (such as a speaker) also may be provided. Communication with external devices may occur using various communication devices 540 such as a wireless antenna, an RFID tag and/or short-range or near-field communication transceiver, each of which may optionally communicatively connect with other components of the device via one or more communication system. The communication device 540 may be configured to be communicatively connected to a communications network, such as the Internet, a local area network or a cellular telephone data network.

In an embodiment, a user interface 545 may enable receipt of data from input devices 550 such as a keyboard, keypad, a mouse, a joystick, a touchscreen, a touch pad, a remote control, a pointing device, dedicated buttons, dials, switches, and/or microphone.

In an embodiment, the one or more transducers 201 may be configured to provide acoustic and/or vibrational energy as a wave pattern that may be transmitted to the subject, the acoustic and/or vibrational energy comprising the stimulation described herein, which is configured to cause a user to achieve a target state or maintain a current state. A phase accumulator or a numerically controlled oscillator may be used to generate waveforms. Data storage 580 may include data related to parameters for fundamental vibration generation, data related to treatment protocols including associated therapies and stimulation, data on how to interpret physiological and/or contextual data, data on endpoints used to trigger stimulation, user profile data including known physiological parameters, sensory thresholds, baseline states, performance states, typical locations, or the like, manually collected data from users, epigenetic data using data collected in part from a biological sample collection device 590, and data from monitoring mobile device and application usage, or the like. Parameters of fundamental vibration generation are frequency of the perceived pitch, frequency of the perceived beat, and intensity (or maximum intensity). The frequency of the perceived pitch defines a base (carrier) tone. The perceived beat frequency defines an envelope which modulates the amplitude of the base tone creating a fundamental vibration. This modulation involves multiplicative combination, as will be described herein. Intensity is then used when scaling the fundamental vibration for delivery via the transducers. In embodiments, the envelope is a sine wave whose frequency is half that of the perceived beat. Intensity correlates with the user's awareness of the stimulation, wherein the minimum necessary intensity is the point where the user becomes aware of the waves/vibrations and the maximum intensity is where the user no longer tolerates the stimulation. Developing the fundamental vibration via this approach has the benefit of augmenting the user experience by facilitating access to a variety of stimulation patterns. This approach also makes the generation of certain stimulation patterns, such as (i.e. taper, ramp, and/or intensity changes) far more efficient than it would be using interference patterns, including for example, by decreasing the processing needs to generate those stimulation patterns. The multiplicative approach to waveform generation improves the efficiency, in practice, of layering of additional frequencies over the use of interference patterns. For example, the most basic form of the waveform is one perceived pitch and one perceived beat, however, as discussed herein more than one perceived pitch and/or more than one perceived beat may be used to generate a waveform. The multiplicative approach described herein provides an improvement over an approach using interference patterns (also described herein) by making it far more efficient to layer, such as by, including more than one perceived pitch and/or more than one perceived beat. The improved efficiency of the multiplicative approach over an approach utilizing interference patterns is rooted in the fact that using more than two interference patterns results in high levels of unpredictability, due to the physics of combining frequencies. Complex interference patterns are unpredictable, and computationally inefficient, whereas the multiplicative approach described herein mitigates this concern. The multiplicative approach also provides enhanced user control over waveform generation, and ultimately the user's experience, by providing an enhanced means to adjust or select multiple variables and segments of vibratory stimulation.

Figure 4A:
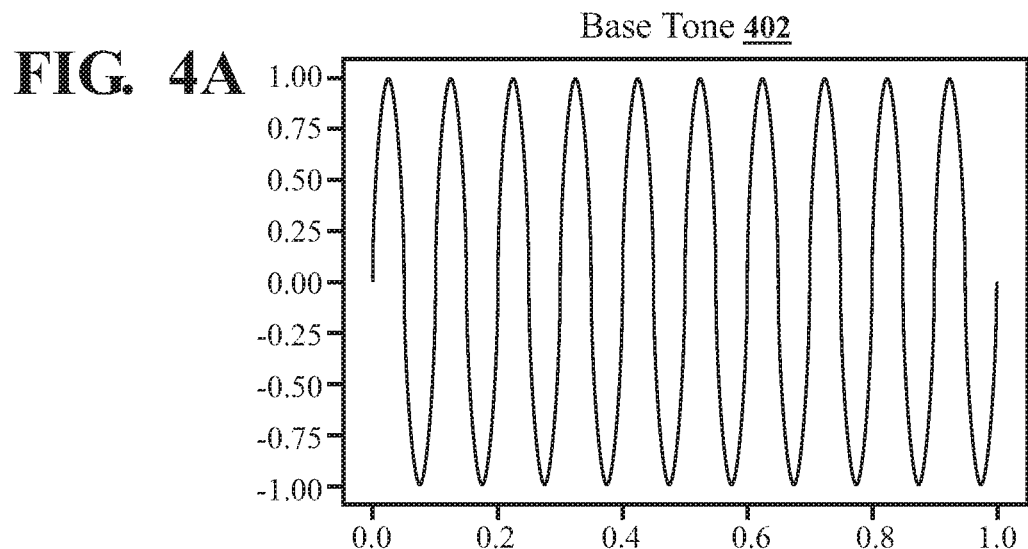
FIG. 4A depicts a wave pattern with a perceived pitch.
Figure 4B:
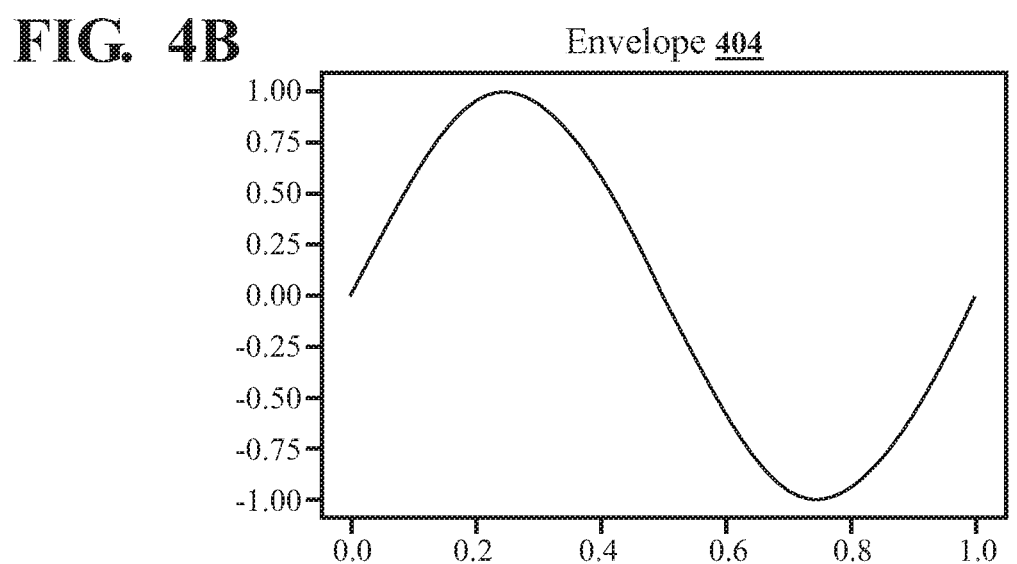
FIG. 4B depicts a sine wave-shaped envelope.
Figure 4C:
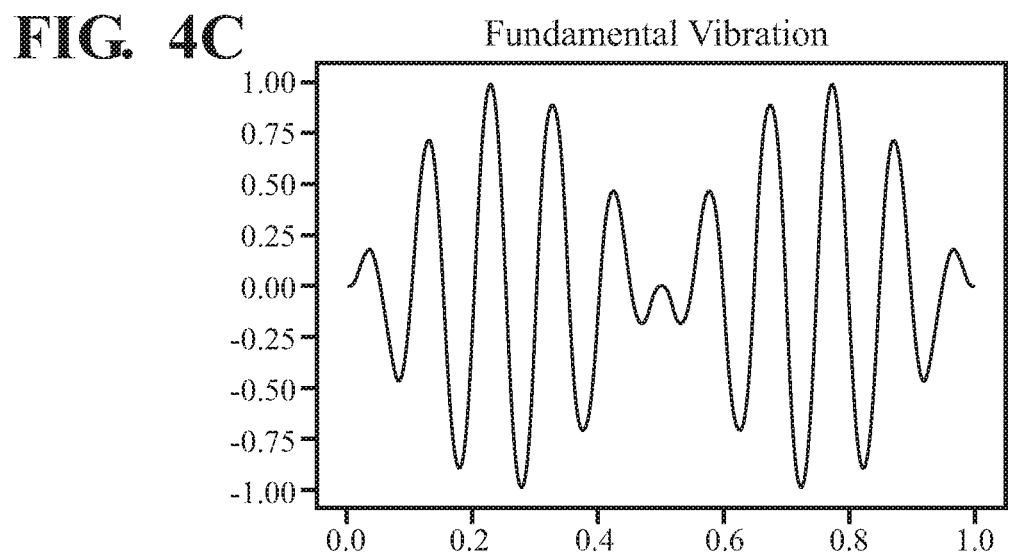
FIG. 4C depicts a waveform with the envelope, or beat, shown in FIG. 4B.

For example, the graph shown in FIG. 4A depicts 1 second of a wave pattern with a perceived pitch 402 of 10 Hz, that is, the wave pattern oscillates 10 times per second. The graph shown in FIG. 4B depicts a sine wave-shaped envelope 404 whose frequency is 1 Hz. Perceived beat frequency is always twice the frequency of the envelope. Thus, in this example, the perceived beat frequency is 2 Hz. When the base tone shown in FIG. 4A is modulated by the envelope 404 shown in FIG. 4B, the resultant wave pattern/fundamental vibration, shown in FIG. 4C, exhibits a perceived beat frequency of 2 Hz (i.e. the user perceives that the pattern repeats twice a second). Eqn. 1 is used to find the shape of the wave pattern for a given frequency of a perceived pitch:

$$\text{signal\_base\_tone} = \sin(2.0 * \pi * \text{freq\_perceived\_pitch} * t). \quad [\text{Eqn. 1}]$$

This equation seeks to find the base tone's signal, or amplitude, at each timepoint. In Eqn. 1, the freq_perceived_pitch is the frequency of the base tone in Hz. For the example shown in FIG. 4A, the frequency of the base tone is 10 Hz and the time varies along the X-axis. In this example, between 0.02 and 0.03 seconds, the wave has reached its maximum positive signal (1.0), then heads back down to zero between 0.05 and 0.06 seconds, reaches its maximum negative signal between 0.07 and 0.08 seconds (−1.0), then heads back up to zero by around 0.1 seconds. The values for Eqn. 1 establish the range of values and shape of the wave pattern shown in FIG. 4A.

Eqn. 2 is used to find the shape of the envelope for a given perceived beat frequency:

$$\text{signal\_envelope} = \sin(\pi * \text{freq\_perceived\_beat} * t) \quad [\text{Eqn. 2}]$$

In Eqn. 2, the freq_perceived beat is the frequency of the perceived beat in Hz. For the example shown in FIG. 4B, the frequency of the perceived beat is 2 Hz and the time varies along the X-axis. In this example, at 0.25 seconds, the wave has reached its maximum positive signal (1.0), then heads back down to zero at about 0.5 seconds, reaches its maximum negative signal at 0.75 seconds (−1.0), then heads back up to zero by around 1 second. In this example, the wave pattern is a sine wave generated at 1 Hz, as depicted in FIG. 4B.

Combining the two wave patterns results in the base tone being modulated by a sine-wave based envelope. To achieve the wave pattern shown in FIG. 4C, the wave patterns depicted in FIGS. 4A and 4B are multiplicatively combined in accordance with Eqn. 3:

$$\text{signal\_fundamental\_vibration} = \text{signal\_base\_tone} * \text{signal\_envelope} \quad [\text{Eqn. 3}]$$

In Eqn. 3, the results of Eqn. 1 and Eqn. 2 are multiplied for each timepoint to generate the signal_fundamental_vibration at that particular timepoint. For example, at 0.23 seconds, the value of signal_base_tone is 1.0 and the value of signal_envelope is 1.0 and their product, or signal_fundamental_vibration, is 1.0, which is the maximum positive signal for the combined wave patterns. This maximum signal is reached again at 0.77 seconds, during the second portion of the 2 Hz envelope.

Ultimately, the fundamental vibration is translated into a signal that is sent to a transducer, wherein the signal is limited to a range of values that is appropriate for the transducer being used and the given intensity.

In this embodiment, intensity is a scalar value between 0 and 1, which attenuates the amplitude of the fundamental vibration.

$$\text{signal\_output} = \text{signal\_fundamental\_vibration} * \text{intensity} \quad [\text{Eqn. 4}],$$

Signal_output is defined as the signal that is output by the transducer.

In some embodiments, intensity need not be interpreted as an attenuation of amplitude, but rather the power of the signal (in g-force), measured at the transducer. The signal that is sent to the transducer or speaker is an electrical signal measured by voltage. The transformation from voltage into signal power may not be linear. In order to maintain a consistent level of power, the amplitude may be adjusted relative to the physics of the transducer. As an example, for base signals whose frequencies are near the resonant frequency of the transducer, the output signal may need to be attenuated.

Figure 5A:
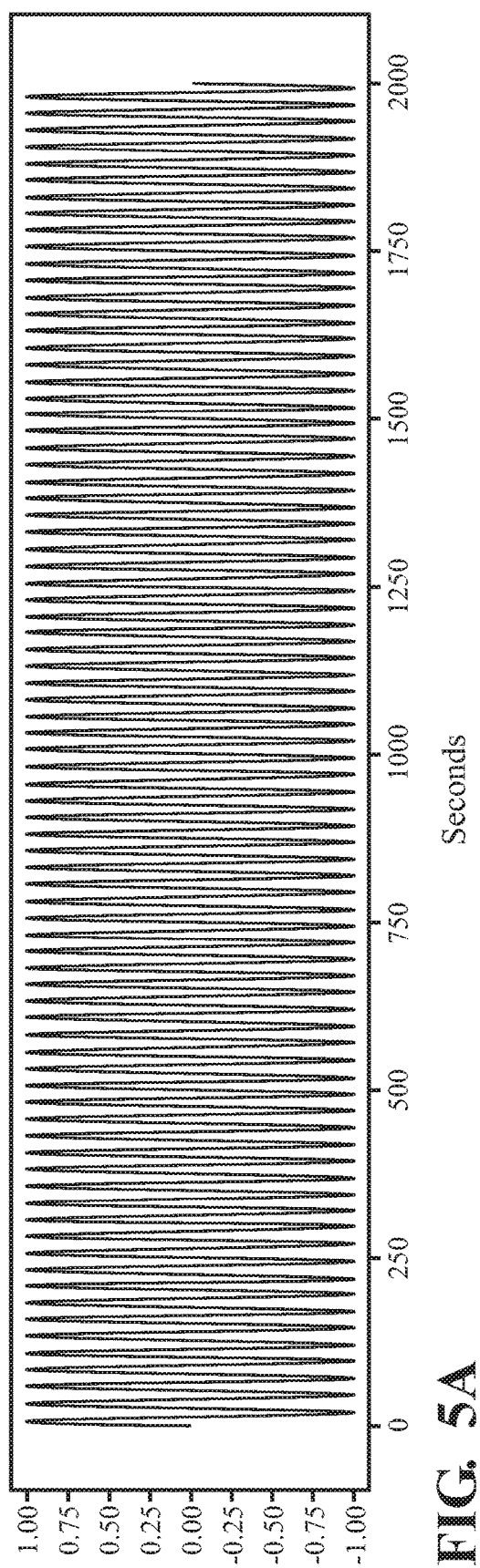
FIG. 5A depicts a frequency with a perceived pitch and FIG. 5B depicts an envelope.
Figure 5B:
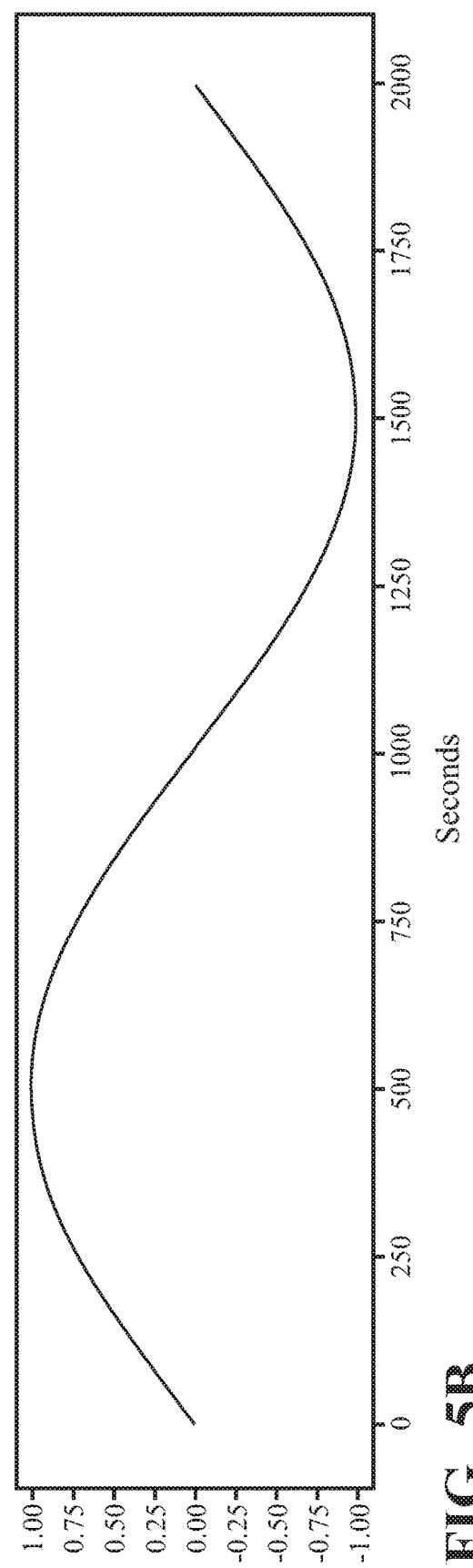
Figure 5C:
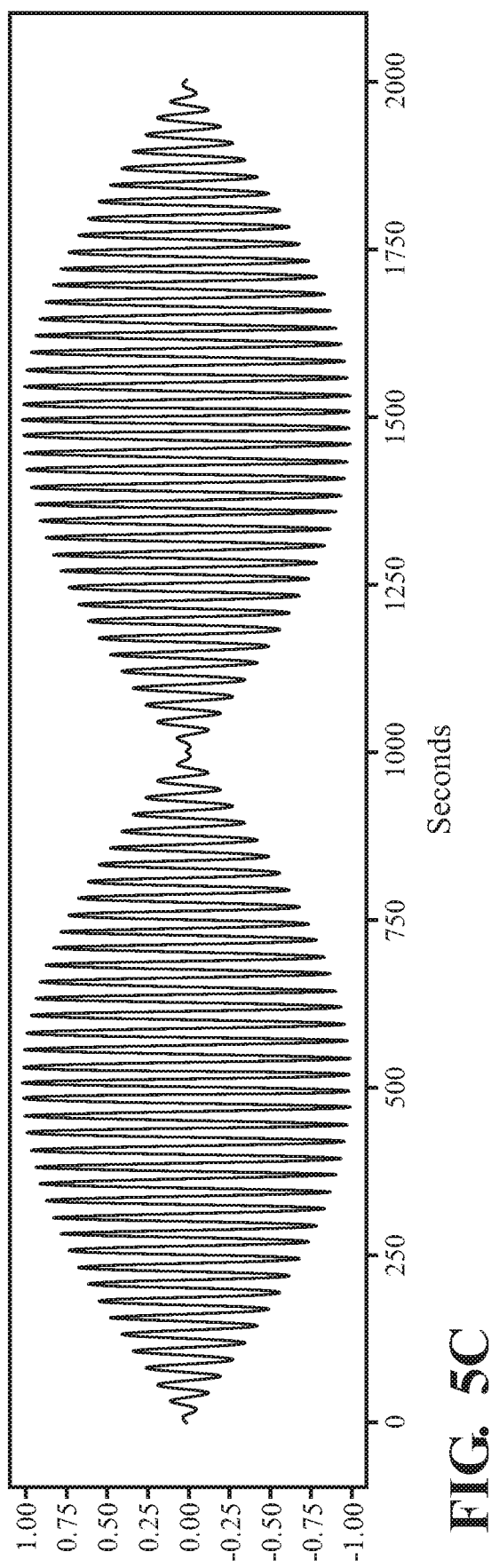
FIG. 5C depicts a waveform generated by modulating the wave in FIG. 5A by the envelope in FIG. 5B.
Figure 7:
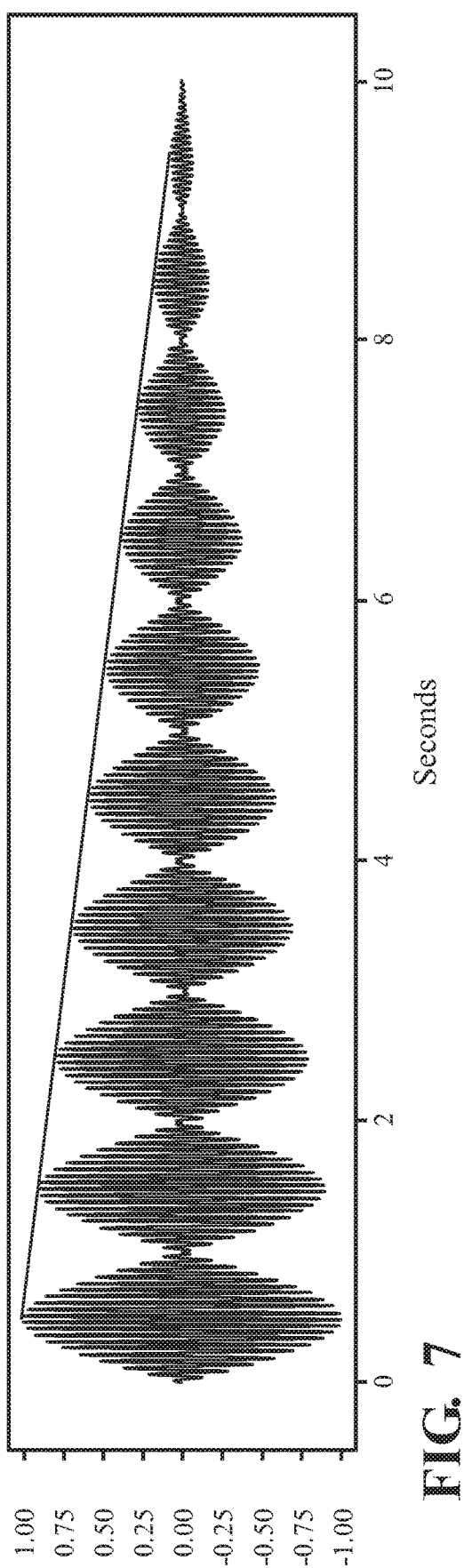
FIG. 7 depicts a waveform with a changing maximum intensity.

In embodiments, the fundamental vibration may be further modulated. In an additional example, FIG. 5A depicts a base tone and FIG. 5B depicts an envelope. FIG. 5C is the fundamental vibration generated by modulating the wave in FIG. 5A by the envelope in FIG. 5B. Referring now to FIG. 7, depicted is a waveform with a perceived pitch of 20 Hz that is unaltered over the charted time period and a perceived beat frequency of 1 Hz, which is also unaltered over the charted time period. The maximum intensity, however, is changing over the time period shown. A line drawn from the apex of the first beat to the apex of the last beat indicates that the change has a negative slope, which translates to an approximate rate of about 0.009%. In this example, a programmer may have set the perceived pitch and perceived beat frequency of the wave pattern and a starting intensity and indicated that the intensity should be ramped down at a rate of 0.009% over time without altering perceived pitch or perceived beat. Thus, the ramp down changes the maximum intensity, without altering the envelope.

Figure 8:
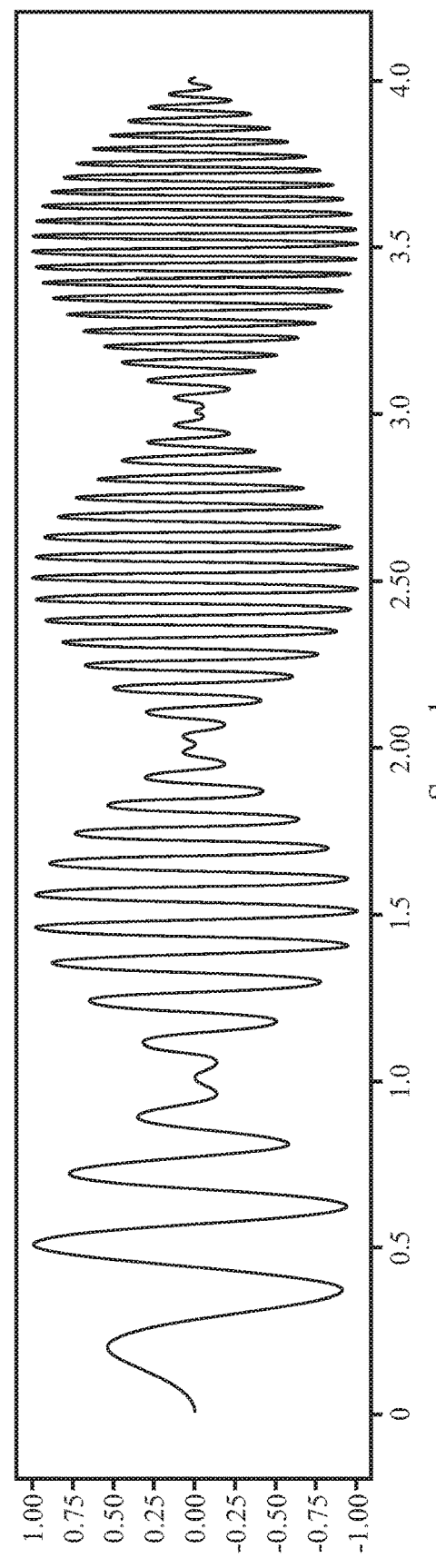
FIG. 8 depicts a waveform with increasing perceived pitch.
Figure 9:
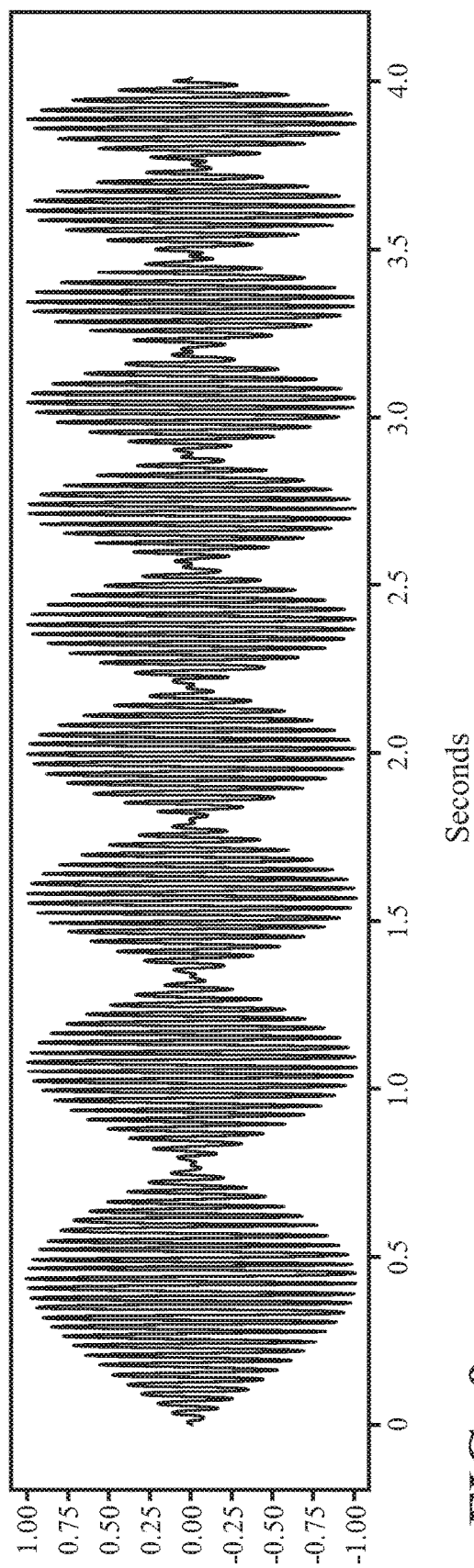
FIG. 9 depicts a waveform with increasing beat frequency.
Figure 10:
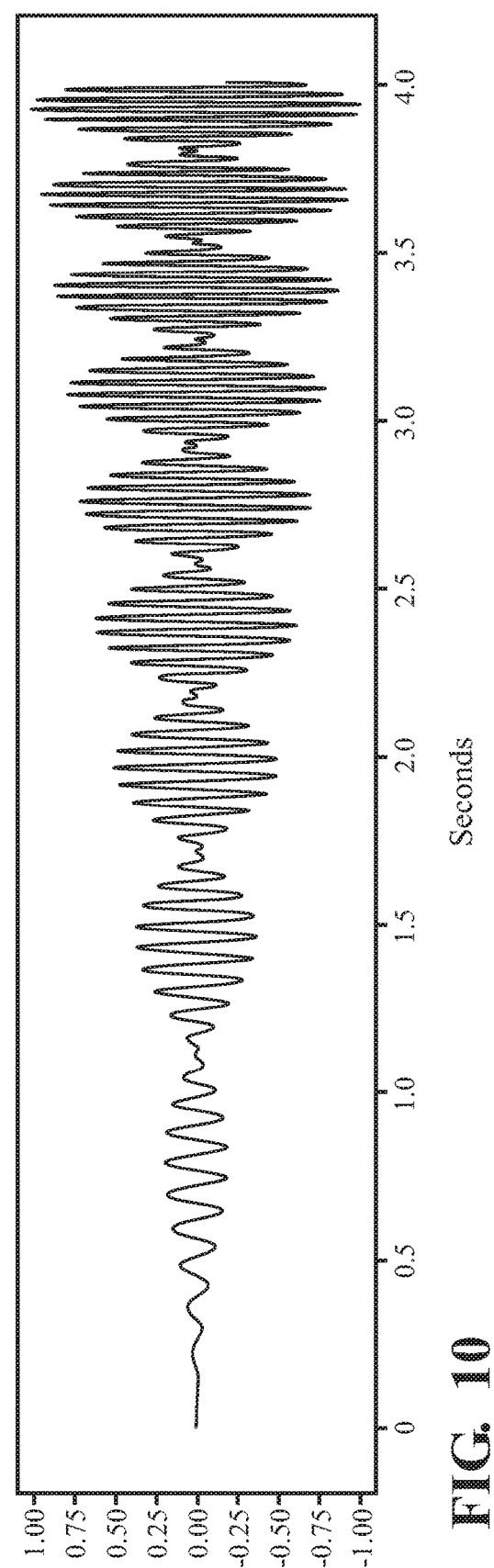
FIG. 10 depicts a waveform with increasing perceived pitch, perceived beat and intensity.

In the wave shown in FIG. 8 (e.g. a sweep (perceived pitch)), the perceived pitch starts low and increases linearly to a maximum intensity with no change in the perceived beat. In the wave shown in FIG. 9 (e.g. a sweep (envelope)), the pitch and intensity are unchanged over time but the beat frequency increases over time. In the wave shown in FIG. 10, the perceived pitch, perceived beat and intensity are all increasing over time.

The waveforms depicted above are output via the transducer described herein. Modifying the resultant waveforms parameters of pitch, beat, and intensity can be done to achieve different base tones/envelopes and therapeutic ends.

In embodiments, the transducer 201 may provide the stimulation in the form of: a base tone or wave with perceived pitch in the range of 1-500 Hz and an envelope with a perceived beat frequency that modulates the base tone in the range of 0.0001-20 Hz with a perceived intensity that is determined based on each individual user's sensory threshold. The lower sensory threshold is minimum intensity level at which the user becomes aware of the waves/vibrations. The upper end of the sensory threshold may be an intensity level of the stimulation at which the user would have difficulty ignoring the vibrations or find them distracting. As described elsewhere herein, determining the individual user's sensory threshold may be done via at least one of three methods: a) calibration; b) active data collection (via brief survey questions in-app); and c) passive data collection (via monitoring mobile device and app usage).

In the setting of users' having different sensitivities to the frequency of the base signal, the intensity can be implemented to modulate the power of the transducer output signal to ensure the users' perceived intensity is consistent across base frequencies.

In certain embodiments, stimulation provided by the device 102 may be a combination of sine wave oscillations of different frequencies that results in a beat frequency that is output to the subject. The combination of a main frequency and a modulation frequency results in a beat output that provides to a user a feeling of slow or fast waves of stimulation at a frequency determined to be arousing or calming based on a treatment being administered, as elsewhere described herein, and/or the physiology of the subject. The applied stimulation may include a single modulation frequency or multiple modulation frequencies. The generation of fundamental vibrations using interference patterns is an alternative embodiment than that described with respect to using a base tone whose intensity is modulated by an envelope. In this alternative embodiment, the values for perceived pitch and frequency of the signal's 'beat' are derived from the two frequencies of the beat interference pattern, in accordance with the following equations.

$$\text{freq\_perceived\_pitch} = (\text{freq\_interference1} + \text{freq\_interference2})/2 \quad [\text{Eqn. 5}]$$

$$\text{freq\_perceived\_beat} = \text{freq\_interference1} - \text{freq\_interference2} \quad [\text{Eqn. 6}]$$

In this alternative embodiment, the beat interference pattern may arise from pre-generated sine waves using signal data extracted from WAV audio files.

For example, the transducer 201 may provide the simulation in the form of: (i) a main frequency of 1-500 Hz modulated by a modulation frequency that differs from the main frequency by about 0.0001-10 Hz; (ii) a main frequency of 1-100 Hz modulated by a modulation frequency that differs from the main frequency by about 0.0001-1 Hz; or (iii) other frequency values within the ranges listed above. The combination of the main frequency and the modulation frequency results in an interference wave pattern and a beat output. The interference wave pattern and beat output may provide a user a feeling of slow waves of stimulation at a frequency determined to be arousing or calming based on the treatment being administered and/or the physiology of the subject. The applied stimulation may include a single modulation frequency or multiple modulation frequencies. In embodiments, one transducer 201 may deliver the main frequency while another transducer 201 delivers the modulation frequency, or perceived beat. The acoustical or vibrational energy as used in this disclosure may be a low frequency sound (acoustical energy) or vibration (mechanical energy). For example, the sonic vibration that is delivered may be in the form of a primary frequency of approximately 1-100 Hz. In some embodiments, the primary frequency may be approximately 1-40 Hz, approximately 1-30 Hz, approximately 1-33 Hz, or other values in those ranges. In some embodiments that result in interference patterns, the primary frequency may be combined with a modulation frequency, or more than one modulation frequency, that is approximately 0.0001-1 Hz different from the primary frequency. The two frequencies together may form a beat frequency output. For example, in applications designed to maintain the subject in a state of sleep, the primary frequency may be in a range of 1-40 Hz, while the modulation frequency may differ from the primary frequency by about 0.0001-0.1 Hz. In one example, the stimulation device 102 delivers vibration output in the form of a main oscillation between 20-300 Hz and a modulation oscillation between 0.05-10 Hz, which together form a beat output. The stimulation device 102 may be designed to deliver output in the form of vibration, electrical output (e.g. voltage, such as a PWM waveform), audio output, or combinations thereof. In examples where the output is combined, the selected frequencies may be chosen to be complementary or synergistic.

Figure 12:
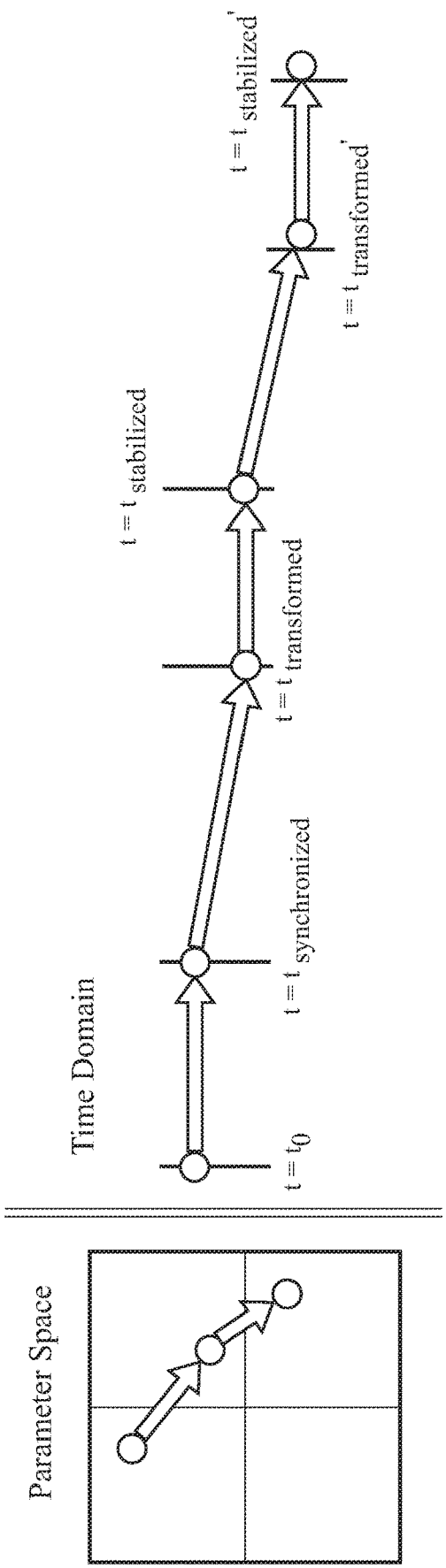
FIG. 12 depicts distinct phases of a vibration.

Referring now to FIG. 12, a wave may three phase types: synchronization, transformation, and stabilization. The segments are a sequence of fundamental vibrations starting from an initial vibration that transforms gradually to a goal fundamental frequency. In the synchronization phase, the stimulation device may emit the fundamental vibration corresponding to the physical/emotional state reported by the user when defining a wave. This initial vibration will be played a proportion of the overall application after which the wave will switch to 0 or more transformation/stabilization phase pairs. During a transformation phase, the parameters of the fundamental vibration are gradually modified until the parameters match those of the goal fundamental vibration. In stabilization, the vibration is played until a synchronization state is achieved where there is no expected change in mood or energy and may be maintained. By employing these phases, stimulation therapy can be aligned with a current state of the user first then gradually transform down to a middle state then to goal state. In the boundary case, a wave is equivalent to a fundamental vibration. In the boundary case, the initial and goal fundamental vibrations are the same and the length of the wave is infinite. In embodiments, the phase parameters for the initial or the goal vibration may be $\text{Freq}_{Tone}=1\text{-}300$ Hz, $\text{Freq}_{Envelope}=0.001\text{-}10$ Hz, intensity is a number between 0 and 100, and the duration is in seconds.

In some embodiments, the transformation from initial vibration parameters to goal vibration parameters may be linear. The phase parameters of synchronization and stabilization phases may have identical initial and goal vibrations. Fade-in/fade-out effects may be achieved by using Initial and goal vibrations with identical frequencies but different intensities (0 initial for fade-in, 0 goal for fade-out). Abrupt change may be done by using zero segments having zero duration.

Figure 11:
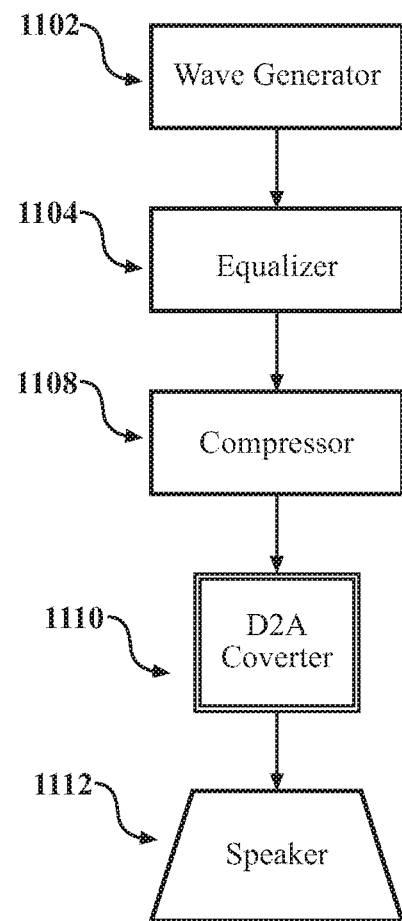
FIG. 11 depicts a system for equalization and compression.

In use cases where the frequencies are changing over time, the system may dynamically adjust the intensity of the vibrations to equalize the intensity level throughout. That is, and referring to FIG. 11, as the frequency generated by a wave generator 1102, such as a phase accumulator or numerically controlled oscillator, changes over time, there may be no significant perceptible change in the intensity level detectable by the user. Equalization refers to adjustments, which may be made by an equalizer 1104, made to the maximum amplitude of the signal to generate the signal at the same subjective level of intensity across all frequencies. Adjustments may be via a scaling factor between zero and one. Signals may also be compressed. Compression, which may be done by a compressor 1108, refers to adjustments made to the signal after equalization to map the signal values to the range of intensities identified by the user during calibration, the lower threshold tagged as 'just being able to feel' and the upper threshold being 'highest that can be tolerated'. After compression, the signal is sent to a digital-to-analog converter 1110. Included in the compression step is a check to ensure the output voltage to the speaker 1112 does not exceed a range, such as +−0.8 volts.

In embodiments, the system 100 may employ a coordinated system of multiple transducers 201. Each transducer in the system emits a transcutaneous vibratory output in accordance with a desired target state of the user, where each transducer emits one of the wave pattern for perceived pitch or the wave pattern for perceived beat, or each transducer in the system emits a different transcutaneous vibratory output in a pattern (e.g. simultaneously, sequentially, alternating, coordinated). For example, a first transducer may be disposed in a wearable applied to a user's wrist delivering a first stimulation pattern in a manner as described herein. A second transducer may be applied to a different part of the user's body, such as for example the neck, and may deliver a second stimulation pattern. The second stimulation pattern may be the same or it may be different. In embodiments, a first transducer may be disposed in a stimulation device and a second transducer may be disposed in a third-party device such as a mobile device. Note that the transducer in the mobile device may be of the type already incorporated into the mobile device to emit vibration or sound. The third-party device may also be a wearable. In embodiments embodiment, a first transducer may be disposed in a third-party wearable and a second transducer may be disposed in a device associated with the wearable, such as in a watch band or watch band clasp of the third party wearable. In embodiments, the transducer is disposed in a clasp/portion of a smartwatch band that is communicatively coupled to a smartwatch or smart device, wherein the clasp or band comprises at least one transducer for delivering oscillations/vibratory stimulation to a subject's wrist, including a ventral part of the wrist. The timing, intensity, beat output, pitch output of the two devices may be selected to achieve a particular coordinated pattern, such as a particular syncopation or rhythm across the transducers. Stimulation may be coordinated between the two transducers to deliver stimulation, in embodiments, that has similar effects as stimulation delivered by a single device with two transducers. Coordination may be done via a processor associated with the stimulation device, a third party device, a mobile device, or the like. Whether it is a single transducer or a coordinated set of transducers, stimulation therapy can be effective when the transducer is placed anywhere on or in proximity to the user's body. In alternative methods of generating the transcutaneous vibratory output, one transducer may deliver a main frequency while another transducer delivers a modulation frequency.

Figure 6:
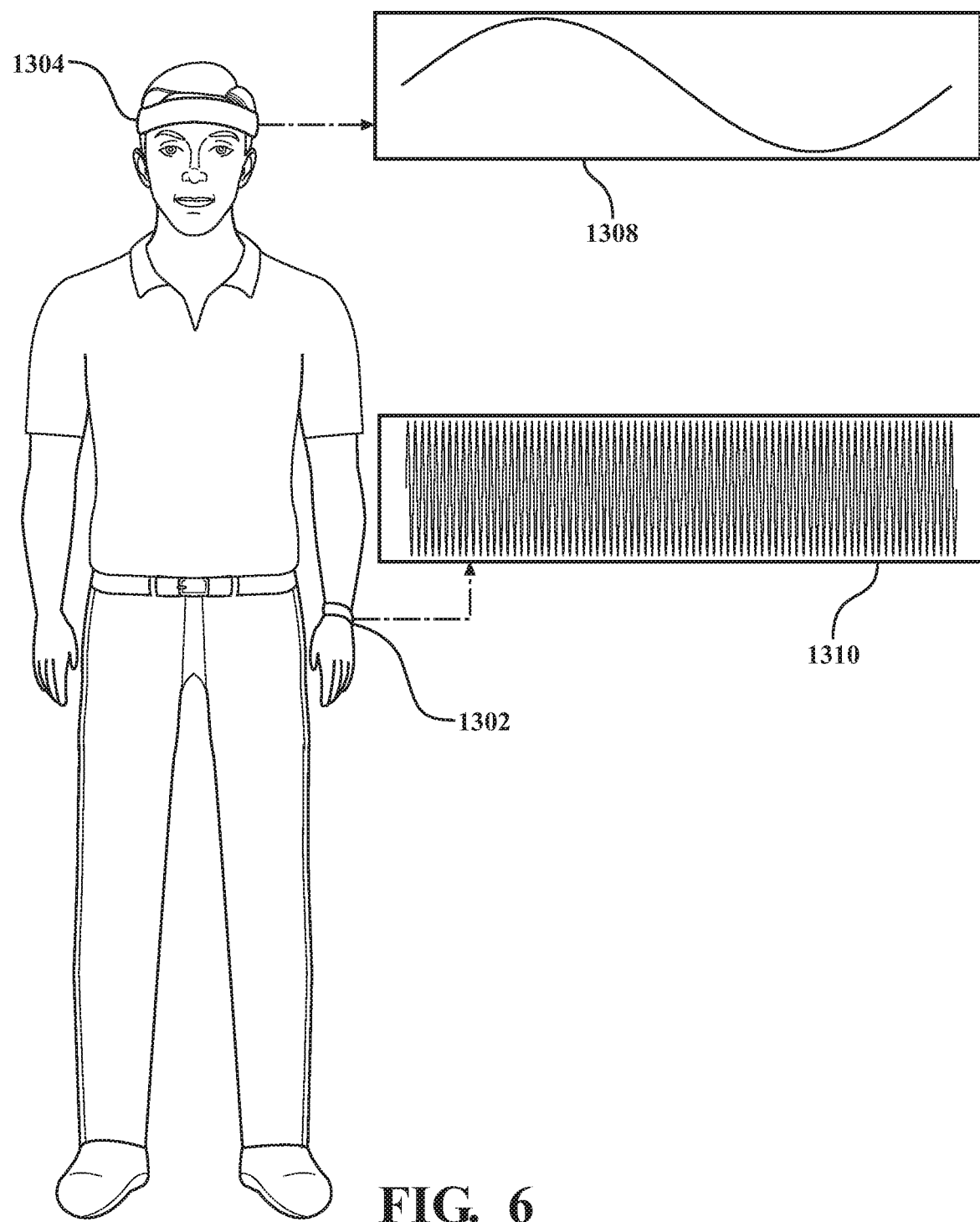
FIG. 6 depicts a coordinated set of transducers delivering stimulation described herein.

Referring now to FIG. 6, a system to deliver vibratory therapy to a user may include a first transducer 1302 adapted to emit a first transcutaneous vibratory output 1308 and a second transducer 1304 adapted to emit a second transcutaneous vibratory output 1310. The first transducer may be worn on a first part of a user's body while the second transducer is worn on a second part of the user's body. The user is able to select a target state desired by the vibratory therapy using a user interface in communication with the first transducer and/or the second transducer, wherein the transcutaneous vibratory output patterns may be based on the target state. In embodiments, the user interface is running on an application on a mobile device. A processor may be in electronic communication with the user interface, the first transducer, and the second transducer. The processor may be part of the first or second transducer, or may be in a separate device. In an embodiment, the first transducer may be in electronic communication with the second transducer. The processor may be programmed to cause the transducers to generate transcutaneous vibratory output patterns and emit transcutaneous vibratory outputs in accordance with those patterns, each transcutaneous vibratory output comprising a perceived pitch, a perceived beat, and a perceived intensity, each of which may be the same or different.

In embodiments, the first transcutaneous vibratory output pattern and the second transcutaneous vibratory output patterns may be emitted simultaneously, sequentially, or in an alternating pattern. In embodiments, the first transcutaneous vibratory output pattern and the second transcutaneous vibratory output patterns may be independent of one another or coordinated with one another. In some embodiments, the second transcutaneous vibratory output is discontinued while the first transcutaneous vibratory output is emitted, or vice-versa. In an embodiment, the processor may be programmed to modify the first transcutaneous vibratory output pattern by varying the first perceived pitch, and further, to modify the second transcutaneous vibratory output pattern by varying the second perceived pitch. In an embodiment, the processor may be programmed to modify the first transcutaneous vibratory output pattern by varying the first perceived beat, and further, to modify the second transcutaneous vibratory output pattern by varying the second perceived beat. In an embodiment, the processor may be programmed to modify the vibratory patterns by varying the perceived intensity. In an embodiment, the processor of the first transducer may be programmed to modify the first transcutaneous vibratory output pattern based on data received from the second transducer.

Fundamental vibrations whose variable parameters are perceived pitch, or frequency of the base (carrier) tone, frequency of the perceived beat and maximum intensity (simply referred to as intensity) may be used in methods and systems to assist subjects in reaching a target state. The transcutaneous vibratory output may be applied to a portion of the subject's body as described herein to assist the subject in achieving the target state. In accordance, with input of a desired target state of the subject, transcutaneous vibratory output may be generated having variable parameters comprising a perceived pitch, a perceived beat, and a perceived intensity.

The stimulation device 102 and/or associated application may be programmed to deliver stimulation whose parameters are selected to cause a user to reach a target state (e.g. arousal, relaxation, asleep, lower heart rate, lower blood pressure, calm, focus, flow, presence of being, asleep, wakeful, relaxed, aroused, euphoric, etc.), facilitate entry into a target state, treat a condition (e.g. anxiety; insomnia; chronic pain; chronic stress; autism; depression, psychosis, headache, migraine, autoimmune disorders; hypertension; disorders relating to hypoarousal such as narcolepsy, fatigue, excessive daytime somnolence, chronic fatigue syndrome, constipation, catatonia, metabolic syndrome, eating disorders, obesity, hypotension, dysautonomia, attention deficit disorder, attention disorders that are characterized by decreased or unbalanced activity of the sympathetic nervous system over time (e.g. wherein treatment causes increased attention to inside the body by increasing parasympathetic tone relative to sympathetic tone, or increased attention to stimuli external to the body by increasing sympathetic tone relative to parasympathetic), motion sickness, vertigo, vasovagal reactions, disorders of metabolism including insulin insensitivity (type 2 diabetes mellitus) and metabolic syndrome, autonomic disorders, autoimmune disorders, or anemia), mitigate a side effect of a treatment, and the like. Each target state may be defined by certain parameters, such as physiological parameters or biometric parameters. For example, a calm state may be identifiable based on a heart rate below 60 bpm, an HRV above 80, a high frequency of positive words on social media postings and texts, a low speaking volume, or the like. In another example, an agitated state might be identifiable based on a heart rate over 100 bpm, an HRV below 40, a high-pitched speaking volume, increased use of negative words, and the like.

Configuring the stimulation to achieve a target state or maintain a current state may comprise adjusting one or more of the variable parameters. Any of the parameters of the stimulation may be modified, either individually or in combination of two or more. Modification may include increasing or decreasing one or more of perceived pitch, perceived beat, or intensity. For example, in assisting a target in reaching a state of flow (peak performance), the parameters of the transcutaneous vibratory output used to reach the state of flow may be derived from a lookup table, may be based on transcutaneous vibratory output that previously successfully facilitated entry into a flow state for the subject, may be done in real time in accordance with sensor feedback, may be done manually, or the like. For example, the variable parameters may be modified using a user interface of the stimulation device or of an associated device controlling the stimulation device. In embodiments, during application of the transcutaneous vibratory output, at least one of the variable parameters may be varied to generate a second transcutaneous vibratory output to be applied to a portion of the subject's body to assist the subject in achieving the target state.

In embodiments, the parameters of the transcutaneous vibratory output may be dynamically adjusted to prevent habituation. In certain embodiments, the beat frequency output is dynamic and not constant in order to prevent habituation by the subject. The dynamic nature may be induced based on data collected by the sensor device 118, based on user feedback, and/or automatically. For example, if the data collected by the sensor device indicates that the balance between the sympathetic and parasympathetic nervous systems has improved over a period of time but is not yet at the optimal level, the primary frequency may be tapered gradually rather than an immediate shut off. In subsequent attempts to reach the same target state, one of the variable parameters (e.g. pitch, beat, intensity), or the tapering or ramping rate may be varied from those used in a previous session to prevent habituation. Alternatively, and/or additionally, the user interface of the system may include an input field in which a user can select modes that will increase or decrease the speed by which the frequencies taper from an upper starting point to a lower ending point. In yet another embodiment, the dynamic nature may be induced automatically. As noted above, the system may be programmed to resume the stimulation (or stop it from turning off) if data from one or more of these sensors exceeds a threshold value.

In embodiments, the system may be programmed to receive user input and user feedback to manually initiate, terminate or adjust stimulation, such as in a user interface of the stimulation device, in a user input device, verbally indicating the state to a microphone input, in an application controlling the stimulation device, such as an application executing on a mobile device (e.g. smartphone, smart watch, smart eyewear, etc.), or the like. For example, a user may input a current state and/or a desired target state. The user's current state or condition may be indicated by the user (e.g. "I feel stressed"). A stimulation protocol or transcutaneous vibratory output may be selected based on the desired target state, based on the current state indicated by the user, and optionally, based on the current state relative to the desired target state. Based on the input, the transducer of the stimulation device generates a first transcutaneous vibratory output to be applied to a portion of the user's body to assist the user in achieving the desired target state, the first transcutaneous vibratory output comprising a first perceived pitch, a first perceived beat, and a perceived intensity. Determining if the user has achieved the target goal state may also be done subjectively, such as by receiving an input from the user of goal achievement (e.g. "I feel good"), as described herein, or by the user manually discontinuing stimulation. Throughout the stimulation, the user may also input or be prompted to input if they are still feeling that they have not reached the target state, if they are still in the initial state, or if they feel they are in between states. If the user has not achieved the desired target state, a second transcutaneous vibratory output may be generated, such as with the stimulation device, and delivered to the user in achieving the desired target state. The second transcutaneous vibratory output may have variable parameters (e.g. perceived pitch, perceived beat, and perceived intensity) that are different from those of the first transcutaneous vibratory output.

Determining current state or condition or goal state achievement may also be done: using biometric data, using sensed physiological data (e.g. HRV, GSR, heart rate, respiration rate, etc.), using sensor readings in comparison to a target physiological profile, in accordance with usage patterns, based on third party data, based on social media, or the like. In various embodiments, a target state may be indicated, such as in a user interface or using data collected by the sensor device(s) that indicates the need for a target state. In embodiments, a target state may be a particular health index. Health index may be an aggregate of various health-related measures, such as blood pressure, heart rate, HRV, ratio of HR/HRV, or the like.

In embodiments, data collected by the sensor device(s) may be used as feedback to initiate and/or control the application of the stimulus, or a first transcutaneous vibratory output, to the subject, via the stimulation device 102. Additionally, and/or alternatively, the data collected by the sensor device may be used to select and personalize the application of stimulation to the subject 114 based on the data collected by the sensor device. For example, the frequency ranges, stimulation patterns, stimulation application times, stimulation application duration, or the like may be personalized to a user. Continuous or periodic monitoring using sensors may be done, optionally along with comparison to parameters for a known/stored state. For example, if a user is attempting to reach a target state of being asleep, sensed parameters associated with that state may be high HRV, low movement, and low audible sound. In this case, one or more of a motion sensor, biometric or physiological sensor, or microphone may be used to monitor the user for possible entry into the state of sleep based on the group, or part of the group, of sensed parameters in comparison to known ranges of the sensed parameters. In another example, if the target state is wakeful and sensors indicate low HRV, stimulation may be initiated to address hypoarousal. In yet another embodiment, sensors indicating high HR and low HRV in the absence of physical activity may trigger a therapeutic stimulation for hyperarousal. The sensor device may use this sensor feedback to continue operation of the device if the user has not reached the target state or an expected state (e.g. Generally, fast, high intensity vibration patterns may increase HR, respirations, blood pressure, and sweat while decreasing HRV. Generally, slow, gentle, low intensity vibration patterns may decrease HR, respirations, blood pressure, and sweat while increasing HRV), as evidenced by sensors, terminate operation if the user has reached the target state, begin a tapering of stimulation if sensors indicate the user is approaching the target state, generate a second transcutaneous vibratory output, or the like. The second transcutaneous vibratory output may have variable parameters (e.g. perceived pitch, perceived beat, and perceived intensity) that are different from those of the first transcutaneous vibratory output.

In embodiments, a system to alter the mood of a user may include a user input device, a stimulation device which includes a transducer adapted to emit transcutaneous vibratory output, a physiological sensor sensing a physiological parameter of the user, and a processor in electronic communication with the user input device, the transducer and the physiological sensor. The system may accept input of a desired state of the user, and in response, cause the transducer to generate a first transcutaneous vibratory output to be applied to a portion of the user's body to assist the user in achieving the desired target state. In this embodiment, the first transcutaneous vibratory output may include parameters including a first perceived pitch, a first perceived beat, and a perceived intensity. The physiological parameter of the user may be used to determine whether the user has achieved the desired target state. If the user has not achieved the desired target state, the transducer may generate a second transcutaneous vibratory output to be applied to a portion of the user's body to assist the user in achieving the desired target state, the second transcutaneous vibratory output having parameters including a second perceived pitch, a second perceived beat, and a perceived intensity, which may be a second perceived intensity.

In an embodiment, stimulation may be terminated once a state has been reached as indicated by passive sensing (e.g. derived from other information sources) or active sensing (e.g. accelerometer indicates no movement, respiration rate indicates sleep, position, sensors indicate a health index/level). In an embodiment, stimulation may be resumed when sensors indicate the state has changed. The system may be programmed to resume stimulation (or stop it from turning off, or extend a tapering time) if data from one or more of these sensors exceeds a threshold value, or alternatively, based on an elapsed time. The system may be programmed to initiate a program when a particular sensor reading is received.

In certain aspects, sensors may determine a current contextual or physiological condition for the user and stimulation may be initiated, terminated or adjusted based on one or more detected states. For example, if sensors indicate stress (e.g. based on a health index), other data may be used to modulate turning on/off the stimulation. In an example, if an accelerometer indicates that the user is moving at an exercise rate, then the sensor readings are likely not indicating stress but rather reflect exercise. In an embodiment, if sensors indicate slowing down of movement at a particular time, that may be interpreted as getting ready for sleep, and the stimulation device's sleep routine may commence. In an embodiment, if sensors indicate the user is in a car but is experiencing drowsiness, the stimulation device 102 may be caused to commence delivery of stimulation configured to promote wakefulness.

In an embodiment, determining if a user has reached a target or goal state as a result of a stimulation may be done via user input, using system data, passive user data or sensing wearables (e.g. smart watch, medical device (e.g. blood pressure cuff, pulse ox, thermometer)), exercise/activity monitor, or other wearable item, or may be done using external and/or third party sources, such as third-party data, third-party devices, SaaS applications, health and fitness informatics applications, health and fitness APIs, hospital data systems, social media posts, communications, and the like. For example, a processor of or associated with a stimulation device may be programmed to receive a user's social media posts and commentaries and assess the language used for tone and emotion. In some embodiments, any combination of user input, internal sensing, or external data or sources may be used to determine if the user has reached goal state. The external and/or third party sources may provide data on physiological parameters (e.g. blood pressure, HRV, GSR, respiration rate, etc.). In some embodiments, based on determining if the goal state has been reached from external and/or third party sources, a second stimulation may be generated and delivered/applied to the subject to assist in reaching or maintaining the target state. In some embodiments, based on determining if the goal state has been reached from external and/or third party sources, stimulation may be discontinued or extended.

Configuring the stimulation to achieve a target state or maintain a current state may comprise generating stimulation of more than one segment, such as to obtain a session of stimulation having a series or a concatenation of stimulation patterns to achieve a desired state. In some embodiments, the session may be associated with an event, such as an entertainment event, an athletic event, a stress-inducing event, a psychotherapy session, or the like, and each segment is selected to produce an "overall" experience conducive to the event or session. For example, a session for mitigating anxiety of air travel may have multiple segments, such as a segment that is executed while the subject is waiting to board, then another while on board but awaiting takeoff, one during takeoff, one during flight, and the like. The user may manually indicate when the status of air travel has changed so that a next segment is executed. Data, such as third party data may be used to indicate when the status of air travel has changed so that a next segment is executed, such as for example, air traffic control and airline status data. Sensors may be used to indicate the status of the air travel in order to move from one segment to another, such as a microphone to hear announcements, a connected camera in smart eyewear, an altimeter to indicate altitude, or the like. In embodiments, data regarding an event to be or currently being experienced by the user may be obtained by a user interface, a contextual, biometric or physiological sensor, third party data or applications, and the like. Physiological sensors may include respiration, temperature, GSR, $SpO_2$, spirometry, EEG, ECG, EMG, heart rate, HRV, $CO_2$, motion, blood pressure, glucose, or the like. Biometric sensors may capture data regarding fingerprints, visual/facial cues, vocal tone, vocal pitch, the iris, or the like. Contextual sensors may capture data regarding the geospatial environment, location, meteorology and weather, air pollution/quality monitoring, flood monitoring, or the like. In some embodiments, the data regarding the event is a change in the event, such as a change in a traffic pattern, a delay in takeoff, a significant change in the weather, or the like.

Other examples of events where a session of stimulation may be useful include at athletic events, during public speaking sessions, during a speech or presentation, during a commute, for the treatment of a particular disorder (e.g. PTSD), for a desired feeling or desired outcome for the day, or the like. In the case of a commute, for example, data, such as from a traffic, GPS, or navigation application, may be used to determine speed, location, volume of surrounding traffic, and the like, and these data may be used to create the therapeutic session parameters and may also be used to move the session from segment to segment, such as one segment when traffic is moving, and another when traffic is at a crawl.

In embodiments, the segments of the stimulation may each be defined by one or more parameters including a perceived pitch, a perceived beat, and an intensity. In generating each segment, a value for each of the variable parameters may be assigned for each segment. Data regarding an event to be experienced by the user may be communicated to a computer processor that is configured to create therapeutic session parameters. The therapeutic session parameters may be created by assigning a set of contiguous output segments for the event, and based on the event, assigning a perceived pitch of transcutaneous vibratory output and a perceived beat of transcutaneous vibratory output to each output segment. A transducer generates the transcutaneous vibratory output for the therapeutic session based on the therapeutic session parameters, such as upon receiving the therapeutic session parameters from the computer processor. The therapeutic session parameters may be generated through machine learning of past responses to past events and past stimulations useful in reaching a goal state during or in spite of the event.

In embodiments, the segments may commence immediately after a prior segment has ended, or the stimulation may ramp up or taper down in at least one parametric aspect between segments. In embodiments, one or more of the variable parameters for each segment may be programmed in accordance with a target state, wherein programming may take advantage of a lookup table, may be based on transcutaneous vibratory output that previously successfully facilitated entry into the target state for the subject, may be done in real time in accordance with sensor feedback, may be done manually, or the like.

In some embodiments, the therapeutic session may be accompanied by other therapies or associated interventions, such as the delivery of compounds (e.g. pharmaceuticals, psychoactive agents, etc.), playing of music, back massage, release of certain aromas, dimming of lights, or the like.

In order to effectively provide stimulation, the device 102 and/or associated algorithm(s) may first be calibrated. Calibration may proceed in a number of ways, as will be described. In one aspect, calibration may comprise establishing characteristics of a baseline, non-stressed state and a health index, or signatures of various non-baseline states. For example, through initial use of the stimulation device and continuous recording of various parameters associated with the user, either through embedded or associated sensors, the user may indicate when they are stressed and non-stressed so that the algorithm associates the stored parameters with the identified states for future recall. Based on the health index, a range of frequencies may be delivered in response. For example, one range may be useful for treating depression while another range may be useful for facilitating sleep. In an embodiment, periodic or continuous monitoring of the baseline state and health index may enable fine-tuning the calibration in order to customize, individually and temporally, the range of frequencies delivered in response.

Another method of calibration to be able to detect stress-related transitions and unwanted stress may be to actively encourage entry into a particular state (e.g. resting, stressed, fatigued or other user-specified states) by delivering a particular stimulation known to provoke the state then storing the characteristics of the user after delivery of the stimulation and entry into the particular state for future reference. Confirmation of entry into the state may be done by the user or via sensor input. In another embodiment, a user may be encouraged to enter a relaxed state, such as by use of a mindfulness application, a meditation application, and/or stimulation, then delivery of a different stimulation known to provoke a state may be done and the user characteristics learned and associated with the state. For example, the user may be exposed to stimulation known to provoke increases in sympathetic tone and decreases in parasympathetic tone in order to provoke entry into a stressed state where the device 102 can learn the characteristics of that stressed state.

In one method of passive calibration, the user may be exposed to a range of stimulation patterns and then sensed parameters are used to determine if the user has reached a target state. After repeated attempts, the best calming pattern and the best arousing therapy pattern may be selected. In another method of passive calibration, a first transcutaneous vibratory output is delivered to a user with parameters comprising a first perceived pitch, a first perceived beat, and a perceived intensity. The parameters of the first transcutaneous vibratory output may be selected after determining a desired target state of a user, such as selected from a database or selected by prediction. After or during delivery of the first transcutaneous vibratory output, data, such as physiologically sensed data or user input, are used to determine if the user has reached a target state. Modifications may be made to the transcutaneous vibratory output in the course of this passive calibration to generate a second transcutaneous vibratory output. Then, the second transcutaneous vibratory output is delivered to the user with parameters comprising a second perceived pitch, a second perceived beat, and a perceived intensity, and data are again used to determine if the user has reached the target state. Based on the effectiveness of the first and second transcutaneous vibratory outputs, a processor may be used to select one of the first or second transcutaneous vibratory outputs to be used going forward in assisting the user to achieve the target state. In embodiments, the processor may select neither of the first nor second transcutaneous vibratory outputs in favor of continuing to iteratively modify the transcutaneous vibratory output in order to find a set of transcutaneous vibratory output parameters that are effective in assisting a user in reaching a target state.

In an embodiment, a plurality of transcutaneous vibratory outputs may be selected based on a desired target state to be used in a calibration session. Each of the transcutaneous vibratory outputs may be based on parameters including a perceived pitch, a perceived beat, and a perceived intensity, and may be selected from a database or selected by prediction. During or after emitting each of the plurality of transcutaneous vibratory outputs in a corresponding session, such as with an electronic transducer in contact with the portion of the user's body, data may be obtained regarding whether a user has achieved the desired target state in each of the corresponding sessions (e.g. with a physiological sensor or from user input). Upon determining the effectiveness of each of the plurality of transcutaneous vibratory outputs based on the data, one of the plurality of transcutaneous vibratory outputs may be selected as effective for assisting with entry to the desired target state for the user. The selected transcutaneous vibratory output may then be communicated to a database, the database comprising other transcutaneous vibratory outputs determined to be effective for the desired target state. The database may be accessed to identify other effective transcutaneous vibratory outputs. One or more other effective transcutaneous vibratory outputs may be selected from the database to be emitted with the electronic transducer. The plurality of vibratory outputs may be from one user, but in other embodiments, the database may store the vibratory outputs (and those deemed effective for a plurality of users) and thus be used to improve the effectiveness for multiple users.

In personalized passive calibration, periodic measurements may be taken at different time points of the day for a period of time after the user begins using the device 102. The measurements may be done by one or more sensors, such as physiological sensors, cameras, microphones, or the like, along with data collected from the user's manual adjustment of device operation. For example, the physiological parameter sensed by the sensors may be movement, heart rate, GSR, temperature, and the like. The assessments over the course of a period of time, such as the first week of use, may be used to determine a user's baseline state.

In any of the embodiments described herein, a user's baseline state may be calculated based on readings from one or more sensors, those sensors being described herein. The baseline state may be determined for a user for a period of time in a day, such as a morning baseline versus an evening baseline. In some embodiments, in addition to using sensor readings to establish a baseline state, the user may be prompted to provide information or ratings about their mood, such as into a user interface of a mobile device. Mood information may be used to confirm a sensor-based establishment of baseline or as another data point in the establishment of the baseline state. In yet other embodiments, the baseline state of the user may be additionally based on contextual data received from a mobile device of the user. The contextual data may be indicative of an amount of usage of the mobile device. The contextual data may be keystrokes input into the mobile device. The contextual data may be indicative of a mood of the user (e.g. negative, positive, frustration, anger, anxiety, distracted, etc.). The contextual data may be the content of social media posts, wherein the content is used to indicate a mood of the user (e.g. negative, positive, frustration, anger, anxiety, distracted, etc.). In yet still other embodiments, physiological data, user input, facial recognition data, contextual data, or any combination thereof may be used to establish a baseline state of a user. In this way, one person's baseline state can be different from another's baseline state.

The system may save baseline state data to a user profile that the system may access to set parameters (such as duration and timing, frequency and/or intensity) when applying stimulation to that user in the future. The system may continue to collect new data as the user uses the device, and it may supplement the user profile with that data and/or replace the oldest data with new data as it is received.

Continued measurement with a sensor may be used to determine a deviation from the baseline state. Deviation from the baseline state may indicate that the user is experiencing a stressor. Deviation from the baseline state may be detected by a change in a sensor reading or a change in a group of sensor readings. For example, the deviation may be a one standard deviation shift from the user's baseline. In response, a downstream action may be triggered, such as commencement of therapeutic stimulation, selecting a particular transcutaneous vibratory output to deliver, or triggering a request to commence therapeutic stimulation.

Depending on the magnitude of the deviation from baseline, an appropriate transcutaneous vibratory output given the user's current state may be selected. For example, if the user is only experiencing a one standard deviation shift from the user's baseline, the transcutaneous vibratory output selected may commence at a lower intensity in order to reach a target state than if the user was experiencing a greater shift from baseline. In another example, a smaller shift from baseline may require a shorter duration stimulation than if the user is far from baseline. Knowing where the baseline is and how far from baseline the user is currently at, transcutaneous vibratory outputs can be dynamically selected to assist the user to reach the target state from whatever their current state is. If the user does not reach the target state with the first transcutaneous vibratory output selected based on the personalized passive calibration, a second transcutaneous vibratory output can be selected and generated for application to the user in an effort to assist them in reaching the target state. Transcutaneous vibratory outputs may also be dynamically selected to avoid habituation.

Figure 13:
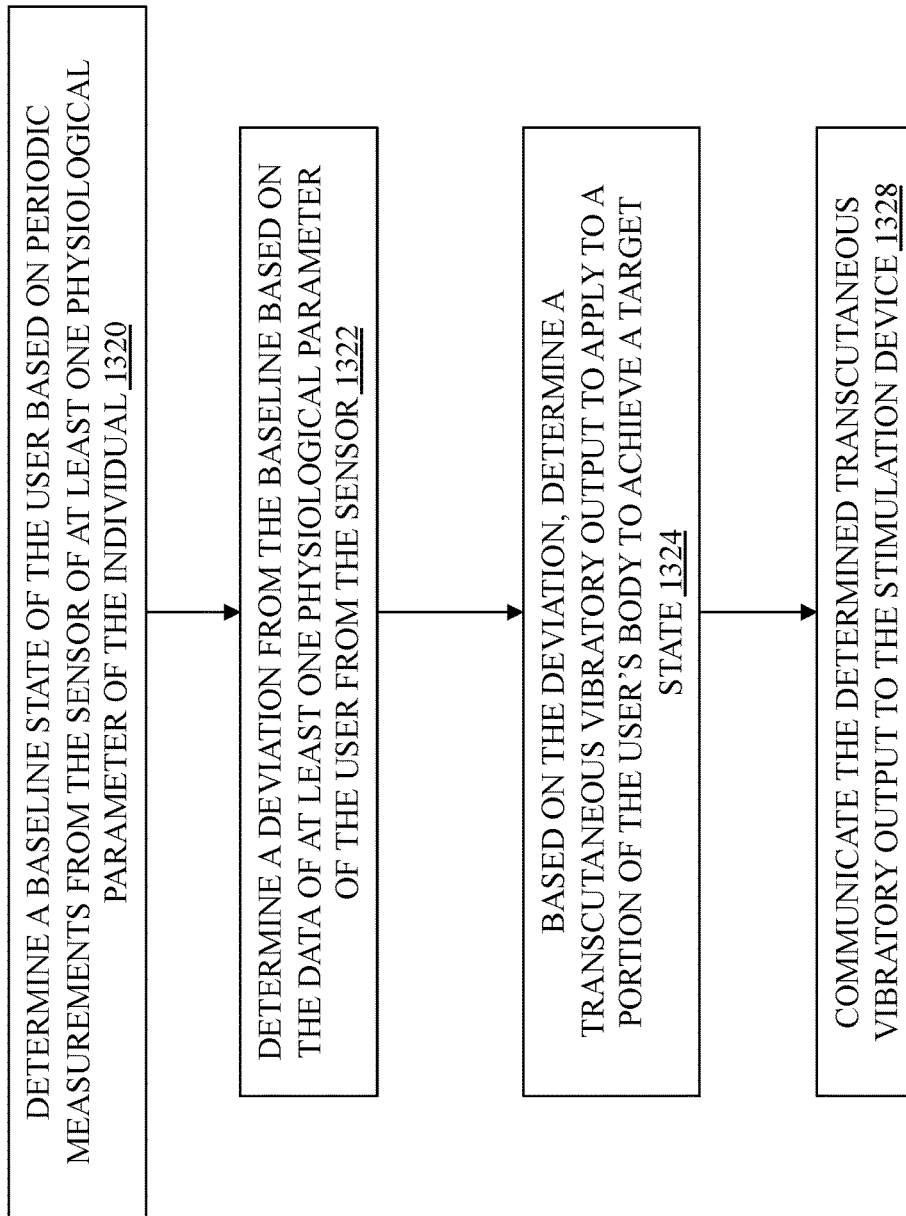
FIG. 13 depicts a process for calibration.

Personalized passive calibration may be embodied in a system comprising the stimulation device as described herein, a physiological sensor of the stimulation device periodically measuring data of at least one physiological parameter of the user, and a processor in electronic communication with a mobile device and the stimulation device. Referring to FIG. 13, the processor may be programmed to (i) determine a baseline state of the user based on periodic measurements from the sensor of at least one physiological parameter of the individual 1320; (ii) determine a deviation from the baseline based on the data of at least one physiological parameter of the user from the sensor 1322; (iii) based on the deviation, determine a transcutaneous vibratory output to apply to a portion of the user's body to achieve a target state 1324; and (iv) communicate the determined transcutaneous vibratory output to the stimulation device 1328. Based on the communicated determined transcutaneous vibratory output, the transducer of the stimulation device generates the transcutaneous vibratory output to be applied to a portion of the user's body, wherein the transcutaneous vibratory output comprises a first perceived pitch, a first perceived beat, and a first perceived intensity. The processor may be further programmed to determine a baseline state of the user by prompting the user to input data of the user's mood into the mobile device or by using contextual data or combinations thereof, as described herein. In any of the embodiments described herein, the processor may be further programmed to determine whether the user has achieved the target state (e.g. via sensor or user input), and if the user has not achieved the target state, cause the transducer to generate a second transcutaneous vibratory output to be applied to a portion of the user's body to assist the user in achieving the target state, the second transcutaneous vibratory output comprising a second perceived pitch, a second perceived beat, and a second perceived intensity.

Continued collection of baseline data may be stored to form a longitudinal data set. Iterative, real-time tuning and optimization of the delivered frequency may be based on the longitudinal data. For example, if the user's baseline changes over time, therapeutic stimulation is accurately triggered only when there is a deviation from the new baseline. Continuing with this example, as a user progresses with use of the device 102 and the baseline alters, perhaps to a calmer baseline state, the therapeutic stimulation protocol used upon a detection of a deviation from baseline may need to be varied in an aspect (e.g. frequency, intensity, and/or duration) in order to affect the user's state.

As indicated previously, determining an individual user's sensory threshold may be done via: a) calibration, as described herein; b) active data collection (via brief survey questions in-app); c) passive data collection (via monitoring mobile device and app usage to determine how far the user backs down stimulation or how much the user increases it); and the like. In embodiments, a sensory threshold may be determined for a user, such as via a calibration test. The sensory threshold may be manually adjusted by the user. The intensity of treatment frequencies may be delivered within one standard deviation from the sensory thresholds. The lower sensory threshold may be the level at which the vibration is barely noticeable when the user pays attention to it, but it is not distracting and fades into the background when the user attends away. The upper sensory threshold is where the stimulation may be distracting. Establishing a lower sensory threshold may be done by delivering a transcutaneous vibratory output to a portion of a user's body and gradually reducing an intensity of the transcutaneous vibratory output until the user indicates that it is barely noticeable, such as by using a user interface of a stimulation device or an application controlling a stimulation device. Establishing an upper sensory threshold may be by delivering a transcutaneous vibratory output to a portion of a user's body and gradually increasing an intensity of the transcutaneous vibratory output until the user indicates that it is distracting, such as by using a user interface of a stimulation device or an application controlling a stimulation device. Alternatively, the user may establish the lower and upper sensory thresholds themselves by manually adjusting an intensity of a stimulation until it is barely detectable on the lower end or distracting on the upper end, wherein the final values of the adjustment are stored as the sensory thresholds.

Delivery of stimulation may be configured such that it does not exceed a sensory threshold, is at or within one standard deviation from the sensory threshold, or some other point relative to the sensory threshold such that it cannot be felt or is not too distracting or uncomfortable. If the parameters of the stimulation are varied to generate a second stimulation, as described in various embodiments herein, the second stimulation may also be configured such that it does not exceed a sensory threshold, is at or within one standard deviation from the sensory threshold, or some other point relative to the sensory threshold such that it cannot be felt or is not too distracting or uncomfortable.

Delivery of therapeutic stimulation may take advantage of the sensory thresholds, such as for example to deliver stimulation that tapers. The intensity of tapered stimulation may start at an upper end of a sensory threshold and decrease to a barely detectable level over a first period (such as approximately 2 minutes to 15 minutes) at a rate (e.g. approximately 10% per minute). In embodiments, the intensity may remain at the final level for the remaining duration of stimulation (e.g., for another 15-25 minutes).

After the taper, stimulation may automatically turn off after a period of time (e.g. after the primary frequency has been applied at its lowest level for a period of time. After the taper, stimulation may automatically turn off after the total cycle (from starting value to lowest level) has been applied for a period of a period of time (e.g. at least 30 minutes). The intensity of the stimulus may remain at or within 1 standard-deviation of the medians of users' sensory threshold to provide the desired results.

In some treatment applications involving a stimulation pattern, the perceived pitch may be or start at about 1-200 Hz and the perceived beat may be between 0.0001-4 Hz, such as for treatment of disorders relating to hyperarousal such as sleep disorders, chronic pain, post-traumatic stress disorder, chronic stress, autism, autoimmune disorders, anxiety, hypertension, tachycardia, arrhythmias or the like that are characterized by increased activity of the sympathetic nervous system over time. There may also be more than one perceived pitch and more than one perceived beat.

Treating disorders related to a hyperarousal of the autonomic nervous system may include obtaining input of a hyperarousal disorder and a subject's sensory threshold for transcutaneous vibratory output. The input of the hyperarousal disorder may be obtained with a user interface in communication with a processor. Alternatively, input of the hyperarousal disorder may be obtained through sensed data or third party data. The user's sensory threshold is determined as described herein. Based on the hyperarousal disorder, the processor may select a stimulation pattern for transcutaneous vibratory output to be emitted by a transducer of a stimulation device, the stimulation pattern based on parameters comprising a perceived pitch, a perceived beat, and a perceived intensity. The computer processor may cause the transducer to generate the transcutaneous vibratory output in the selected stimulation pattern at a sensory threshold value at or above the subject's sensory threshold for transcutaneous vibratory output.

Examples of perceived pitch and perceived beat used to treat certain hyperarousal disorders are provided herein:

Treatment of chronic pain may include the application of a perceived pitch of about 200 Hz or less and a perceived beat that is equal to or less than about 0.25 Hz, optionally at an intensity within 1.5 standard deviations of the user's sensory threshold.

Treatment of chronic stress may include the application of a perceived pitch of 200 Hz or less and a perceived beat that is equal to or less than about 4 Hz, optionally at an intensity 1 standard deviation of the user's sensory threshold.

Treatment of autism may include the application of a perceived pitch of about 200 Hz or less and a perceived beat that is equal to or less than about 10 Hz, optionally at an intensity within 2 standard deviations of the user's sensory threshold.

Treatment of autoimmune disorders may include the application of a perceived pitch of about 200 Hz or less and a perceived beat that is equal to or less than about 10 Hz, optionally at an intensity within 2 standard deviations of the user's sensory threshold.

Treatment of anxiety may include the application of a perceived pitch of about 200 Hz or less and a perceived beat that is equal to or less than 4 Hz, optionally at an intensity within 1 standard deviation of the user's sensory threshold.

Treatment of hypertension may include the application of a perceived pitch of about 200 Hz or less and a perceived beat that is equal to or less than 4 Hz, optionally at an intensity within 1 standard deviation of the user's sensory threshold.

In certain other applications, the perceived pitch may be about 40-500 Hz and the perceived beat may be about 0.1-20 Hz (e.g., for treatment of disorders relating to hypoarousal such as depression, narcolepsy, fatigue, constipation, catatonia, metabolic syndrome, eating disorders, hypotension, attention disorders that are characterized by decreased or unbalanced activity of the sympathetic nervous system over time). In some embodiments, treatment of disorders relating to hypoarousal may use a perceived pitch of (or starting at) a level that is between 40 Hz to 500 Hz, with a perceived beat of 0.1-10 Hz.

Treating disorders related to a hypoarousal of the autonomic nervous system may include obtaining input of a hypoarousal disorder and a subject's sensory threshold for transcutaneous vibratory output. The input of the hypoarousal disorder may be obtained with a user interface in communication with a processor. Alternatively, input of the hypoarousal disorder may be obtained through sensed data or third party data. The user's sensory threshold is determined as described herein. Based on the hypoarousal disorder, the processor may select a stimulation pattern for transcutaneous vibratory output to be emitted by a transducer of a stimulation device, the stimulation pattern having parameters comprising a perceived pitch, a perceived beat, and a perceived intensity. The computer processor may cause the transducer to generate the transcutaneous vibratory output in the selected stimulation pattern at a sensory threshold value at or above the subject's sensory threshold for transcutaneous vibratory output.

Examples of perceived pitch and perceived beat used to treat certain hypoarousal disorders are provided herein:

Treatment of depression may include the application of a perceived pitch of about 10 Hz or more and a perceived beat that is equal to or greater than about 0.05 Hz, optionally at an intensity within 2 standard deviations of the user's sensory threshold. In embodiments, anti-depressive pharmaceutical compounds and/or mindfulness activities may be used in conjunction with stimulation to treat depression.

Treatment of fatigue, narcolepsy, excessive daytime somnolence, chronic fatigue syndrome, and the like may include the application of a perceived pitch of 40 Hz or more and a perceived beat that is equal to or greater than about 0.1 Hz, optionally at an intensity within the upper 2 standard deviations of the user's sensory threshold.

Treatment of catatonia may include the application of a perceived pitch of about 10 Hz or more and a perceived beat that is equal to or greater than about 0.01 Hz, optionally at an intensity within 1 standard deviation of the user's sensory threshold.

Treatment of constipation may include the application of a perceived pitch of about 20 Hz or more and a perceived beat that is equal to or greater than about 0.05 Hz, optionally at an intensity within the upper 2 standard deviations of the user's sensory threshold.

Treatment of attention deficit disorder and other attention and concentration issues may include the application of a perceived pitch of about 40 Hz or more and a perceived beat that is equal to or greater than about 0.1 Hz, optionally at an intensity within 1 standard deviation of the user's sensory threshold.

Treatment of disorders of metabolism including insulin insensitivity (i.e. type 2 diabetes mellitus) and metabolic syndrome may include the application of a perceived pitch of about 10 Hz or more and a perceived beat that is equal to or greater than 0.001 Hz, optionally at an intensity within 2 standard deviations of the user's sensory threshold.

Treatment of hypotension and dysautonomia may include the application of a perceived pitch of about 20 Hz or more and a perceived beat that is equal to or greater than 0.001 Hz, optionally at an intensity within the upper 2 standard deviations of the user's sensory threshold.

To decrease symptoms of hyperarousal disorders, these layered oscillations may start at a higher frequency that corresponds to a current energy level of the user, and taper down to slower oscillations that correspond to an upper threshold level of energy associated with deep relaxation and/or somnolence (the goal state in this case). For example, the perceived pitch may start at a starting value (such as 100 Hz) that is established by any suitable means, such as by being a default, or based on a user-selectable input, or based on the user's response to certain questions such as "how do you feel," or based on data collected from the user's mobile electronic device and/or a wearable device having sensors such as accelerometers. Different inputs may be associated with different starting values, such as by a lookup table, or by an algorithm that considers combinations of input details. In general, for sleep applications, in some embodiments the starting value of the perceived pitch would not be greater than 200 Hz.

In one embodiment, the perceived pitch could then decrease from the starting value (e.g. 200 Hz) at a rate of approximately 5-10 Hz every 10-20 seconds (approximately) until it reaches an upper threshold (such as approximately 40 Hz) level. The perceived pitch may remain at the upper threshold for a holding period (stabilization phase), such as approximately 60 seconds. The perceived pitch may then decrease at a rate of approximately 1 Hz every 10 seconds (approximately) until it reaches a second threshold (stabilization phase) that is less than the first threshold (such as approximately 30 Hz, or approximately 75% of the first threshold). The perceived pitch may remain at the second threshold for the holding period. After that, the perceived pitch may decrease at a rate of approximately 1 Hz every 10 seconds (approximately) until it reaches a third threshold that is lower than the second threshold (such as 20 Hz, or approximately 50% of the upper threshold) and remain at 20 Hz for an effective period (such as approximately 20 minutes). This effective period may be determined in part by the software time limits (minimum: 5 minutes/maximum: 60 minutes) and/or in part by the user.

During this process, the perceived beat may start at a first level (such as 0.2 Hz) and decrease by a rate of approximately 0.025 Hz every 15 seconds until it reaches approximately 0.1 Hz. The perceived beat may remain at approximately 0.1 Hz for approximately 120 seconds. The perceived beat may then decrease by approximately 0.01 Hz every 30 seconds until it reaches the desired frequency to achieve desired results (e.g., approximately 0.05 Hz). The perceived beat may remain at 0.05 Hz for the effective period (such as up to 20 minutes) or until the perceived pitch changes.

By way of examples, a perceived pitch starting at approximately 100 Hz may be available as an option with the longest/slowest taper (e.g., a 60-minute cycle), approximately 40 Hz may be considered to be an average starting point for the perceived pitch (e.g., a 30-minute cycle), and approximately 33 Hz may be considered to be the perceived pitch's starting point for the shortest/fastest taper (e.g., a 10-minute cycle). Similarly, the perceived pitch and the perceived beat may also taper independently or in tandem. One iteration of this for rapid relaxation could have the perceived pitch starting at 200 Hz and tapering to 40 Hz over the course of 5 minutes and then stabilizing at 40 Hz for another 10 minutes, while the perceived beat starts at 2 Hz and tapers to 0.1 Hz gradually over 15 minutes. In each case, the value of the difference may taper over time so that the primary and secondary oscillations are very close together, such as a difference of approximately 0.0001 Hz, before each frequency reaches zero. Optionally, the perceived beat's tapers may have a longer period than the perceived pitch's taper because they may take the user through more arousal states prior to finally arriving at the desired effect, especially if the user was more symptomatic prior to using the device. In general, for each frequency, the greater the speed of the taper (the less time spent in each frequency state), the quicker the user is likely to transition from symptomatic to asymptomatic. Specific combinations may include, for example: (A) a perceived pitch starting at approximately 100 Hz and tapering down to 20 Hz until shut-off, with a perceived beat that initially differs from the primary by approximately 1 Hz, with the difference tapering down to 0.01 Hz over time; (B) a perceived pitch starting at approximately 40 Hz and tapering down to 10 Hz until shut-off, with a perceived beat that initially differs from the primary by approximately 0.2 Hz, with the difference tapering down to 0.001 Hz over time until shut-off; and (C) a perceived pitch starting at approximately 33 Hz and tapering down to 1 Hz until shut-off, with a perceived beat that initially differs from the primary by approximately 0.1 Hz, with the difference tapering down to 0.0001 Hz over time until shut-off.

Similarly, in some applications that take advantage of the alternative embodiment of layering sine waves to produce an interference pattern, the primary frequency may be about 1-200 Hz and the modulation frequency may be about 0.0001-4 Hz different from the primary frequency (e.g., for treatment of disorders relating to hyperarousal such as sleep disorders, chronic pain, post-traumatic stress disorder, chronic stress, autism, autoimmune disorders, anxiety, hypertension, or the like that are characterized by increased activity of the sympathetic nervous system over time). In some embodiments, the perceived beat is generated in part by a primary frequency of (or starting at) a level that is from 10 to 200 Hz, with a secondary frequency that differs from the primary frequency by 0.0001 or more.

Examples may include, without limitation:

Treatment of chronic pain may include the application of a main frequency of about 100 Hz or less and a modulation frequency that is equal to or less than about 0.2 Hz different from the primary frequency, optionally at an intensity within 1 standard deviation of the medians of user's sensory threshold.

Treatment of chronic stress may include the application of a main frequency of 200 Hz or less and a modulation frequency that is equal to or less than about 4 Hz different from the primary frequency, optionally at an intensity 1 standard deviation of the medians of user's sensory threshold.

Treatment of autism may include the application of a main frequency of about 200 Hz or less and a modulation frequency that is equal to or less than about 4 Hz different from the primary frequency, optionally at an intensity within 2 standard deviations of the medians of user's sensory threshold.

Treatment of autoimmune disorders may include the application of a main frequency of about 200 Hz or less and a modulation frequency that is equal to or less than about 1 Hz different from the primary frequency, optionally at an intensity within 1 standard deviation of the medians of the user's sensory threshold.

Treatment of anxiety may include the application of a main frequency of about 200 Hz or less and a modulation frequency that is equal to or less than 4 Hz different from the primary frequency, optionally at an intensity within 1 standard deviation of the medians of user's sensory threshold.

Treatment of hypertension may include the application of a main frequency of about 100 Hz or less and a modulation frequency that is equal to or less than 4 Hz different from the primary frequency, optionally at an intensity within 1 standard deviation of the medians of user's sensory threshold.

In certain other applications, the main frequency may be about 40-500 Hz and the modulation frequency may be about 0.1-10 Hz different from the primary frequency (e.g., for treatment of disorders relating to hypoarousal such as depression, narcolepsy, fatigue, constipation, catatonia, metabolic syndrome, eating disorders, hypotension, attention disorders that are characterized by decreased or unbalanced activity of the sympathetic nervous system over time). In some embodiments, treatment of disorders relating to hypoarousal may use a primary frequency of (or starting at) a level that is between 40 Hz to 200 Hz, with a secondary frequency that differs from the primary frequency by 0.1-10 Hz. The perceived beat of the stimulation is generated in part by the difference in the primary and secondary frequency.

Continuing with examples, the examples may include, without limitation:

Treatment of depression may include the application of a main frequency of about 40 Hz or more and a modulation frequency that is equal to or greater than about 0.1 Hz-4 Hz different from the primary frequency, optionally at an intensity within the upper 2 standard deviations of the medians of user's sensory threshold.

Treatment of fatigue, narcolepsy, excessive daytime somnolence, chronic fatigue syndrome, and the like may include the application of a main frequency of 89 Hz or more and a modulation frequency that is equal to or greater than about 0.1 Hz different from the primary frequency, optionally at an intensity within the upper 2 standard deviations of the medians user's sensory threshold.

Treatment of catatonia may include the application of a main frequency of about 10 Hz or more and a modulation frequency that is equal to or greater than about 0.1 Hz different from the primary frequency, optionally at an intensity within 1 standard deviation of the medians of user's sensory threshold.

Treatment of constipation may include the application of a main frequency of about 20 Hz or more and a modulation frequency that is equal to or greater than about 0.1 Hz different from the primary frequency, optionally at an intensity within the upper 2 standard deviations of the medians of user's sensory threshold.

Treatment of attention deficit disorder and other attention and concentration issues may include the application of a main frequency of about 40 Hz or more and a modulation frequency that is equal to or greater than about 0.1 Hz different from the primary frequency, optionally at an intensity within 1 standard deviation of the medians of user's sensory threshold.

Treatment of disorders of metabolism including insulin insensitivity (type 2 diabetes mellitus) and metabolic syndrome may include the application of a main frequency of about 40 Hz or more and a modulation frequency that is equal to or greater than 0.1 Hz different from the primary frequency, optionally at an intensity within 2 standard deviations of the medians of user's sensory threshold.

Treatment of hypotension and dysautonomia may include the application of a main frequency of about 60 Hz or more and a modulation frequency that is equal to or greater than 0.1 Hz different from the primary frequency, optionally at an intensity within the upper 2 standard deviations of the medians of user's sensory threshold.

To decrease symptoms of hyperarousal disorders, the oscillations may start at a higher frequency that corresponds to a current energy level of the user, and taper to a frequency that corresponds to an upper threshold level of energy associated with deep relaxation and/or somnolence. For example, the primary frequency may start at a starting value (such as 100 Hz) that is established by any suitable means, such as by being a default, or based on a user-selectable input, or based on the user's response to certain questions such as "how do you feel," or based on data collected from the user's mobile electronic device and/or a wearable device having sensors such as accelerometers. Different inputs may be associated with different starting values, such as by a lookup table, or by an algorithm that considers combinations of input details. In general, for sleep applications, in some embodiments the starting value of the primary frequency would not be greater than 100 Hz.

The primary frequency may then decrease from the starting value at a rate of approximately 5-10 Hz every 20 seconds (approximately) until it reaches the upper threshold level (such as approximately 40 Hz). The primary frequency may remain the upper threshold for a holding period, such as approximately 60 seconds. The primary frequency may then decrease at a rate of approximately 1 Hz every 10 seconds (approximately) until it reaches a second threshold that is less than the first threshold (such as approximately 30 Hz, or approximately 75% of the first threshold). The primary frequency may remain at the second threshold for the holding period. After that, the primary frequency may decrease at a rate of approximately 1 Hz every 10 seconds (approximately) until it reaches a third threshold that is lower than the second threshold (such as 20 Hz, or approximately 50% of the upper threshold) and remain at 20 Hz for an effective period (such as approximately 20 minutes). This effective period may be determined in part by the software time limits (minimum: 5 minutes/maximum: 60 minutes) and/or in part by the user.

During this process, the secondary frequency may start at a first level (such as 0.2 Hz) and decrease by a rate of approximately 0.025 Hz every 15 seconds until it reaches approximately 0.1 Hz. The secondary frequency may remain at approximately 0.1 Hz for approximately 120 seconds. The secondary frequency may then decrease by approximately 0.01 Hz every 30 seconds until it reaches the desired frequency to relieve symptoms (e.g., approximately 0.05 Hz). The secondary frequency may remain at 0.01 Hz for the effective period (such as up to 20 minutes) or until the primary frequency changes.

By way of examples, a primary frequency starting at approximately 100 Hz may be available as an option with the longest/slowest taper (e.g., a 60-minute cycle), approximately 40 Hz may be considered to be an average starting point for the primary frequency (e.g., a 30-minute cycle), and approximately 33 Hz may be considered to be the primary frequency's starting point for the shortest/fastest taper (e.g., a 10-minute cycle). Similarly, the difference between the primary frequency and the secondary frequency (i.e., the modulation frequency) may also taper, such as starting at a difference from the primary frequency of approximately >2 Hz=longest taper; starting at a difference of approximately 0.2-2 Hz=moderate taper; and starting at a difference of approximately <0.2 Hz=shortest taper. In each case, the value of the difference may taper over time so that the primary and secondary oscillations are very close together, such as a difference of approximately 0.0001 Hz, before each frequency reaches zero. Optionally, the secondary frequency's tapers may have a longer period than the primary frequency's taper because they may take the user through more arousal states prior to finally arriving at the desired effect, especially if the user was more symptomatic prior to using the device. In general, for each frequency, the greater the speed of the taper (the less time spent in each frequency state), the quicker the user is likely to transition from symptomatic to asymptomatic. Specific combinations may include, for example: (A) a primary frequency starting at approximately 100 Hz and tapering down to 20 Hz until shut-off, with a secondary frequency that initially differs from the primary by approximately 1 Hz, with the difference tapering down to 0.01 Hz over time; (B) a primary frequency starting at approximately 40 Hz and tapering down to 10 Hz until shut-off, with a secondary frequency that initially differs from the primary by approximately 0.2 Hz, with the difference tapering down to 0.001 Hz over time until shut-off; and (C) a primary frequency starting at approximately 33 Hz and tapering down to 1 Hz until shut-off, with a secondary frequency that initially differs from the primary by approximately 0.1 Hz, with the difference tapering down to 0.0001 Hz over time until shut-off.

Similarly, to decrease symptoms of hypoarousal disorders, the oscillations may start at a lower frequency that corresponds to a current energy level of the user, and increase to a frequency that corresponds to a threshold level of energy associated with energizing a user. For example, the primary frequency may start at a starting value (such as 40 Hz) that is established by any suitable means, such as by being a default, or based on a user-selectable input, or based on the user's response to certain questions such as "how do you feel," or based on data collected from the user's mobile electronic device and/or a wearable device having sensors such as accelerometers. Different inputs may be associated with different starting values, such as by a lookup table, or by an algorithm that considers combinations of input details.

The primary frequency may then increase from the starting value at a rate of approximately 5-10 Hz every 20 seconds (approximately) until it reaches the upper threshold level (such as approximately 40 Hz). The primary frequency may remain at the upper threshold for a holding period, such as approximately 60 seconds. The primary frequency may then increase at a rate of approximately 1 Hz every 10 seconds (approximately) until it reaches a second threshold that is greater than the first threshold (such as approximately 600 Hz). The primary frequency may remain at the second threshold for the holding period. After that, the primary frequency may increase at a rate of approximately 1 Hz every 10 seconds (approximately) until it reaches a third threshold that is higher than the second threshold (such as 100 Hz) and remain at 100 Hz for an effective period (such as approximately 20 minutes). This effective period may be determined in part by the software time limits (minimum: 5 minutes/maximum: 60 minutes) and/or in part by the user.

During this process, the secondary frequency may start at a first level (such as 0.2 Hz) and increase by a rate of approximately 0.025 Hz every 15 seconds until it reaches approximately 1 Hz. The secondary frequency may remain at approximately 1 Hz for approximately 120 seconds. The secondary frequency may then decrease by approximately 0.01 Hz every 30 seconds until it reaches the desired frequency to relieve symptoms (e.g., approximately 5 Hz). The secondary frequency may remain at 5 Hz for the effective period (such as up to 20 minutes) or until the primary frequency changes.

The stimulation works by increasing the balance between the sympathetic and parasympathetic components of the autonomic nervous system, which is required for optimal functioning of the human body. One way in which the stimulation device 102 may deliver treatment therapy is by acoustic and/or vibration induced stimulation to increase parasympathetic activity, inhibit sympathetic activity, increase sympathetic activity, and/or inhibit parasympathetic activity, collectively referred to as modulation of the autonomic nervous system. The above frequency ranges are provided for example purposes only and may be adjusted or tuned for a subject based on the subject's physiological reactions using a feedback loop, as described below. Specifically, the above frequencies may be personalized to a subject based on biometric data collected by the sensor device 118 (e.g., heart rate, heart rate variability, blood pressure, respirations, sweat level, resting pulse rate, brain activity, etc.) and/or based on user feedback.

In general, the increase in parasympathetic and sympathetic nervous system balance that results from the application of low frequency sound (or vibration) is perceptible and can be monitored in real time, thereby permitting careful monitoring of the result, and modulation, control or withdrawal of the stimulation as necessary. In certain embodiments, the results may be presented to a subject by, for example, the user interface and/or via an application on a user device. Furthermore, a treatment plan may be designed in which either continuous or pulsed delivery of low frequency sound is carried out over a period of days, weeks, months, or even years, depending on the particular circumstances of the subject being treated.

Therapeutic stimulation may facilitate entry into a sleep state. Most people experience difficulty falling asleep and/or staying asleep at some point in their lives. Sleeplessness may occur in reaction to stressful events in a person's life, during travel when normal body rhythms are disrupted, in response to the person engaging in stimulating activities before bedtime, or for other reasons. Many people repeatedly experience sleeplessness over multiple nights during a week, and such a condition may be considered to be acute insomnia. If this pattern continues over multiple months, it may be considered to be chronic insomnia.

It has been estimated that 25 to 30 percent of humans experience acute insomnia each year. Because of this, many treatments are offered to help treat insomnia. These treatments range from pharmaceutical treatments such as benzodiazepine and non-benzodiazepine sedatives as well as natural interventions. Many pharmaceutical treatments can cause unwanted side effects, must be monitored for interaction with other drugs, and can cause sleepiness to continue past the person's desired sleep time. Non-pharmaceutical treatments, such as bright light therapy and cognitive behavioral therapy, can be time-consuming and require a significant amount of self-discipline by the person to continue the course of therapy. Accordingly, better ways of treating insomnia and other forms of sleeplessness are desired.

This disclosure provides a method and system for treating sleeplessness by applying and removing vibratory or sonic stimulation to the human body in a pattern that increases balance between the sympathetic and parasympathetic components of the autonomic nervous system. The stimulation may improve parasympathetic nervous system activity, thereby balancing activity in the autonomic nervous system, by activating afferent sensory nerve fibers in the skin and deep tissue that network with the parasympathetic nervous system in the spinal cord and brain, to include the Vagus nerve and its collaterals as a primary component. This improvement in parasympathetic activity results in a reduction of aberrant or unwanted activity in the sympathetic nervous system activity.

Terminology that is relevant to this disclosure includes the term "sleeplessness". Sleeplessness includes general physical conditions in which a person exhibits an inability to fall asleep and/or to remain asleep for more than a brief period of time (such as only one to three hours). "Insomnia" refers to a condition in which a person experiences sleeplessness multiple nights per week. Chronic insomnia is insomnia that occurs at least three nights per week and lasts at least three months. Insomnia that persists for a lesser period of time may be considered to be acute insomnia.

To induce deep relaxation and/or somnolence leading to sleep in a subject who is awake, the transcutaneous vibratory output may start at a higher frequency/pitch/beat/intensity that corresponds to a current energy level of the user, and taper to a frequency/pitch/beat/intensity that corresponds to an upper threshold level of energy associated with deep relaxation and/or somnolence. For example, the primary frequency or perceived pitch may start at a starting value that is established by any suitable means, such as by being a default, based on a user-selectable input, based on the user's response to certain questions such as "how do you feel," or based on data collected from the user's mobile electronic device and/or a wearable device having sensors such as accelerometers. Different inputs may be associated with different starting values, such as by a lookup table, or by an algorithm that considers combinations of input details.

In some embodiments, transcutaneous vibratory output may be caused to commence automatically, such as at a certain time or in response to a sensor worn by or in proximity to the user providing data to a processor indicating that they are in a pre-sleep state. For example, an accelerometer may indicate slowing or no motion indicating a readiness for sleep.

Figure 14:
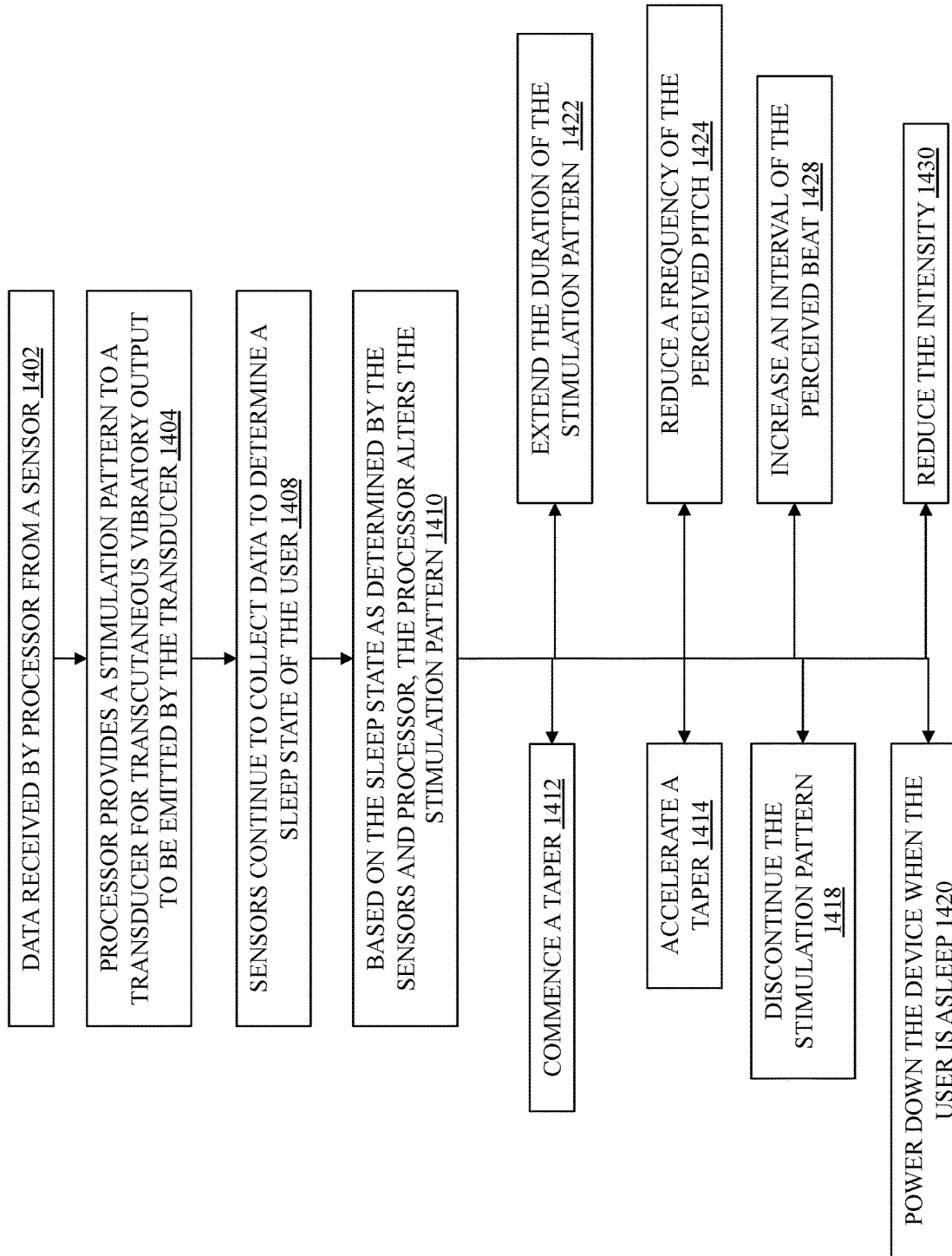
FIG. 14 depicts a process for operating a stimulation device.

Referring to FIG. 14, upon receiving the data 1402, the processor may provide to a transducer a stimulation pattern 1404 for transcutaneous vibratory output to be emitted by the transducer. The stimulation pattern may have parameters comprising a perceived pitch, a perceived beat, and a perceived intensity. In some embodiments, the stimulation pattern may comprise a perceived pitch between 1-100 Hz and a perceived beat at a second frequency between 0.0001 and 1.5 Hz. In other embodiments, the perceived beat is generated in part by a first oscillation at a first frequency that is in the range of 1-100 Hz, and a second oscillation at a second frequency that differs from the first frequency by 0.0001 to 1.5 Hz. The sensors may continue to collect data 1408 to determine a sleep state of the user (e.g. pre-sleep, almost asleep, asleep). Based on the sleep state as determined by the sensors, the processor may alter 1410 the stimulation pattern, such as to commence a taper 1412, accelerate a taper 1414, discontinue the stimulation pattern 1418 or power down the device 1420 when the user is asleep, extend the duration of the stimulation pattern 1422, or the like. Altering the stimulation pattern may also include at least one of (i) reducing a frequency of the perceived pitch 1424, (ii) increasing an interval of the perceived beat 1428, or (iii) reducing the intensity 1430. In some embodiments, the stimulation pattern may be matched to the sleep state. For example, if the accelerometers indicate a slowing in activity but other indicators suggest the user is ready for sleep but not asleep yet, particular relaxing frequencies may begin to be emitted to ease the eventual transition to sleep.

When a frequency of the perceived pitch is reduced to a first reduced perceived pitch, the first reduced perceived pitch may be maintained for a selected period of time or until sensors indicate a change in the user's sleep state that may require another alteration in the stimulation pattern. For example, if the sensor indicates that the user has reached the almost asleep state, a second alteration of the stimulation pattern may be triggered and the first reduced perceived pitch may be reduced to a second reduced perceived pitch which may be maintained for a selected period of time or until sensors indicate a change in the user's sleep state that may require another alteration in the stimulation pattern. For example, during sleep, an accelerometer may sense motion during a bad dream and a stimulation pattern may be triggered to encourage re-entry into a sleep state.

When an interval of the perceived beat is reduced to a first increased perceived beat, the first reduced perceived beat may be maintained for a selected period of time or until sensors indicate a change in the user's sleep state that may require another alteration in the stimulation pattern. For example, if the sensor indicates that the user has reached the almost asleep state, a second alteration of the stimulation pattern may be triggered and the first reduced perceived beat may be reduced to a second reduced perceived beat which may be maintained for a selected period of time or until sensors indicate a change in the user's sleep state that may require another alteration in the stimulation pattern.

When an intensity is reduced to a first reduced intensity, the first reduced intensity may be maintained for a selected period of time or until sensors indicate a change in the user's sleep state that may require another alteration in the stimulation pattern. For example, if the sensor indicates that the user has reached the almost asleep state, a second alteration of the stimulation pattern may be triggered and the first reduced intensity may be reduced to a second reduced intensity which may be maintained for a selected period of time or until sensors indicate a change in the user's sleep state that may require another alteration in the stimulation pattern.

For example, a perceived pitch starting at approximately 100 Hz may be available as an option with the longest/slowest taper (e.g., a 30-minute cycle), approximately 40 Hz may be considered to be an average starting point for the perceived pitch (e.g., a 20-minute cycle), and approximately 30 Hz or approximately 33 Hz may be considered to be the perceived pitch's starting point for the shortest/fastest taper (e.g., a 10-minute cycle). Similarly, the perceived beat may also taper independently of the perceived pitch, such as starting at approximately 0.2-1 Hz for the longest taper; starting at approximately 0.1-0.2 Hz for a moderate taper; and starting at 0.05-0.1 Hz for the shortest taper. In each case, the frequency of the perceived pitch and/or perceived beat may taper over time. Optionally, the perceived beat's tapers may have a longer period than that of the perceived pitch because they may take the user through more arousal states prior to finally arriving at sleep, especially if the user was more energized/awake prior to using the device. In general, for each frequency, the greater the speed of the taper (the less time spent in each frequency state), the quicker the user is likely to transition from awake to sleep. Specific combinations may include, for example: (A) a perceived pitch starting at approximately 100 Hz and tapering down to 1 Hz until shut-off, with a perceived beat starts at 1 Hz tapering down to 0.0001 Hz over time; (B) a perceived pitch starting at approximately 40 Hz and tapering down to 1 Hz until shut-off, with a perceived beat starting at approximately 0.2 Hz tapering down to 0.0001 Hz over time until shut-off; and (C) a perceived pitch starting at approximately 33 Hz and tapering down to 1 Hz until shut-off, with a perceived beat of approximately 0.1 Hz tapering down to 0.0001 Hz over time until shut-off.

In the alternative embodiment of layered sine waves generating an interference pattern, the primary frequency may decrease from a starting value, such as 100 Hz, until it reaches the upper threshold level (such as approximately 40 Hz). The rate at which the stimulation is tapered may be programmed. For example, the tapering rate may be a rate of approximately 5-10 Hz every 20 seconds. The primary frequency may remain at the upper threshold for a holding period, such as approximately 60 seconds. The primary frequency may then decrease (e.g. at a rate of approximately 1 Hz every 10 seconds) until it reaches a second threshold that is less than the first threshold (such as approximately 30 Hz, or approximately 75% of the first threshold). The primary frequency may remain at the second threshold for the holding period. After that, the primary frequency may decrease (e.g. at a rate of approximately 1 Hz every 10 seconds) until it reaches a third threshold that is lower than the second threshold (such as 10 Hz, or approximately 25% of the upper threshold) and remain at the third threshold for a sleep period (such as approximately 20 minutes).

Continuing with the embodiment of layered sine waves generating an interference pattern, during this process, a secondary frequency may start at a first level (such as 0.2 Hz) and decrease (e.g. by a rate of approximately 0.025 Hz every 15 seconds) until it reaches a second level, such as approximately 0.1 Hz in this example. The secondary frequency may remain at the second level for a duration (e.g. approximately 240 seconds). The secondary frequency may then decrease (e.g. such as at a rate of approximately 0.01 Hz every 30 seconds) until it reaches the desired frequency for sleep (e.g., approximately 0.01 Hz). The secondary frequency may remain at the desired frequency for the sleep period (such as up to 20 minutes) or until the primary frequency changes.

By way of example, and continuing with the embodiment of layered sine waves generating an interference pattern, a primary frequency starting at approximately 100 Hz may be available as an option with the longest/slowest taper (e.g., a 30-minute cycle), approximately 40 Hz may be considered to be an average starting point for the primary frequency (e.g., a 20-minute cycle), and approximately 30 Hz or approximately 33 Hz may be considered to be the primary frequency's starting point for the shortest/fastest taper (e.g., a 10-minute cycle). Similarly, the difference between the primary frequency and the secondary frequency (i.e., the modulation frequency) may also taper, such as starting at a difference from the primary frequency of approximately 0.2-1 Hz for the longest taper; starting at a difference of approximately 0.1-0.2 Hz for a moderate taper; and starting at a difference of approximately 0.05 Hz for the shortest taper. In each case, the value of the difference may taper over time so that the primary and secondary oscillations may be very close together, such as a difference of approximately 0.0001 Hz, before each frequency reaches zero. Optionally, the secondary frequency's tapers may have a longer period than the primary frequency's taper because they may take the user through more arousal states prior to finally arriving at sleep, especially if the user was more energized/awake prior to using the device. In general, for each frequency, the greater the speed of the taper (the less time spent in each frequency state), the quicker the user is likely to transition from awake to sleep. Specific combinations may include, for example: (A) a primary frequency starting at approximately 100 Hz and tapering down to 1 until shut-off, with a secondary frequency that initially differs from the primary by approximately 1 Hz, with the difference tapering down to 0.0001 Hz over time; (B) a primary frequency starting at approximately 40 Hz and tapering down to 1 until shut-off, with a secondary frequency that initially differs from the primary by approximately 0.2 Hz, with the difference tapering down to 0.0001 Hz over time until shut-off; and (C) a primary frequency starting at approximately 33 Hz and tapering down to 1 until shut-off, with a secondary frequency that initially differs from the primary by approximately 0.1 Hz, with the difference tapering down to 0.0001 Hz over time until shut-off. In embodiments, the first oscillation of two or more oscillations may exhibit a first frequency having a starting value that is in the range of approximately 1 to approximately 100 Hz, and a second oscillation of two or more oscillations may exhibit a second frequency initially differs from the first frequency by approximately 0.0001 to approximately 1 Hz. The two or more oscillations collectively form a beat output.

In some embodiments, the user interface of the system may include an input field in which a user can select modes that will increase or decrease the speed by which the frequencies taper from the upper starting point to the lower ending point. For example, a user who wants to fall asleep very quickly may select a mode in which the frequencies taper on the more rapid end of the spectrum, while those who are winding down (de-escalating) more slowly or who are more highly energized before bed may choose to have a frequency taper on the more delayed end of the spectrum. The user may make this selection by a slider or dial, by entering numeric values, or by selecting from one of various modes (in which each mode will have various times and thresholds assigned to it).

In some embodiments, as the frequency of the vibration tapers down, the intensity of the vibration is also tapered from a more intense value to a less intense value or the opposite. That is to say that each frequency, the perceived pitch, the perceived beat, and the perceived intensity can be modulated independently of one another. The device may do this by decreasing the current applied to the transducer's coil as the device also reduces the sonic emissions' frequencies. The intensity of the oscillations may start at the upper end of a sensory threshold (at which the user would have a harder time ignoring the vibration). The intensity may then decrease to a barely detectable level (at the bottom end of the sensory threshold) over a first period (such as approximately 15 minutes) at a rate (e.g. approximately 10% per minute). The rate may be measured from the level that existed during the previous minute. The intensity may remain at the final level for the remaining duration of stimulation (e.g., for another 15-25 minutes). Shorter time periods may be used if fewer thresholds are used. In other embodiments, the intensity of the stimulus may remain at or within 1 standard-deviation of the medians of users' sensory threshold to provide the desired results.

The stimulation may automatically turn off after a period of time, such as after the primary frequency has been applied at its lowest level, or after the total cycle (from starting value to lowest level) has been applied for a period (e.g. at least 30 minutes). Other time values may be used to trigger the automatic shut-off. The sonic vibration may remain on for a longer period associated with a desired rest or treatment period (such as 6 hours, 7 hours or 8 hours), or can continue until the user wakes up and turns the vibration off. Optionally, the system may default to shutting off after an initial cycle (such as 20-30 minutes) unless a sensor device that is in communication with the stimulation device 102 or its controller provides data showing that the user is not yet reached a desired measurable biometric state (such as a target breathing rate, heart rate, pulse, movement, etc.). Such data may include data from a body movement sensor worn by the user indicating that the user is moving or has moved more than a threshold level during a specified period of time just before the end of the sleep cycle (e.g., 1 minute before the end of the sleep cycle, 3 minutes before the end of the sleep cycle, etc.). The body movement sensor may also indicate that the user is no longer moving, which may be an indication that the user has fallen asleep, and the stimulation may be discontinued, tapered down at a faster rate, or switched immediately to a level for sleep maintenance.

Optionally, the sonic vibrations may be initiated within 1 hour before the user desires to fall asleep. However, the stimulation may begin to induce states of relaxation and somnolence in as little as three minutes. The stimulation may be effective when the primary frequency's is applied in combination with the modulation frequency for a duration, such as at least 15 minutes. In some embodiments, a sleep mode may apply the stimulation for a pre-determined duration (e.g. 30-40 minutes). The system may enable the user to select the duration of the program in some embodiments.

In an aspect, a method of delivering and tapering a user stimulation may include tapering a first oscillation (also known as main frequency or base tone) down from an upper threshold frequency to a lower threshold frequency over a first period of time, and maintaining the first oscillation/base tone at the lower threshold frequency during a second period of time (e.g. 5 min). Tapering may utilize a first tapering rate to taper the first oscillation/base tone down to a target frequency (e.g. 100 Hz, 40 Hz, 33 Hz, 30 Hz, 1 Hz, or the like), and when the first oscillation/base tone reaches the target frequency changing the tapering rate to a second tapering rate when tapering the first oscillation/base tone from the target frequency to the lower threshold frequency (e.g. 40 Hz, 33 Hz, 30 Hz, 1 Hz, or the like). In embodiments, the first oscillation/base tone target frequency may be any frequency, such as a frequency chosen from 0.1 Hz to 100 Hz (e.g. 100 Hz, 40 Hz, 33 Hz, 30 Hz, 1 Hz, or the like). The stimulation device 102 may emit a beat output as vibrations that correspond to the therapeutic stimulation pattern which may include starting the second oscillation (also known as modulation frequency or perceived beat frequency) at a first threshold frequency, tapering the second oscillation down to a second threshold frequency over the first period of time, and maintaining the second oscillation at the second threshold frequency during the second period of time. The tapering rate may be user-customizable and adjustable. The upper threshold frequency may be user-set based on a current activity, a current user-indicated feeling, a desired feeling, a lookup table, or by an algorithm that considers combinations of input details.

In an embodiment, the duration of the taper cycle may vary with the starting oscillation. For example, the taper cycle may be 30 min, 20 min, 10 min, or the like. In an embodiment, the modulation frequency may also be tapered, such as described herein with respect to the primary frequency. For example, the modulation frequency or the perceived beat may start at approximately 1 Hz for the longest taper; at approximately 0.1-0.2 Hz for a moderate taper; or at approximately 0.05 Hz for the shortest taper.

In an embodiment, the value of the difference between main and modulation frequency may be tapered over time so that they are very close together before each frequency reaches zero. In some embodiments, the secondary, or modulation, frequency's tapers may have a longer period than the primary frequency's taper. In an embodiment, a shut-off may be triggered after a specific period of time or after the primary frequency has been applied at its lowest level for a period of time.

In an embodiment, based on a desired target state of a user, a first transcutaneous vibratory output comprising parameters including a first perceived pitch, a first perceived beat, and a first perceived intensity is generated for application to a body portion of a user. A value of one or more of the first perceived pitch, the first perceived beat, and the first perceived intensity begins at an upper value, and depending on the stimulation protocol needed to reach the desired target state, the first transcutaneous vibratory output may be tapered by tapering the one or more of the first perceived pitch, the first perceived beat, and the first perceived intensity down to a lower value over a first period of time. The lower value may be maintained during a second period of time. A first tapering rate may be used to taper the first perceived pitch or the first perceived beat down to a target frequency before the lower value. After reaching the target frequency, tapering or the stimulation may be discontinued, such as if sensors indicate a target state has already been reached, or a second tapering rate may be used to taper from the target frequency to a lower value. As many segments of tapering to incrementally lower values at the same or a different tapering rate may be used in order to reach the lower value.

In embodiments, the therapeutic stimulation may increase from a starting value and ramp up to a target value. For example, one or more of the perceived pitch, perceived beat frequency, or intensity may be ramped up from a starting value to a target value. The starting value may be a lower threshold frequency. The target value may be selected to correspond with a therapeutic goal, may be an upper threshold frequency, or the like. Ramping up may be done via a rate over a period of time, wherein the rate itself may be variable or ramped in speed. As many segments of ramping up to incrementally higher values at the same or a different ramping rate may be used in order to reach the highest value. In embodiments, once the target value is reached, it may be maintained for a second period of time or until it is caused to be terminated or tapered down, such as in response to sensor feedback or via a manual input.

In an embodiment, the system may be able to predict the onset of a state for a user, such as an emotional state. Various emotional states include anger, fear, annoyance, sadness, anxiety, apathy, frustration, distracted, or the like. Predicting the onset of the state may cause the system to address the user's current state or avoid the predicted state. Addressing or avoiding may involve a stimulation protocol being triggered, such as a stimulation directed at mitigating the onset of the state or treating the state. The user's predicted state may be determined by electronically sensing at least one of a physiological state of the user or a contextual data of the user. In some embodiments, the predicted state may be determined by electronically sensing the physiological state of the user and collecting the contextual data of the user. The physiological state may be sensed with a sensor of a wearable device. Information from the sensing wearable and/or third-party sources (e.g. social media) may be used to determine the user's condition, and coordinate delivery of appropriate stimulation therapy.

In an example, the sensor may determine HRV. In another example, the sensor may be an audio sensor that senses vocal data, such as a yawn, a sigh, a yell, a vocal pitch, a vocal tone, a speaking speed, a vocal volume, an acoustic characteristic, or the like. The contextual data may be sensed or collected from a device separate from the wearable device (e.g. smartphone, fitness monitor, smart watch, smart speaker, smart eyewear, connected vehicle, smart headphones, etc.), a social media platform, an environmental sensor, third party data, or the like. For example, social media posts may be analyzed to derive indicative of a mood of the user (e.g. negative, positive, frustration, anger, anxiety, distracted, etc.). In another example of contextual data, the user's movement or location data may be sensed or collected, such as from a mobile device of the user. The system may determine if the user's location is indicative, or predictive, of the mood of the user. Other contextual user data may include calendar entries, project management entries, social media content, screen time, or a current sensed activity (e.g. flying, commuting, in traffic) to modify an aspect of the stimulation, trigger, or discontinue the stimulation. In embodiments, various metrics of user activity may be extrapolated from the contextual user data, optionally in combination with other data, to obtain a signature of data associated with the user for when they feel that life is great (which may be a goal or target state for the user), when they feel poorly, or any state in between. This life signature, which may be a personalized goal state, may be monitored by the system to predict when the user's overall mood or feeling of well-being is beginning to decline, such as when their life signature begins to move away from great and towards poor. Upon detecting a predicted or actual decline, the system may trigger stimulation that may be targeted at mitigating further decline and/or supporting positive feelings. One such example of a detectable pattern contributing to a declining life signature would be when consistently poor sleep is detected via wearable actigraphy.

A signature for various other personalized goal states may be developed using sensed or collected data as described herein (e.g. physiological, contextual, environmental, etc.), such as a running goal state/signature, a sleep goal state/signature, an at-work goal state/signature, a performance state, a relaxed state, a focused state, or the like. In one method of establishing a personalized goal state, while receiving a first transcutaneous vibratory output to achieve a desired target state, the user may provide feedback on if they have reached the target state. A user interface may be used by the user to select a target state or input the data regarding whether the user has achieved the desired target state. If the user has achieved the desired target state, at least one of contextual or biometric data of the user may be obtained while the user is in the target state. Biometric data may be obtained with an optionally wearable electronic sensor. Obtaining the contextual data may include receiving data from third-party applications. The at least one of contextual or biometric data of the user while the user is in the target state may be stored, such as in a user profile, as a baseline or personalized goal state. The personalized goal states may be stored in a user profile along with any other additional data, such as identifying data associated with the state and stimulation parameters. A particular stimulation pattern and parameters for its delivery may be associated with maintaining or encouraging entry into the personalized goal state. Continuing with the method, the user's contextual and/or biometric data may be collected again, periodically, or continuously, and used to determine if the user is not in the baseline state. If the user is determined to not be in the baseline state, a transcutaneous vibratory output aimed at assisting the user to achieve the state is generated for application to a portion of the user's body. Either of the first or second transcutaneous vibratory output may be emitted with or through an electronic transducer.

When a predicted state is identified, delivery of a therapeutic stimulation pattern may be triggered, discontinued, modified, tapered, or ramped up. The system may generate or trigger a transcutaneous vibratory output to be applied to a portion of the user's body, such as with a wearable device, to assist the user in at least one of addressing or avoiding the predicted state. As described herein, the transcutaneous vibratory output may have variable parameters comprising a perceived pitch, a perceived beat, and a perceived intensity, wherein each of the variable parameters can be dynamically modified based on, for example, the predicted emotional state, a physiological state or contextual data. In some embodiments, the transcutaneous vibratory output may have multiple segments, wherein each segment may have at least one of a perceived pitch, a perceived beat, and a perceived intensity assigned to it, and wherein each of these variables may be different or the same between segments. Assigning the perceived pitch may be by at least one of increasing or decreasing the perceived pitch. Assigning the perceived beat may be by at least one of increasing or decreasing the perceived beat.

Triggering may be sufficiently in advance of the actual onset of the predicted state such that the stimulation results in avoidance of the predicted state. In embodiments, when the estimated state is determined, a notification may be triggered to a user. The notification may include a suggestion that a therapeutic stimulation protocol be commenced, wherein the user may choose to manually commence the protocol. A response to the stimulation (e.g. from sensors in wearable), movement data, and/or a manual/behavioral response to the therapeutic stimulation (e.g. turning off the stimulation, increasing intensity, changing settings) may be used as feedback to the system. The feedback may be used to identify a current physiological state of the user and may be used to dynamically modify the variable parameters. For example, any one of the perceived pitch, a perceived beat, and a perceived intensity may be modified based on the feedback during application of a first transcutaneous vibratory output, such as to cause a second transcutaneous vibratory output to be generated and applied.

In certain embodiments, the system may use any now or hereafter known machine learning algorithms to define new stimulation patterns and/or update existing stimulation patterns for a user based on collected biometric data, user's manual adjustment in response to stimulation applied to the user (either for training the system and/or in real time), or the like. In some embodiments, the system may utilize machine learning with sensor data to predict an estimated state and may cause or trigger an action in response to a new predicted state. Machine learning may utilize training data from users that includes sensor data, including point, trend, and longitudinal data, associated with known states. An algorithm may use the training data to learn the correlation between the sensor data and the state and be able to predict what the user's state is or that the state is imminent. For example, sensor data, for training, validation or use, may include any of the sensor data types described herein, including GSR, Heart Rate, HF-HRV, HRV interval, other HRV parameters (LF, IBI, Total power, LF/HF ratio, RMSSD, etc.), blood pressure, brain waves (EEG), facial recognition, vocal cues, mobile device usage data, facial recognition, and the like. Machine learning may be used to learn a user's baseline state and predict that the state is changing or has changed, and in embodiments, what the new state is, such as anxious, drowsy, awake, or the like. In embodiments, when the estimated state is predicted, a therapeutic stimulation protocol may be triggered. Triggering may be sufficiently in advance such that the stimulation results in avoidance of the predicted state. In embodiments, when the estimated state is determined, a notification may be triggered to a user of the state. The notification may include a suggestion that a therapeutic stimulation protocol be commenced. A biometric response to the therapeutic stimulation (e.g. from sensors in wearable), movement data, and/or a manual/behavioral response to the therapeutic stimulation (e.g. turning off the stimulation, increasing intensity, changing settings) may also be used as seeds for machine learning.

In an embodiment, delivery of stimulation described herein may be paired, coordinated and/or synchronized with one or more other sensory stimuli 122, such as touch, visual stimulation/sight, sound, olfactory stimulation/smell, taste, electrical, or the like. For example, with a stimulation device, a first transcutaneous vibratory output to be applied to a portion of the user's body may be generated. In some embodiments, the sensory stimulation 122 may be applied with the stimulation device or may be in a separate device. The stimulation device may include both a transducer and a sensory output device. In embodiments, a condition of the user may be assessed. Based on the condition, one or more aspects of the stimulation and/or paired sensory stimuli may be selected or altered. In an embodiment, the sensory stimulation may be based on at least one of the assessed condition of the user or the selected beat output pattern.

In any of the aforementioned embodiments, the transcutaneous vibratory output may be applied concomitantly with a treatment modality (e.g. psychotherapy, physical therapy, mindfulness activity), wherein the treatment modality is based on the condition of the subject or a target state of the subject. In these embodiments, the transcutaneous vibratory output may act synergistically with or augment the treatment modality to achieve a positive outcome or enhance engagement in the treatment modality. An application for guided mindfulness may include a facility for programming and/or initiating delivery of a stimulation therapy and guiding the user through a series of mindfulness prompts, such as guided auditory sessions, during the delivery. The application may prompt the user periodically regarding initiating a delivery of stimulation therapy as part of the guidance. The application user interface may visually depict biometric changes the user experiences during the guidance.

Medical treatments such as prescription drug therapy are widely used to treat various medical conditions and disorders. Many prescription drugs produce side effects and adverse reactions in subjects, which can lead to considerable discomfort and poor quality of life. While such drugs may attenuate a certain disorder, they may exacerbate other disorders. For example, side effects of various drugs may be sleep disorders, loss of appetite or other eating disorders, depression, stress, hypertension, digestive issues, pain, cognitive impairment, etc. Similarly, other medical treatments (e.g., hospitalization, surgery, inpatient procedures, psychotherapy) may also produce side effects such as stress, depression, sleep disorders, hypertension, etc.

At least some of these side effects may be caused due to an imbalance between the sympathetic and parasympathetic branches of the autonomic nervous system (ANS). As such, ways for monitoring the side effects of a medical treatment and mitigating the same by stimulating the sympathetic and/or the parasympathetic branches of the ANS are desired.

In one or more embodiments, the system 100 may be used to address physiological and/or psychological aspects of a subject's functioning that may be attributed to a medical treatment (e.g., drug side effects, effects of psychotherapy, inpatient procedures, etc.). This may include determining what aspect of a subject's functioning have been affected by the medical treatment being administered by collecting physiological data from a subject using a sensor device, analyzing and comparing the physiological data to a baseline state of the subject, and applying vibrational energy to the subject at an appropriate frequency, intensity, duration, etc.

Figure 15:
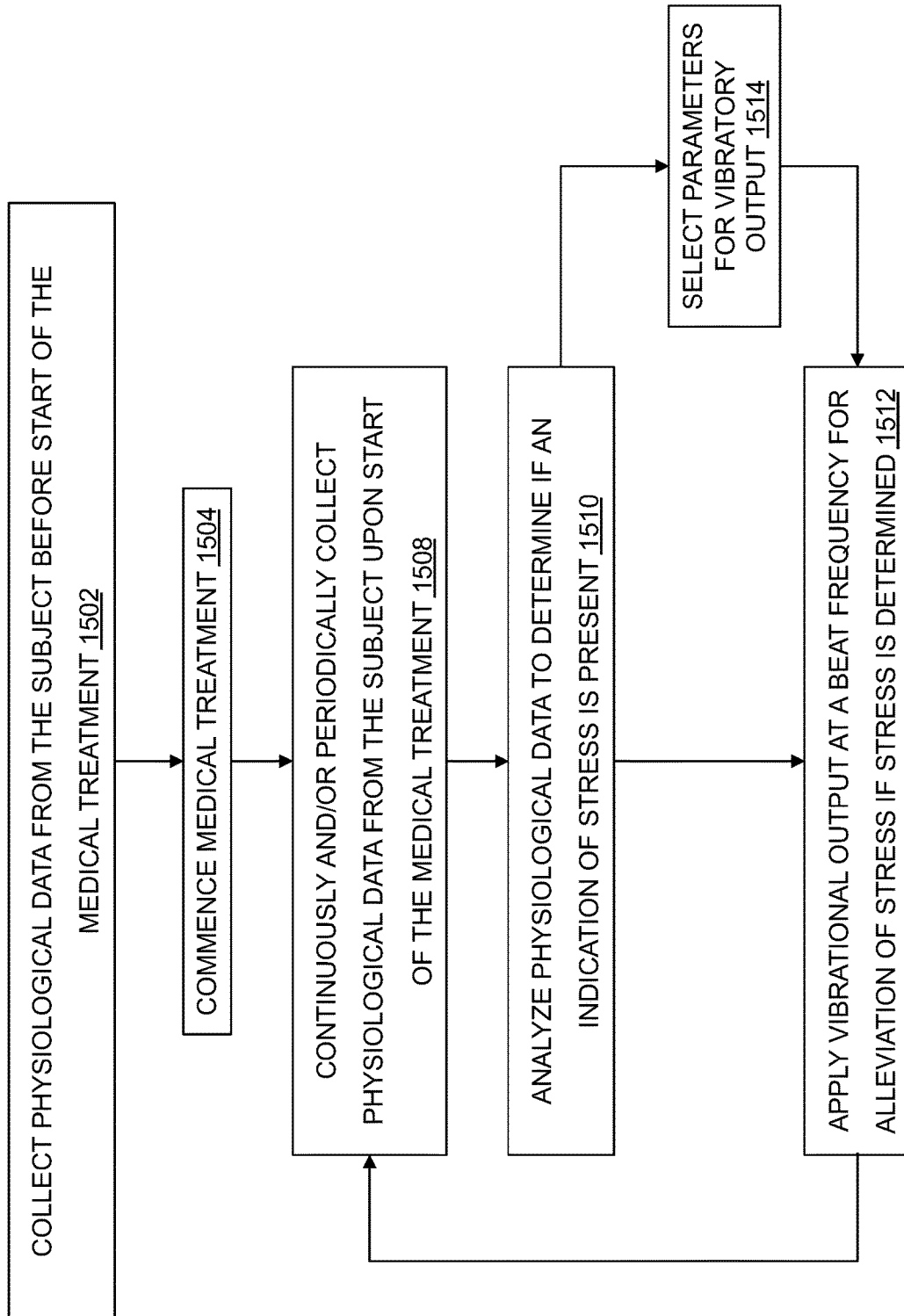
FIG. 15 depicts a process for mitigating negative side effects of a treatment.

In one or more embodiments and referring to FIG. 15, the baseline state of a subject may correspond to the state of a subject prior to the start of a medical treatment (e.g., before drug therapy is started, before hospitalization, etc.), and may include physiological data (corresponding to measurable physiological attributes) collected from the subject before start of the medical treatment 1502. Such physiological data may include, for example and without limitation, heart rate, blood metabolite concentrations, respiration rate, blood pressure, or other quantifiable data that may have a correlation with the potential side effects of the medical treatment. For example, some indications of stress include higher resting pulse rate, frequent sharp spikes in heart rate; shallow respirations, decreased movement for a threshold period of time; high blood pressure; high heart rate with low heart rate variability (in the absence of physical activity); sudden intense increases in sweating (in the absence of physical activity), or combinations thereof. Therefore, if the potential side effect of a medical treatment is stress, the baseline state may include physiological data such as resting pulse rate, heart rate, rate of respiration, blood pressure, etc. Medical treatment may commence 1504 and the system may continuously and/or periodically collect physiological data 1508 from the subject upon start of the medical treatment and analyze it to determine if one or more of the above indications for stress are present 1510. If one or more data collected by the sensor device correlate to conditions of stress, vibrational energy at a beat frequency for alleviation of stress may be applied 1512 to the subject.

Alternatively, and/or additionally, some side effects may be acceptable during a medical treatment and/or the baseline may be different (that is they may be acceptable up to a certain level), and a user or a medical practitioner may define the baseline state accordingly.

A subject may be monitored to identify potential side effects or unwanted effects of a medical treatment during the administration of the medical treatment and/or for a predetermined time after completion the medical treatment. The indications of a side effect may be different and/or the baseline may be different during a medical treatment compared to those upon completion of a medical treatment.

In embodiments, delivery of stimulation described herein may be administered with a compound, such as a pharmaceutical compound, a psychoactive compound (e.g. MDMA), a psychedelic (e.g. psilocybin), an anti-depressant, an anti-anxiety drug, an amphetamine, a medicament, a therapeutic agent, *cannabis*, or the like. In some embodiments, the stimulation may mitigate the negative side effects of the compounds, such as by attenuating the restlessness or anxiety associated with the compound and/or the therapeutic experience. In this embodiment, the stimulation device or an associated device may interpret changes in a parameter of a user's state, which may be attributable to the compound, and then apply a stimulation that enhances or augments the benefit of the compound by mitigating its negative side effects and/or synergizing with or augmenting the beneficial or positive effects of the compound. In some embodiments, the administration of the compound and the stimulation may be done in a controlled session, such as a psychotherapy session. Mitigating the side effects of certain drugs, such as the restlessness that often accompanies many psychoactive drugs, may enhance their use in the psychotherapeutic treatment of certain disorders, such as PTSD or depression, and may enable patients to engage more effectively in therapy.

In practice, a drug or other compound may be administered to a subject in a therapy session, wherein the drug is one of a psychoactive compound (e.g. MDMA, psilocybin), a psychoactive compound, a psychedelic, a therapeutic agent, *cannabis*, or some other herbal or pharmaceutical compound or therapeutic agent. The subject may be monitored to determine if the effects of the drug are counterproductive to the therapy session (e.g. anxiety, restlessness). Monitoring may be done using sensors to generate biometric data of the subject, or may be done by another participant in the therapy session. Sensors may be part of a stimulation device or may be part of another device or environmental. For example, a sensor may be used to determine HRV, which may be associated with anxiety. In another example, the sensor may be an audio sensor that senses vocal data such as a yell, a cry, an increased vocal tone, or the like.

Once determined that the drug is having a negative side effect, the stimulation device may be triggered to provide tactile stimulation to the subject during the therapy session, wherein the transcutaneous vibratory output and/or any of the underlying variable parameters are selected 1514 to reduce the undesirable or unwanted effects of the drug, and in some embodiments, may be based on the kind of effects being experienced. In the case where another participant is monitoring the subject for negative side effects, the stimulation device may be manually triggered to choose and/or deliver a transcutaneous vibratory output. The transcutaneous vibratory output may be a combination of oscillations as described herein (e.g. a perceived pitch or a main oscillation at a first frequency and a perceived beat or a modulation oscillation at a second frequency that together form a beat output; a selected envelope bounded by a base tone; a perceived pitch and a perceived beat). In an embodiment, the beat and/or pitch may be selected based on the effects of the drug. In an embodiment, the perceived pitch and/or perceived beat may be altered based on the effects of the drug.

In addition to applying a stimulation to mitigate the negative side effects of certain drugs, a sensory stimulation may also be applied to the subject. The sensory stimulation may be one or more of a visual stimulation, an olfactory stimulation, a taste stimulation, a touch, or a sound, and may be selected based on the effects of the drug. Further, treatment may be coordinated with one or more other devices for treatment or measurement (e.g. blood pressure cuff, pulse ox, aural stim, light stim, music).

In this embodiment, and in any of the embodiments disclosed herein, the parameters of the applied transcutaneous vibrational energy (e.g., frequency, intensity, duration, etc.) may be determined based on the physiological data collected by the sensor device 118. Typically, fast and high intensity vibrations may cause an increase in heart rate, respirations, blood pressure, and sweat while decreasing heart rate variability. On the other hand, slow, gentle, low intensity vibrations may cause a decrease in heart rate, respirations, blood pressure, and sweat while increasing heart rate variability.

Furthermore, the parameter values and examples in this disclosure are provided for example purposes only and may be adjusted or tuned for a subject based on the subject's physiological reactions and data using a feedback loop, as described herein. Specifically, the parameters may be personalized to a subject based on physiological data collected by the sensor device 118 (e.g., heart rate, heart rate variability, blood pressure, respirations, sweat level, resting pulse rate, brain activity, etc.) and/or based on user feedback. Specifically, in various embodiments, data collected by the sensor device 118 may be used in a feedback loop to initiate and/or control the application of stimulus to the subject, via the stimulation device 102. Additionally, and/or alternatively, the data collected by the sensor device to select and personalize the application of stimulation to the subject 114 may be based on the data collected by the sensor device 118. For example, the frequency ranges, stimulation patterns, stimulation application times, stimulation application duration, or the like may be personalized to a user.

Furthermore, the underlying frequencies of the stimulation may be adjusted based on a subject's response to the application of the beat frequency in a real-time manner. For example, if the data collected by the sensor device 118 indicates that an initial stimulation did not alleviate the stress symptoms (e.g., the resting pulse rate did not decrease to a non-stress level), the applied frequencies may be gradually increased until the desired effect is achieved. Alternatively, and/or additionally, if the data collected by the sensor device 118 indicates that the stimulation is reducing stress in a subject (e.g., the resting pulse rate slowly decreasing), the applied frequencies may be gradually tapered to a shutdown level.

In addition to the beat frequency being controlled in real-time based on data collected by the sensor device 118, user feedback may also be used to control the application of the stimulation (e.g., turning off, turning up intensity, changing settings, etc.)

In certain embodiments, the baseline state of a subject may also correspond to the state of an average person with similar physical attributes as the subject undergoing medical treatment (e.g., same gender, weight, height, BMI, etc.). For example, some indications of stress include, without limitation, a resting pulse of about 60 beats per minute (bpm) for a healthy man and greater than about 70 bpm for a healthy woman; frequent sharp spikes in heart rate; shallow respirations at a rate of greater than about 12 breaths/minute; decreased movement for a threshold period of time; blood pressure greater than 120/80 mm of Hg in a healthy male (in the absence of physical activity); high heart rate with low heart rate variability (in the absence of physical activity); sudden intense increases in sweating (in the absence of physical activity); or combinations thereof.

In embodiments, external or secondary devices and services may be controlled based on current state or goal state achievement, such as determined by a sensor, external data source, or user input. Controlling the operation of third-party devices may be based on the predicted or actual state achieved based on the delivery of stimulation therapy. For example, when a user has reached a state, the stimulation device may be triggered to deliver a stimulation pattern and/or make an environmental adjustment, such as to turn off/on lights, change light color, change room temperature, commence/discontinue aromatherapy, lower/raise window shades, turn on/off music, trigger a secondary stimulating device in a mattress/pillow, etc.). In another embodiment, when the user reaches a state upon having applied stimulation (e.g. more alert), a vibrating car massage seat may be triggered. In another embodiment, when a user has reached a state of emergence from a nap, a red light may be illuminated with increased frequency to aid with exiting the nap. In another embodiment, when a user has reached a state, at least one of a content delivery setting or a content filter for applications and communications may be adjusted. The content filter may determine the types of content delivered to the user. The setting may be a do not disturb setting. In another embodiment, when a user has reached a state, a social media setting may be adjusted, such as a do not disturb setting or a content delivery setting. In another embodiment, when a user has reached a state, they may be prompted to perform a certain a task. In any of the aforementioned examples, controlling operations and services may result from the stimulation device or associated sensor or processor transmitting an instruction or trigger to another device/server or system controller. Alternatively, the other device or server may periodically check the stimulation device, associated sensor/processor, or remote location aggregating data from the same and determine if a triggering event or data point has occurred. In embodiments, the stimulation device may transmit data to a remote server or cloud location that can be accessed by third party devices or controllers to trigger actions.

In embodiments, the system may control the operation of third-party devices to achieve a state based on the delivery of stimulation therapy. For example, when a calming transcutaneous vibratory output commences, the system may instruct dimming of lights in the vicinity. Conversely, if a waking therapy begins, instructions may be sent to brighten lights and lift window blinds.

Figure 16:
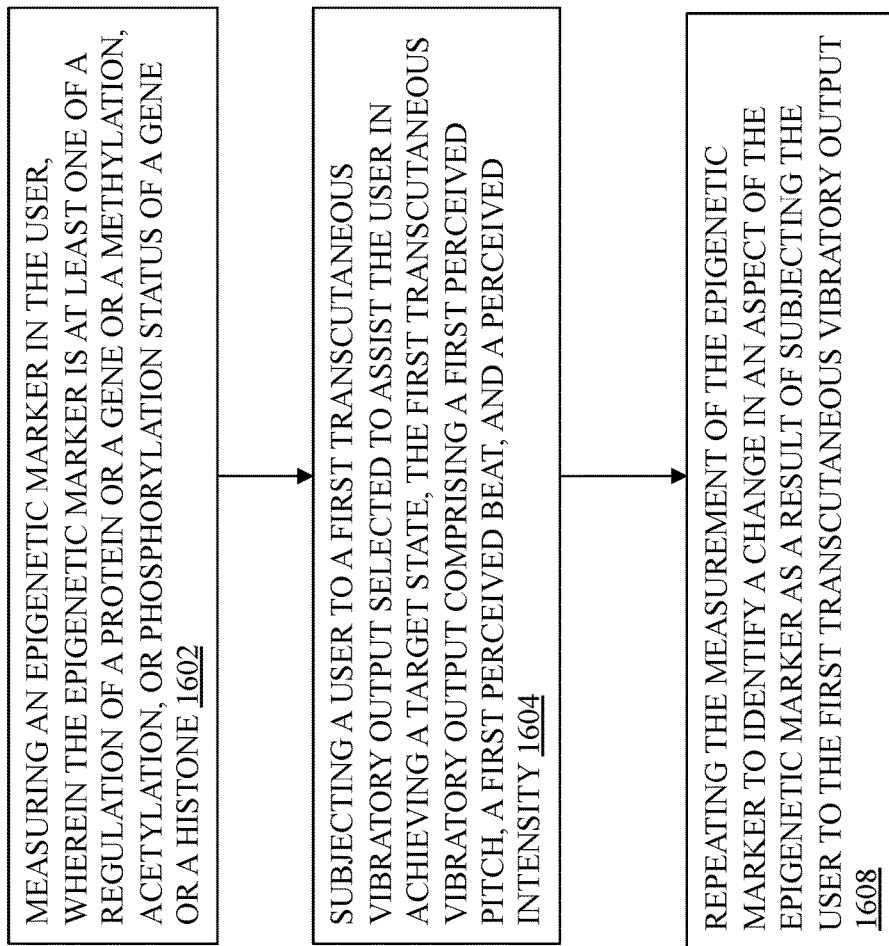
FIG. 16 depicts a process for promoting epigenetic change.

In an embodiment, another solution described herein is how to cause and track epigenetic changes as a result of employing the methods and devices described herein. There is growing evidence that epigenetic regulation of gene expression is related to trauma exposure, may be involved in the pathophysiology and treatment response in PTSD patients, and modifications in epigenetic regulation and the epigenome may be persistent and potentially inheritable by subsequent generations. Some of this evidence relates to methylation and acetylation patterns of certain genes, which is associated with regulating expression levels of the different portions of these genes, which are ultimately transcribed and translated into proteins. In some embodiments and referring to FIG. 16, applying a therapeutic stimulation to achieve a target state 1604 (e.g. mental presence, flow, optimal performance, relaxation, non-depressed, etc.) in accordance with this disclosure and either for a single time, intermittently, or repeatedly over a period of time, may result in the causation of or the priming for a measurable epigenetic change in the incidence of: a psychological state-, illness-, disorder-, trauma-, or stress-related regulation of certain proteins (e.g. stress hormones, receptors, receptor ligands, growth factors, and the like), a methylation/acetylation/phosphorylation pattern of a gene or histone, or the incidence of regulation of a reward response gene or protein (e.g. neurotransmitter, neurotransmitter receptors, ion channels, and the like), wherein regulation can be any of increasing levels, decreasing levels, silencing, and the like. Epigenetic markers may be measured before 1602 and after 1608 transcutaneous vibratory stimulation in order to assess the epigenetic impact of the stimulation. The causation or the priming for epigenetic changes may be a result of the therapeutic stimulation itself, the achievement of the target state and the associated physical manifestations of the target state (e.g. achievement of a resonant frequency or resonant state, improved balance between the parasympathetic and sympathetic nervous system, increases in HRV, etc.), a mechanosensitive change in a receptor or receptor affinity, a downstream effect of a mechanosensitive change in a receptor or receptor affinity, or some combination thereof. In the absence of measuring epigenetic changes directly as described herein (e.g. measuring the methylation or acetylation profile of certain genes pre- and post-treatment, measuring the levels of expression of reward response proteins or stress-related proteins, etc.), certain proxy measurements may be useful in extrapolating an epigenetic change. One proxy may be stress indicators in communications, such as social media posts, mobile device usage, texts, calls, or the like, such as the presence, absence, or frequency of positive or negative words used, or vocal tone/pitch/vocal rate related to the life signature. Another proxy may be a faster time to reach a target state after continued use. Another proxy may be a longer dwell in the target state. In embodiments, stimulation therapy targeted at causing an epigenetic change may be co-delivered with a sensory stimuli, physical therapy/massage, and/or a pharmaceutical treatment.

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer readable medium executing on one or more of the machines. In embodiments, the processor may be part of a server, cloud server, client, network infrastructure, mobile computing platform, stationary computing platform, or other computing platform. A processor may be any kind of computational or processing device capable of executing program instructions, codes, binary instructions, and the like. The processor may be or may include a signal processor, digital processor, embedded processor, microprocessor, or any variant such as a co-processor (math co-processor, graphic co-processor, communication co-processor, and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions, and the like described herein may be implemented in one or more thread. The thread may spawn other threads that may have assigned priorities associated with them; the processor may execute these threads based on priority or any other order based on instructions provided in the program code. The processor, or any machine utilizing one, may include non-transitory memory that stores methods, codes, instructions, and programs as described herein and elsewhere. The processor may access a non-transitory storage medium through an interface that may store methods, codes, and instructions as described herein and elsewhere. The storage medium associated with the processor for storing methods, programs, codes, program instructions, or other type of instructions capable of being executed by the computing or processing device may include but may not be limited to one or more of a CD-ROM, DVD, memory, hard disk, flash drive, RAM, ROM, cache, and the like.

A processor may include one or more cores that may enhance speed and performance of a multiprocessor. In embodiments, the process may be a dual core processor, quad core processors, other chip-level multiprocessor and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server, cloud server, and other variants such as secondary server, host server, distributed server, and the like. The server may include one or more of memories, processors, computer readable transitory and/or non-transitory media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of program across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code, and/or instructions. A central repository may provide program instructions to be executed on different devices. In this implementation, the remote repository may act as a storage medium for program code, instructions, and programs.

The software program may be associated with a client that may include a file client, print client, domain client, internet client, intranet client, and other variants such as secondary client, host client, distributed client, and the like. The client may include one or more of memories, processors, computer readable transitory and/or non-transitory media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers, and the like. Additionally, this coupling and/or connection may facilitate remote execution of a program across the network. The networking of some or all of these devices may facilitate parallel processing of a program or method at one or more location without deviating from the scope of the disclosure. In addition, any of the devices attached to the client through an interface may include at least one storage medium capable of storing methods, programs, applications, code, and/or instructions. A central repository may provide program instructions to be executed on different devices. In this implementation, the remote repository may act as a storage medium for program code, instructions, and programs.

In embodiments, one or more of the controllers, circuits, systems, data collectors, storage systems, network elements, or the like as described throughout this disclosure may be embodied in or on an integrated circuit, such as an analog, digital, or mixed signal circuit, such as a microprocessor, a programmable logic controller, an application-specific integrated circuit, a field programmable gate array, or other circuit, such as embodied on one or more chips disposed on one or more circuit boards, such as to provide in hardware (with potentially accelerated speed, energy performance, input-output performance, or the like) one or more of the functions described herein. This may include setting up circuits with up to billions of logic gates, flip-flops, multiplexers, and other circuits in a small space, facilitating high speed processing, low power dissipation, and reduced manufacturing cost compared with board-level integration. In embodiments, a digital IC, typically a microprocessor, digital signal processor, microcontroller, or the like may use Boolean algebra to process digital signals to embody complex logic, such as involved in the circuits, controllers, and other systems described herein. In embodiments, a data collector, an expert system, a storage system, or the like may be embodied as a digital integrated circuit ("IC"), such as a logic IC, memory chip, interface IC (e.g., a level shifter, a serializer, a deserializer, and the like), a power management IC and/or a programmable device; an analog integrated circuit, such as a linear IC, RF IC, or the like, or a mixed signal IC, such as a data acquisition IC (including A/D converters, D/A converter, digital potentiometers) and/or a clock/timing IC.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM, and the like. The processes, methods, program codes, instructions described herein and elsewhere may be executed by one or more of the network infrastructural elements. The methods and systems described herein may be configured for use with any kind of private, community, or hybrid cloud computing network or cloud computing environment, including those which involve features of software as a service ("SaaS"), platform as a service ("PaaS"), and/or infrastructure as a service ("IaaS").

The methods, program codes, and instructions described herein and elsewhere may be implemented on a cellular network having multiple cells. The cellular network may either be frequency division multiple access ("FDMA") network or code division multiple access ("CDMA") network. The cellular network may include mobile devices, cell sites, base stations, repeaters, antennas, towers, and the like. The cell network may be a GSM, GPRS, 3G, EVDO, mesh, or other networks types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable transitory and/or non-transitory media that may include: computer components, devices, and recording media that retain digital data used for computing for some interval of time; semiconductor storage known as random access memory ("RAM"); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, stand-alone RAM disks, zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The elements described and depicted herein, including in flow charts and block diagrams throughout the Figures, imply logical boundaries between the elements. However, according to software or hardware engineering practices, the depicted elements and the functions thereof may be implemented on machines through computer executable transitory and/or non-transitory media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples, but is to be understood in the broadest sense allowable by law.

The use of the terms "a" and "an" and "the" and similar referents in the context of describing the disclosure (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the disclosure, and does not pose a limitation on the scope of the disclosure unless otherwise claimed. No language in the specification should be construed as indicating any non-claimed element as essential to the practice of the disclosure.

While the foregoing written description enables one skilled in the art to make and use what is considered presently to be the best mode thereof, those skilled in the art will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure.

Any element in a claim that does not explicitly state "means for" performing a specified function, or "step for" performing a specified function, is not to be interpreted as a "means" or "step" clause as specified in 35 U.S.C. § 112(f). In particular, any use of "step of" in the claims is not intended to invoke the provision of 35 U.S.C. § 112(f).

Persons skilled in the art may appreciate that numerous design configurations may be possible to enjoy the functional benefits of the inventive systems. Thus, given the wide variety of configurations and arrangements of embodiments of the present invention, the scope of the invention is reflected by the breadth of the claims below rather than narrowed by the embodiments described above.

What is claimed is:

1. A method of assisting a subject to reach a target state, comprising steps of:

obtaining input of the target state of the subject; and generating, using a motor, a transcutaneous vibratory output to be applied to a portion of a body of the subject to assist the subject in achieving the target state, the transcutaneous vibratory output having variable parameters comprising a perceived pitch, a perceived beat, and a perceived intensity, wherein the step of generating the transcutaneous vibratory output further comprises the steps of:

modifying the variable parameters to correspond to the target state; and multiplicatively combining a sine wave-shaped envelope generated using the perceived beat with a wave pattern generated using the perceived pitch to produce the transcutaneous vibratory output.

2. The method of claim 1, wherein modifying the variable parameters to correspond to the target state further comprises adjusting the perceived pitch.

3. The method of claim 1, wherein modifying the variable parameters to correspond to the target state further comprises adjusting the perceived beat.

4. The method of claim 1, wherein modifying the variable parameters to correspond to the target state further comprises adjusting the perceived intensity.

5. The method of claim 1, wherein the target state is selected from the group consisting of calm, focus, flow, presence of being, asleep, wakeful, relaxed, aroused, or euphoric.

6. The method of claim 1, wherein the step of obtaining input of the target state of the subject further comprises obtaining input of a present condition of the subject.

7. The method of claim 6, wherein the step of obtaining input of the present condition of the subject further comprises collecting biometric data of the subject.

8. The method of claim 1 wherein one or more of the variable parameters are modified in subsequent attempts to reach the target state in order to avoid habituation by the subject.

9. The method of claim 1, wherein multiplicatively combining is in accordance with a relationship:

$$[\sin(2.0*\pi*freq\_perceived\_pitch*t)]*[\sin(\pi*freq\_perceived\_beat*t)].$$

10. The method of claim 1, wherein the transcutaneous vibratory output is applied to a skin of the portion of the body of the subject.

11. The method of claim 1, wherein the transcutaneous vibratory output is applied to the subject via contact with the portion of the body.

12. A method of assisting a subject to reach a target state, comprising steps of:
generating, using a motor, a first transcutaneous vibratory output to be applied to a portion of a body of the subject to assist the subject in achieving the target state, the first transcutaneous vibratory output generated by multiplicatively combining a sine wave-shaped envelope generated using a perceived beat with a wave pattern generated using a perceived pitch, the first transcutaneous vibratory output having variable parameters comprising the perceived pitch, the perceived beat, and a perceived intensity; and
during application of the first transcutaneous vibratory output to the portion of the subject's body, varying at least one of the variable parameters to generate a second transcutaneous vibratory output to be applied to the portion of the subject's body to assist the subject in achieving the target state.

13. The method of claim 12, wherein varying the at least one of the variable parameters further comprises varying the perceived pitch.

14. The method of claim 12, wherein varying the at least one of the variable parameters further comprises varying the perceived beat.

15. The method of claim 12, wherein the target state is selected from the group consisting of calm, focus, flow, presence of being, asleep, wakeful, relaxed, aroused, or euphoric.

16. The method of claim 12, wherein one or more of the variable parameters are modified in subsequent attempts to reach the target state in order to avoid habituation by the subject.

17. The method of claim 12, wherein multiplicatively combining is in accordance with a relationship:

$$[\sin(2.0*\pi*freq\_perceived\_pitch*t)]*[\sin(\pi*freq\_perceived\_beat*t)].$$

18. The method of claim 12, wherein the first transcutaneous vibratory output is applied to a skin of the portion of the body of the subject.

19. The method of claim 12, wherein the first transcutaneous vibratory output is applied to the subject via contact with the portion of the body.

20. A method of generating a tactile transcutaneous vibratory output signal for a stimulation device for applying the tactile transcutaneous vibratory output signal to a subject to achieve a target state, the tactile transcutaneous vibratory output signal comprising a first segment and a second segment, the method comprising steps of:
assigning a first perceived pitch and a first perceived beat based to the first segment;
assigning a second perceived pitch and a second perceived beat to the second segment; and
generating, using a motor, the tactile transcutaneous vibratory output signal, wherein the tactile transcutaneous vibratory output signal comprises the first segment and the second segment, the first segment generated by multiplicatively combining a sine wave-shaped envelope generated using the first perceived beat with a wave pattern generated using the first perceived pitch, and the second segment generated by multiplicatively combining a sine wave-shaped envelope generated using the second perceived beat with a wave pattern generated using the second perceived pitch.

21. The method of claim 20, further comprising providing the stimulation device for administering the tactile transcutaneous vibratory output signal to the subject.

22. The method of claim 20, further comprising providing an interface for a user to assign the first perceived pitch and the first perceived beat to the first segment and the second perceived pitch and the second perceived beat to the second segment.

23. The method of claim 20, further comprising assigning the second perceived pitch by at least one of increasing or decreasing the first perceived pitch.

24. The method of claim 20, further comprising assigning the second perceived beat by at least one of increasing or decreasing the first perceived beat.

25. The method of claim 20, wherein the target state is selected from the group consisting of calm, focus, flow, presence of being, asleep, wakeful, relaxed, aroused, or euphoric.

26. The method of claim 20, wherein one or more of the first perceived pitch, the second perceived pitch, the first perceived beat, or the second perceived beat are modified in subsequent attempts to reach the target state in order to avoid habituation by the subject.

27. The method of claim 20, wherein multiplicatively combining is in accordance with a relationship:

$$[\sin(2.0*\pi*freq\_perceived\_pitch*t)]*[\sin(\pi*freq\_perceived\_beat*t)].$$

28. The method of claim 20, wherein the tactile transcutaneous vibratory output signal is applied to a skin of the subject.

29. The method of claim 20, wherein the tactile transcutaneous vibratory output signal is applied to the subject via contact with a portion of a body of the subject.

* * * * *